(12) United States Patent
Chen et al.

(10) Patent No.: US 8,063,085 B2
(45) Date of Patent: Nov. 22, 2011

(54) SUBSTITUTED HYDANTOINS

(75) Inventors: Shaoqing Chen, Bridgewater, NJ (US);
Nicholas J. S. Huby, Scotch Plains, NJ (US); Norman Kong, West Caldwell, NJ (US); John Anthony Moliterni, Bloomfield, NJ (US); Omar Jose Morales, New Milford, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 512 days.

(21) Appl. No.: 12/331,538

(22) Filed: Dec. 10, 2008

(65) Prior Publication Data

US 2009/0170920 A1 Jul. 2, 2009

Related U.S. Application Data

(60) Provisional application No. 61/103,259, filed on Oct. 7, 2008, provisional application No. 61/015,222, filed on Dec. 20, 2007.

(51) Int. Cl.
*A01N 43/50* (2006.01)
*A61K 31/415* (2006.01)
*C07D 407/00* (2006.01)

(52) U.S. Cl. .................................... 514/389; 548/314.4

(58) Field of Classification Search .................. 514/389; 548/314.4
See application file for complete search history.

(56) References Cited

FOREIGN PATENT DOCUMENTS

| | | |
|---|---|---|
| EP | 1775294 | 4/2007 |
| WO | WO 99/01426 | 1/1999 |
| WO | WO 99/05117 | 2/1999 |
| WO | WO 01/83478 | 11/2001 |
| WO | WO 02/06213 | 1/2002 |
| WO | WO 03/077914 | 9/2003 |
| WO | WO 2004/033632 | 4/2004 |
| WO | WO 2005/009975 | 2/2005 |
| WO | WO 2005/023251 | 3/2005 |
| WO | WO 2006/018188 | 2/2006 |
| WO | WO 2006/029862 | 3/2006 |
| WO | WO 2006/124780 | 11/2006 |
| WO | WO 2007/096259 | 8/2007 |

OTHER PUBLICATIONS

Hyun et al., J. Liq. Chrom. Rel. Technol., 25, pp. 573-588 (2002).
Böhme et al., J. Med. Chem., 23, pp. 405-412 (1980).
Salituro et al., J. Am. Chem. Soc., 112, pp. 760-770 (1990).
Shimizu et al., J. Chem. Soc. Chem. Commun., 867-868 (1986).
Chemical Abstract Service XP002428310, 1931.

*Primary Examiner* — San-Ming Hui
*Assistant Examiner* — Paul Zarek
(74) *Attorney, Agent, or Firm* — George W. Johnston; Patricia S. Rocha-Tramaloni; David E. Wildman

(57) ABSTRACT

The present invention relates to compounds of the formula

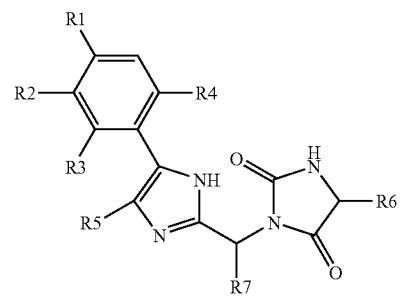

I methods for the preparation thereof, and methods for their use. The compounds are useful in treating diseases characterized by the hyperactivity of MEK. Accordingly the compounds are useful in the treatment of diseases, such as cancer, cognitive and CNS disorders, and inflammatory/autoimmune diseases.

23 Claims, No Drawings

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: FITC-Aca
<220> FEATURE:
<223> OTHER INFORMATION: C-term amidated

<400> SEQUENCE: 1

Xaa Ala Ala Ala Thr Gly Pro Leu Ser Pro Gly Pro Phe Ala
1               5                   10
```

SUBSTITUTED HYDANTOINS

PRIORITY TO RELATED APPLICATION(S)

This application claims the benefit of U.S. Provisional Application No. 61/103,259, filed Oct. 7, 2008 and U.S. Provisional Application No. 61/015,222, filed Dec. 20, 2007. The entire contents of the above-identified applications are hereby incorporated by reference.

FIELD OF THE INVENTION

The present invention relates to hydantoin derivatives and their use as inhibitors of the two protein kinases commonly known as MEK1 and MEK2 for the treatment of human diseases such as cancer. MEK is a commonly used abbreviation for MAP/ERK kinase which is in turn an abbreviation for mitogen activated protein/extracellular signal regulated kinase. MEK is also sometimes referred to as MAPK kinase or MAP kinase.

BACKGROUND OF THE INVENTION

Cancer is a disease characterized by the proliferation of malignant cells and tumors which have the potential for unlimited growth, local expansion and systemic metastasis. This uncontrolled growth is derived from abnormalities in the signal transduction pathways and the response to various growth factors, which differ from those found in normal cells. The abnormalities include changes in the intrinsic activity or in the cellular concentration of one or more signaling proteins in the signaling cascade. These changes are frequently caused by genetic mutations or overexpression of intracellular signaling proteins which can lead to spurious mitogenic signals within the cells.

The mitogen activated protein (MAP) kinase pathway represents one of the best characterized signaling pathways involved in the development and progression of human cancers. This pathway, via the Ras/Raf/MEK/ERK signal cascade, is responsible for transmitting and amplifying mitogenic signals from the cell surface to the nucleus where activated transcription factors regulate gene expression and determine cell fate. The constitutive activation of this pathway is sufficient to induce cellular transformation. Disregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers. The Ras family of GTPase proteins (proteins which convert guanosine triphosphate to guanosine diphosphate) relay signals from activated growth factor receptors to downstream intracellular partners. Prominent among the targets recruited by active membrane-bound Ras are the Raf family of serine/threonine protein kinases. The Raf family is composed of three related kinases (A-, B- and C-Raf) that act as downstream effectors of Ras. Ras-mediated Raf activation in turn triggers activation of MEK1 and MEK2 (MAP/ERK kinases 1 and 2) which in turn phosphorylate ERK1 and ERK2 (extracellular signal-regulated kinases 1 and 2) on both tyrosine-185 and threonine-183. Activated ERK1 and ERK2 translocate and accumulate in the nucleus, where they can phosphorylate a variety of substrates, including transcription factors that control cellular growth and survival. Given the importance of the Ras/Raf/MEK/ERK pathway in the development of human cancers, the kinase components of this signaling cascade are emerging as potentially important targets for the modulation of disease progression in cancer and other proliferative diseases.

MEK1 and MEK2 are members of a larger family of dual-specificity kinases (MEK1-7) that phosphorylate threonine and tyrosine residues of various MAP kinases. MEK1 and MEK2 are encoded by distinct genes, but they share high homology (80%) both within the C-terminal catalytic kinase domains and most of the N-terminal regulatory region. Oncogenic forms of MEK1 and MEK2 have not been found in human cancers, but constitutive activation of MEK has been shown to result in cellular transformation. In addition to Raf, MEK can also be activated by other oncogenes as well. So far, the only known substrates of MEK1 and MEK2 are ERK1 and ERK2. This unusual substrate specificity in addition to the unique ability to phosphorylate both tyrosine and threonine residues places MEK1 and MEK2 at a critical point in the signal transduction cascade which allows it to integrate many extracellular signals into the MAPK pathway.

Previously reported studies with the MEK inhibitors (i) 2-(2-chloro-4-iodo-phenylamino)-N-cyclopropylmethoxy-3,4-difluoro-benzamide, also known as Cl-1040 (PCT publication No. WO 99/01426), (ii) N-[(2S)-2,3-dihydroxypropoxy]-3,4-difluoro-2-[(2-fluoro-4-iodophenyl)amino]-benzamide, also known as PD0325901 (PCT publication No. WO 02/006213) and (iii) 6-(4-bromo-2-chloro-phenylamino)-7-fluoro-3-methyl-3H-benzimidazole-5-carboxylic acid (2-hydroxy-ethoxy)-amide, also know as AZD6244 or Arry142866 (PCT publication No. WO 03/077914) provide further evidence that MEK1 and MEK2 represent an attractive target for pharmacological intervention in cancer or other human diseases characterized by the hyperactivity of MEK and diseases regulated by the MAPK pathway.

Substituted hydantoins have previously been reported as glucokinase activators (PCT publication No. WO 01/83478) and MEK inhibitors (PCT publications No. WO 06/018188, WO 06/029862 and WO 07/096,259). In none of these reports are structures related to those described in the present application disclosed.

SUMMARY OF THE INVENTION

This invention relates to compounds of formula I:

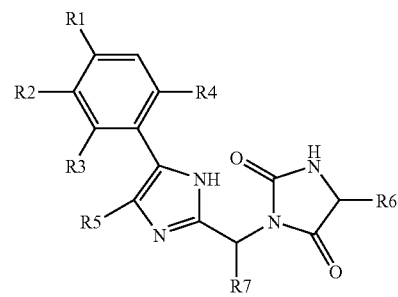

or pharmaceutically acceptable salts thereof, where R1, R2, R3, R4, R5, R6, R7, R8, R9 and R10 are as described in this application. These compounds inhibit the enzymes MEK 1 and MEK2, protein kinases that are components of the MAP kinase signal transduction pathway and as such the compounds will have anti-hyperproliferative cellular activity.

DETAILED DESCRIPTION OF THE INVENTION

The present invention is directed to compounds of formula I:

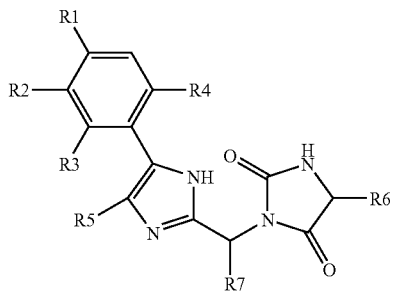

where:
R1 is selected from the group consisting of halogen and lower alkynyl;
R2 is selected from the group consisting of hydrogen and fluorine;
R3 and R4 are independently selected from the group consisting of hydrogen, halogen, and lower alkyl;
R5 is selected from the group consisting of hydrogen, chlorine, and lower alkyl;
R6 is selected from the group consisting of optionally substituted aryl, $C_3$ to $C_7$ cycloalkyl, —$(CH_2)_n$—$C_3$ to $C_7$cycloalkyl, —$(CH_2)_n$-lower alkynyl, or —$(CH_2)_m$CO—X, where X is a member selected from the group consisting of lower alkoxy, hydroxy, and NH—O—$(CH_2)_2$—OH, each n is independently 0, 1, or 2 and m is 1 or 2;
R7 is hydrogen or

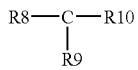

where R8 is selected from the group consisting of hydrogen, lower alkyl, lower alkoxy, optionally substituted benzyl, optionally substituted aryl, and optionally substituted heteroaryl; or
R7 and the carbon to which it is attached form cyclopropyl;
R9 and R10 are independently selected from the group consisting of hydrogen and lower alkyl; or
R9 and R10, together with the carbon to which they are attached, can form a C3 to C7 cycloalkyl group and R8 is hydrogen;
and pharmaceutically acceptable salts or esters thereof.

The present invention is also directed to compounds of formula I:

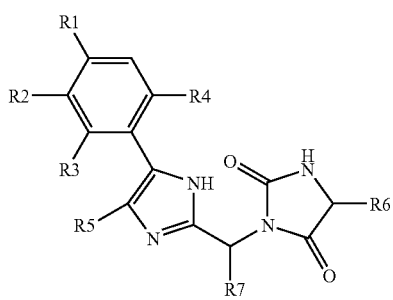

wherein:
R1 is selected from the group consisting of chloro, bromo, iodo, and ethynyl;
R2 is selected from the group consisting of hydrogen and fluorine;
R3 and R4 are independently selected from the group consisting of hydrogen, chlorine, fluorine, and lower alkyl;
R5 is selected from the group consisting of hydrogen, chlorine, and lower alkyl;
R6 is selected from the group consisting of optionally substituted phenyl, cyclopropyl, —$(CH_2)_n$-lower cycloalkyl, —$(CH_2)_n$-ethynyl, or —$(CH_2)_m$CO—X, wherein X is a member selected from the group consisting of methoxy, hydroxy, and NH—O—$(CH_2)_2$—OH and each n is independently 0, 1, or 2 and m is either 1 or 2;
R7 is

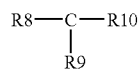

where R8 is selected from the group consisting of hydrogen, lower alkyl, alkoxy, benzyl, optionally substituted aryl, and optionally substituted heteroaryl;
R9 and R10 are independently selected from the group consisting of hydrogen and lower alkyl; or
R9 and R10, together with the carbon to which they are attached, can form a lower cycloalkyl group and R8 is hydrogen;
and pharmaceutically acceptable salts or esters thereof.

In another aspect the invention is directed to compounds of formula I where R5 is hydrogen or chlorine, and in particular when R5 is chlorine.

In another aspect the invention is directed to compounds of formula I where R8 is optionally substituted aryl.

In another aspect the invention is directed to compounds of formula I where R8 is optionally substituted heteroaryl.

In another aspect the invention is directed to compounds of formula I where R8 is lower alkyl or lower alkoxy.

In another aspect the invention is directed to compounds of formula I where R1 is chloro, bromo, iodo, or ethynyl, R2 is hydrogen, R3 and R4 are independently selected from hydrogen, fluorine, chlorine, or methyl, R5 is hydrogen or chlorine, R6 is optionally substituted aryl, R7 is

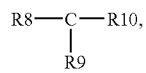

R8 is alkoxy or optionally substituted aryl, R9 is hydrogen, and R10 is hydrogen or methyl.

In another aspect the invention is directed to compounds of formula I where R1 is chloro, bromo or iodo, R2 is hydrogen, R3 and R4 are hydrogen, fluorine, chlorine, or methyl, R5 is hydrogen or chlorine, R6 is optionally substituted phenyl, R7 is

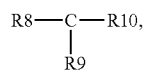

R8 is optionally substituted phenyl, R9 is hydrogen, and R10 is hydrogen or methyl.

In another aspect the invention is directed to compounds of formula I where R1 is chloro, bromo or iodo, R2 is hydrogen, R3 and R4 are independently hydrogen, fluorine, chlorine, or methyl, R5 is hydrogen or chlorine, R6 is phenyl substituted by alkoxy, R7 is

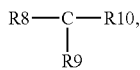

R8 is unsubstituted phenyl or phenyl substituted by cyano, trifluoromethyl, methoxy, fluoro, chloro, bromo, or iodo, R9 is hydrogen, and R10 is hydrogen or methyl.

In another aspect the invention is directed to compounds of formula I where R1 is chloro, bromo or iodo, R2 is hydrogen, R3 and R4 are independently hydrogen, fluorine, chlorine, or methyl, R5 is hydrogen or chlorine, R6 is phenyl substituted by alkoxy, R7 is

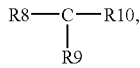

R8 is lower alkyl or lower alkoxy, R9 is hydrogen, and R10 is hydrogen or methyl.

In another aspect the invention is directed to compounds of formula I where R1 is chloro, bromo or iodo, R2 is hydrogen, R3 and R4 are hydrogen, fluorine, chlorine, or methyl, R5 is hydrogen or chlorine, R6 is phenyl substituted by 2-hydroxy-ethoxy or 2,3-dihydroxypropoxy, R7 is

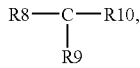

R8 is lower alkyl or lower alkoxy, R9 is hydrogen, and R10 is hydrogen or methyl.

Particularly preferred compounds are: (R)-5-[4-(2-Hydroxy-ethoxy)-phenyl]-3-{(S)-1-[5-(4-iodo-phenyl)-1H-imidazol-2-yl]-2-phenyl-ethyl}-imidazolidine-2,4-dione;
(R)-5-[4-(2-Hydroxy-ethoxy)-phenyl]-3-{(1S,2S)-1-[5-(4-iodo-phenyl)-1H-imidazol-2-yl]-2-phenyl-propyl}-imidazolidine-2,4-dione;
(R)-5-[4-(2-Hydroxy-ethoxy)-phenyl]-3-{(S)-1-[5-(4-iodo-phenyl)-1H-imidazol-2-yl]-2-methyl-propyl}-imidazolidine-2,4-dione;
(R)-5-[4-(2-Hydroxy-ethoxy)-phenyl]-3-{(1R,2R)-1-[5-(4-iodo-phenyl)-1H-imidazol-2-yl]-2-methoxy-propyl}-imidazolidine-2,4-dione;
2-[4-((R)-1-{(1S,2S)-1-[5-(4-Bromo-2-chloro-phenyl)-1H-imidazol-2-yl]-2-phenyl-propyl}-2,5-dioxo-imidazolidin-4-yl)-phenoxy]-N,N-dimethyl-acetamide;
2-[4-((R)-1-{(1S,2S)-1-[5-(4-Chloro-2-fluoro-phenyl)-1H-imidazol-2-yl]-2-phenyl-propyl}-2,5-dioxo-imidazolidin-4-yl)-phenoxy]-N,N-dimethyl-acetamide;
((R)-1-{(1S,2S)-1-[5-(4-Iodo-phenyl)-1H-imidazol-2-yl]-2-phenyl-propyl}-2,5-dioxo-imidazolidin-4-yl)-acetic acid; hydrogen chloride salt; N-(2-Hydroxy-ethoxy)-2-((R)-1-{(1S,2S)-1-[5-(4-iodo-phenyl)-1H-imidazol-2-yl]-2-phenyl-propyl}-2,5-dioxo-imidazolidin-4-yl)-acetamide;
3-((R)-1-{(S)-1-[5-(4-Iodo-phenyl)-1H-imidazol-2-yl]-2-methyl-propyl}-2,5-dioxo-imidazolidin-4-yl)-propionic acid; hydrogen chloride salt;
N-(2-Hydroxy-ethoxy)-3-((R)-1-{(S)-1-[5-(4-iodo-phenyl)-1H-imidazol-2-yl]-2-methyl-propyl}-2,5-dioxo-imidazolidin-4-yl)-propionamide;
3-((R)-1-{(S)-1-[5-(4-Iodo-phenyl)-1H-imidazol-2-yl]-2-methyl-propyl}-2,5-dioxo-imidazolidin-4-yl)-propionic acid methyl ester;
(R)-3-{(1S,2S)-1-[5-(4-Bromo-2-methyl-phenyl)-1H-imidazol-2-yl]-2-phenyl-propyl}-5-[4-(2-hydroxy-ethoxy)-phenyl]-imidazolidine-2,4-dione;
(R)-5-[4-(2-Hydroxy-ethoxy)-phenyl]-3-[(S)-1-[5-(4-iodo-phenyl)-1H-imidazol-2-yl]-2-(2-trifluoromethyl-phenyl)-ethyl]-imidazolidine-2,4-dione;
(R)-3-{(1S,2S)-1-[5-(2-Fluoro-phenyl)-1H-imidazol-2-yl]-2-phenyl-propyl}-5-[4-(2-hydroxy-ethoxy)-phenyl]-imidazolidine-2,4-dione;
(R)-3-{(S)-1-[5-(4-Iodo-phenyl)-1H-imidazol-2-yl]-2-phenyl-ethyl}-5-prop-2-ynyl-imidazolidine-2,4-dione;
(R)-3-{(1S,2S)-1-[5-(4-Bromo-2-chloro-phenyl)-1H-imidazol-2-yl]-2-phenyl-propyl}-5-cyclopropyl-imidazolidine-2,4-dione;
(R)-3-{(S)-1-[5-(4-Bromo-3-fluoro-phenyl)-1H-imidazol-2-yl]-2-phenyl-ethyl}-5-[4-(2-hydroxy-ethoxy)-phenyl]-imidazolidine-2,4-dione;
(R)-3-{(1S,2S)-1-[5-(2-Fluoro-4-iodo-phenyl)-1H-imidazol-2-yl]-2-methyl-butyl}-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-2-thiazol-4-yl-ethyl}-5-[4-(2-hydroxy-ethoxy)-phenyl]-imidazolidine-2,4-dione;
(R)-3-{(S)-Cyclopropyl-[5-(2-fluoro-4-iodo-phenyl)-1H-imidazol-2-yl]-methyl}-5-[4-(2-hydroxy-ethoxy)-phenyl]-imidazolidine-2,4-dione;
(R)-3-[(S)-1-[5-(2-Fluoro-4-iodo-phenyl)-1H-imidazol-2-yl]-2-(2-fluoro-phenyl)-ethyl]-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-3-phenyl-propyl}-5-[4-(2-hydroxy-ethoxy)-phenyl]-imidazolidine-2,4-dione;
(R)-3-{(S)-2-(2-Chloro-phenyl)-1-[5-(2-fluoro-4-iodo-phenyl)-1H-imidazol-2-yl]-ethyl}-5-[4-(2-hydroxy-ethoxy)-phenyl]-imidazolidine-2,4-dione;
(R)-5-[4-(2-Hydroxy-ethoxy)-phenyl]-3-[(S)-1-[5-(4-iodo-phenyl)-1H-imidazol-2-yl]-2-(4-methoxy-phenyl)-ethyl]-imidazolidine-2,4-dione;
(R)-3-{(1R,2R)-1-[5-(2-Fluoro-4-iodo-phenyl)-1H-imidazol-2-yl]-2-methoxy-propyl}-5-[4-(2-hydroxy-ethoxy)-phenyl]-imidazolidine-2,4-dione;
(R)-3-{(1S,2S)-1-[5-(4-Ethynyl-2-fluoro-phenyl)-1H-imidazol-2-yl]-2-phenyl-propyl}-5-[4-(2-hydroxy-ethoxy)-phenyl]-imidazolidine-2,4-dione;
(R)-3-[(S)-1-[5-(2-Fluoro-4-iodo-phenyl)-1H-imidazol-2-yl]-2-(4-fluoro-phenyl)-ethyl]-5-[4-(2-hydroxy-ethoxy)-phenyl]-imidazolidine-2,4-dione;
4-((S)-2-[5-(2-Fluoro-4-iodo-phenyl)-1H-imidazol-2-yl]-2-{(R)-4-[4-(2-hydroxy-ethoxy)-phenyl]-2,5-dioxo-imidazolidin-1-yl}-ethyl)-benzonitrile;
(R)-5-[4-((R)-2,3-Dihydroxy-propoxy)-phenyl]-3-{(S)-1-[5-(2-fluoro-4-iodo-phenyl)-1H-imidazol-2-yl]-2-methyl-propyl}-imidazolidine-2,4-dione;
(R)-3-{(1S,2S)-1-[5-(2-Chloro-4-iodo-phenyl)-1H-imidazol-2-yl]-2-phenyl-propyl}-5-[4-(2-hydroxy-ethoxy)-phenyl]-imidazolidine-2,4-dione;
(R)-5-[4-((R)-2,3-Dihydroxy-propoxy)-phenyl]-3-{(1S,2S)-1-[5-(2-fluoro-4-iodo-phenyl)-1H-imidazol-2-yl]-2-phenyl-propyl}-imidazolidine-2,4-dione;

(R)-3-{(1S,2S)-1-[5-(2-Chloro-4-iodo-phenyl)-1H-imidazol-2-yl]-2-phenyl-propyl}-5-[4-((R)-2,3-dihydroxy-propoxy)-phenyl]-imidazolidine-2,4-dione;
3-((R)-1-{(S)-1-[5-(4-Iodo-phenyl)-1H-imidazol-2-yl]-2-methyl-propyl}-2,5-dioxo-imidazolidin-4-yl)-propionic acid tert-butyl ester;
3-((R)-1-{(S)-1-[5-(4-Iodo-phenyl)-1H-imidazol-2-yl]-2-methyl-propyl}-2,5-dioxo-imidazolidin-4-yl)-N-(2-vinyloxy-ethoxy)-propionamide;
(R)-5-[4-(2-Hydroxy-ethoxy)-phenyl]-3-{(S)-1-[5-(4-iodo-phenyl)-1H-imidazol-2-yl]-1-methyl-2-phenyl-ethyl}-imidazolidine-2,4-dione;
(R)-3-{(S)-2-(4-Fluoro-phenyl)-1-[5-(4-iodo-phenyl)-1H-imidazol-2-yl]-ethyl}-5-[4-(2-hydroxy-ethoxy)-phenyl]-imidazolidine-2,4-dione;
2-((R)-1-{(1S,2S)-1-[5-(4-Iodo-phenyl)-1H-imidazol-2-yl]-2-phenyl-propyl}-2,5-dioxo-imidazolidin-4-yl)-N-(2-vinyloxy-ethoxy)-acetamide;
(R)-3-[5-(2-Fluoro-4-iodo-phenyl)-1H-imidazol-2-ylmethyl]-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-ethyl}-5-[4-(2-hydroxy-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-ethyl}-imidazolidine-2,4-dione;
(R)-3-{(S)-1-[5-(2-Fluoro-4-iodo-phenyl)-1H-imidazol-2-yl]-2-methyl-propyl}-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-3-methyl-butyl}-5-[4-(2-hydroxy-ethoxy)-phenyl]-imidazolidine-2,4-dione;
(R)-3-{(S)-2-Cyclohexyl-1-[5-(2-fluoro-4-iodo-phenyl)-1H-imidazol-2-yl]-ethyl}-5-[4-(2-hydroxy-ethoxy)-phenyl]-imidazolidine-2,4-dione;
(R)-3-{1-[5-(2-Fluoro-4-iodo-phenyl)-1H-imidazol-2-yl]-cyclopropyl}-5-[4-(2-hydroxy-ethoxy)-phenyl]-imidazolidine-2,4-dione;
5-[4-((R)-2,3-Dihydroxy-propoxy)-phenyl]-3-{(1R,2R)-1-[5-(2-fluoro-4-iodo-phenyl)-1H-imidazol-2-yl]-2-methoxy-propyl}-imidazolidine-2,4-dione;
(R)-3-{(S)-1-[5-(2-Fluoro-4-iodo-phenyl)-1H-imidazol-2-yl]-2-phenyl-ethyl}-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-2-phenyl-ethyl}-5-[4-(2-methoxy-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-2-phenyl-ethyl}-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-methoxy-ethoxy)-phenyl]-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-2-thiazol-4-yl-ethyl}-imidazolidine-2,4-dione;
(R)-3-{(1S,2S)-1-[5-(2,6-Difluoro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2,6-Difluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
(R)-3-[5-(2-Chloro-4-iodo-phenyl)-1H-imidazol-2-ylmethyl]-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-ethyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-butyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-pentyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-3-methyl-butyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-2-phenyl-ethyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-2-phenyl-ethyl}-5-[4-((R)-2,3-dihydroxy-propoxy)-phenyl]-imidazolidine-2,4-dione;
2-[4-((R)-1-{(S)-1-[5-(2-Chloro-4-iodo-phenyl)-1H-imidazol-2-yl]-2-phenyl-ethyl}-2,5-dioxo-imidazolidin-4-yl)-phenoxy]-N,N-dimethyl-acetamide;
(R)-3-{(1S,2S)-1-[5-(2-Chloro-4-iodo-phenyl)-1H-imidazol-2-yl]-2-phenyl-propyl}-5-cyclopropyl-imidazolidine-2,4-dione;
3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2-Chloro-4-iodo-phenyl)-1H-imidazol-2-yl]-2-phenyl-propyl}-5-[4-((S)-2,3-dihydroxy-propoxy)-phenyl]-imidazolidine-2,4-dione;
(R)-3-{(1S,2S)-1-[5-(2-Chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
2-[4-((R)-1-{(1S,2S)-1-[5-(2-Chloro-4-iodo-phenyl)-1H-imidazol-2-yl]-2-phenyl-propyl}-2,5-dioxo-imidazolidin-4-yl)-phenoxy]-N,N-dimethyl-acetamide;
(R)-3-{(1R,2R)-1-[5-(4-Bromo-phenyl)-1H-imidazol-2-yl]-2-methoxy-propyl}-5-[4-(2-hydroxy-ethoxy)-phenyl]-imidazolidine-2,4-dione;
(R)-3-{(S)-1-[5-(4-Bromo-phenyl)-1H-imidazol-2-yl]-2-phenyl-ethyl}-5-[4-(2-hydroxy-ethoxy)-phenyl]-imidazolidine-2,4-dione;
(R)-3-{(1S,2S)-1-[5-(4-Bromo-phenyl)-1H-imidazol-2-yl]-2-phenyl-propyl}-5-[4-(2-hydroxy-ethoxy)-phenyl]-imidazolidine-2,4-dione;
(R)-3-{(S)-1-[5-(4-Bromo-2-fluoro-phenyl)-1H-imidazol-2-yl]-2-phenyl-ethyl}-5-[4-(2-hydroxy-ethoxy)-phenyl]-imidazolidine-2,4-dione;
2-[4-((R)-1-{(S)-1-[5-(4-Bromo-2-fluoro-phenyl)-1H-imidazol-2-yl]-2-phenyl-ethyl}-2,5-dioxo-imidazolidin-4-yl)-phenoxy]-N,N-dimethyl-acetamide;
(R)-3-{(1S,2S)-1-[5-(4-Bromo-2-fluoro-phenyl)-1H-imidazol-2-yl]-2-phenyl-propyl}-5-[4-(2-hydroxy-ethoxy)-phenyl]-imidazolidine-2,4-dione;
2-[4-((R)-1-{(1S,2S)-1-[5-(4-Bromo-2-fluoro-phenyl)-1H-imidazol-2-yl]-2-phenyl-propyl}-2,5-dioxo-imidazolidin-4-yl)-phenoxy]-N,N-dimethyl-acetamide;
2-[4-((R)-1-{(S)-1-[5-(4-Bromo-2-chloro-phenyl)-1H-imidazol-2-yl]-2-phenyl-ethyl}-2,5-dioxo-imidazolidin-4-yl)-phenoxy]-N,N-dimethyl-acetamide;

(R)-3-{(S)-1-[5-(4-Bromo-2-chloro-phenyl)-1H-imidazol-2-yl]-2-phenyl-ethyl}-5-[4-(2-oxo-2-pyrrolidin-1-yl-ethoxy)-phenyl]-imidazolidine-2,4-dione;
(R)-3-{(1S,2S)-1-[5-(4-Bromo-2-chloro-phenyl)-1H-imidazol-2-yl]-2-phenyl-propyl}-5-[4-(2-hydroxy-ethoxy)-phenyl]-imidazolidine-2,4-dione;
(R)-3-{(S)-1-[5-(4-Bromo-2-chloro-phenyl)-1H-imidazol-2-yl]-2-thiazol-4-yl-ethyl}-5-[4-(2-hydroxy-ethoxy)-phenyl]-imidazolidine-2,4-dione;
(R)-3-{(1S,2S)-1-[5-(4-Bromo-2,6-difluoro-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(4-Bromo-2,6-difluoro-phenyl)-1H-imidazol-2-yl]-2-phenyl-propyl}-5-[4-((R)-2,3-dihydroxy-propoxy)-phenyl]-imidazolidine-2,4-dione;
(R)-3-{(S)-1-[5-(4-Chloro-phenyl)-1H-imidazol-2-yl]-2-phenyl-ethyl}-5-[4-(2-hydroxy-ethoxy)-phenyl]-imidazolidine-2,4-dione;
(R)-3-{(1S,2S)-1-[5-(4-Chloro-phenyl)-1H-imidazol-2-yl]-2-phenyl-propyl}-5-[4-(2-hydroxy-ethoxy)-phenyl]-imidazolidine-2,4-dione;
(R)-3-{(S)-1-[5-(4-Chloro-2-fluoro-phenyl)-1H-imidazol-2-yl]-ethyl}-5-[4-(2-hydroxy-ethoxy)-phenyl]-imidazolidine-2,4-dione;
(R)-3-{(1S,2S)-1-[5-(4-Chloro-2-fluoro-phenyl)-1H-imidazol-2-yl]-2-phenyl-propyl}-5-[4-(2-hydroxy-ethoxy)-phenyl]-imidazolidine-2,4-dione; and
(R)-3-{(1S,2S)-1-[5-(2,4-Dichloro-phenyl)-1H-imidazol-2-yl]-2-phenyl-propyl}-5-[4-(2-hydroxy-ethoxy)-phenyl]-imidazolidine-2,4-dione.

Other particularly preferred compounds of the invention are:
(R)-3-{(1S,2S)-1-[4-Chloro-5-(2-fluoro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[4-Chloro-5-(4-chloro-2-fluoro-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione;
(R)-3-{(S)-1-[4-Chloro-5-(4-iodo-phenyl)-1H-imidazol-2-yl]-2-phenyl-ethyl}-5-[4-(2-hydroxy-ethoxy)-phenyl]-imidazolidine-2,4-dione;
(R)-3-{(1S,2S)-1-[4-Chloro-5-(2-fluoro-4-iodo-phenyl)-1H-imidazol-2-yl]-2-phenyl-propyl}-5-[4-((R)-2,3-dihydroxy-propoxy)-phenyl]-imidazolidine-2,4-dione;
(R)-3-{(1S,2S)-1-[4-Chloro-5-(2-fluoro-4-iodo-phenyl)-1H-imidazol-2-yl]-2-phenyl-propyl}-5-[4-((S)-2,3-dihydroxy-propoxy)-phenyl]-imidazolidine-2,4-dione;
(R)-3-{(1S,2S)-1-[4-Chloro-5-(2-fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
(R)-3-{(1S,2S)-1-[4-Chloro-5-(2-chloro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[4-Chloro-5-(2-chloro-4-iodo-phenyl)-1H-imidazol-2-yl]-2-phenyl-propyl}-5-[4-((R)-2,3-dihydroxy-propoxy)-phenyl]-imidazolidine-2,4-dione;
(R)-3-{(1S,2S)-1-[4-Chloro-5-(2-chloro-4-iodo-phenyl)-1H-imidazol-2-yl]-2-phenyl-propyl}-5-[4-((S)-2,3-dihydroxy-propoxy)-phenyl]-imidazolidine-2,4-dione; and
(R)-3-{(1S,2S)-1-[4-Chloro-5-(2-chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione.

"Alkyl" denotes a straight-chained, branched or cyclic saturated aliphatic hydrocarbon. Preferably, alkyl denotes a lower alkyl group i.e., a C1 to C6 alkyl group and includes methyl, ethyl, propyl, isopropyl, butyl, t-butyl, 2-butyl, pentyl, hexyl, and the like. Lower alkyl is preferably C1 to C4 alkyl, and more preferably C1 to C3 alkyl. Examples of cycloalkyl groups are moieties having 3 to 10, preferably 3 to 7 carbon atoms including cyclopropyl, cyclopentyl and cyclohexyl groups. Lower cycloalkyl is preferably C3 to C6 cycloalkyl, and preferably C3 to C5 cycloalkyl.

"Trihaloalkyl" means an alkyl group in which the three hydrogens of one of the terminal carbon atoms are replaced by halogen, e.g., trifluoromethyl, trichloromethyl, 1,1,1-trifluoroethyl, 1,1,1-trichloropropyl, and the like. "Trihalo lower alkyl" denotes a trihaloalkyl group with one to six carbon atoms, preferably one to three carbon atoms.

"Aryl" means a monovalent, monocyclic or bicyclic, aromatic carbocyclic radical, preferably a 6 to 10 member aromatic ring system. Preferred aryl groups include, but are not limited to, phenyl, naphthyl, tolyl, and xylyl. "Heteroaryl" means a monovalent, monocyclic or bicyclic aromatic heterocyclyl radical, preferably a 6 to 10 member aromatic ring system. Preferred heteroaryl groups include, but are not limited to, thienyl, furyl, indolyl, pyrrolyl, pyridinyl, oxy-pyridinyl, pyrazinyl, oxazolyl, thiaxolyl, quinolinyl, pyrimidinyl, imidazole and tetrazolyl. Aryl and heteroaryl groups can be optionally substituted by, for example, one or more lower alkyl, cycloalkyl, e.g., cyclopropyl, trihalo-lower alkyl, e.g., trifluoromethyl, hydroxyl, alkoxy, especially lower alkoxy, mono or dihydroxyl-substituted alkoxy, acetamido, methoxyacetamido, dimethylaminoacetamido, halogen, e.g., fluoro, chloro, or bromo, aniline derivatives, amide derivatives of the aniline derivatives and methanesulfonyl. When two or more substituents are present on an aryl or heteroaryl group they may also be present in the form of a fused ring. Such fused rings include, but are not limited to, 3,4-methylenedioxyphenyl and 3,4-ethylenedioxyphenyl.

"Heteroatom" means an atom selected from N, O and S.

"Heterocyclyl" means a group having four to six carbon atoms and at least one heteroatom.

"Alkoxy or lower alkoxy" refers to any of the above lower alkyl groups attached to an oxygen atom. Typical lower alkoxy groups include methoxy, ethoxy, isopropoxy or propoxy, butyloxy, including tertiary butoxy, cyclopropyl methoxy, and the like. Further included within the meaning of alkoxy are multiple alkoxy side chains, e.g. ethoxy methoxy ethoxy, methoxy ethoxy, methyl oxetanyl methoxy and the like. Also included are substituted alkoxy side chains, e.g., hydroxyethoxy, dihydroxypropoxy, dimethylamino ethoxy, diethylamino ethoxy, phosphoryl methoxy, dimethoxy-phosphoryl methoxy, carbamoyl methoxy, methyl and dimethyl carbamoyl methoxy, carbamoyl ethoxy, methyl and dimethyl carbamoyl ethoxy, azetidinyl carbamoyl ethoxy, vinyloxy-ethoxy, bishydroxyethyl methoxy, bishydroxyethylcarbamoyl methoxy, morpholinyl methoxy, morpholinyl ethoxy, piperazinyl methoxy, piperazinyl ethoxy, lower-alkyl piperazine ethoxy, oxo-pyrrolidinyl ethoxy, and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard Hans ed. (Elsevier, 1985). See also, Ansel et. al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount or effective amount" means an amount of at least one designated compound that significantly inhibits proliferation and/or prevents differentiation of a human tumor cell, including human tumor cell lines.

The compounds of the present invention are useful in the treatment or control of cell proliferative disorders such as inflammatory/autoimmune disorders, e.g., restenosis, cognitive disorders, e.g., dementia and Alzheimer's disease, CNS disorders, e.g., neuropathic pain and, in particular, oncological disorders. These compounds and formulations containing said compounds may be useful in the treatment or control of solid tumors, such as, for example, breast, colon, lung and prostate tumors.

The compounds of formula I as well as their salts have at least two asymmetric carbon atoms and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds claimed in the present invention (compounds of general formula 1) may be prepared by the general route shown in scheme 1.

Scheme 1: General route for preparation of 5-phenyl-1H-imidazole derivatives 1.

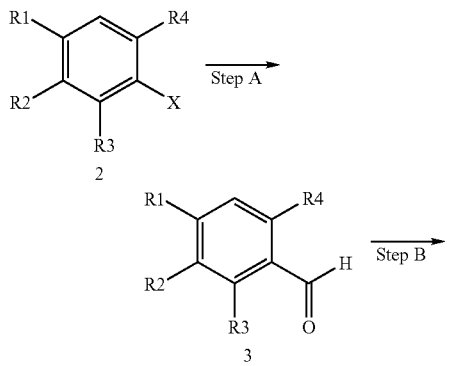

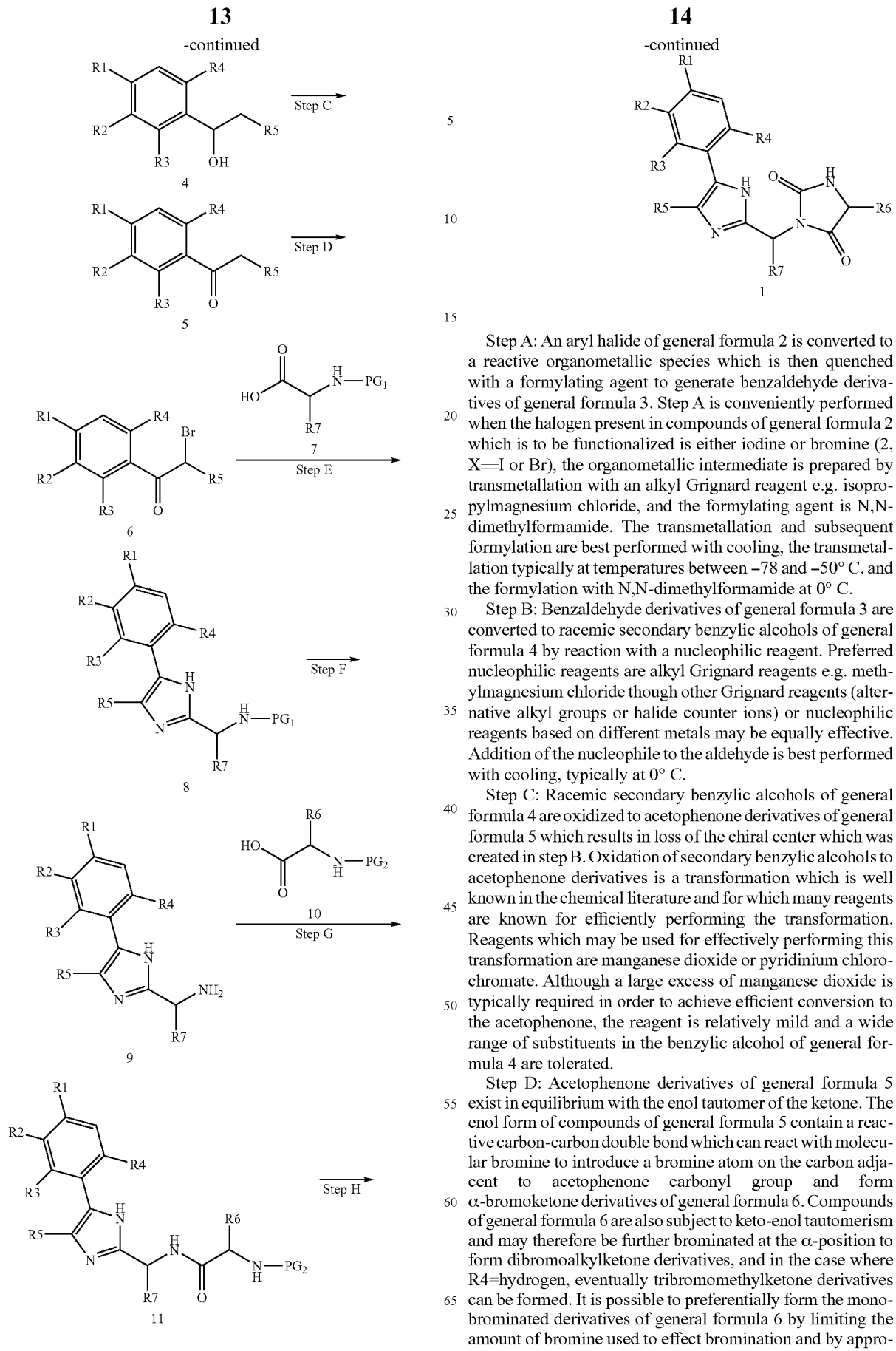

Step A: An aryl halide of general formula 2 is converted to a reactive organometallic species which is then quenched with a formylating agent to generate benzaldehyde derivatives of general formula 3. Step A is conveniently performed when the halogen present in compounds of general formula 2 which is to be functionalized is either iodine or bromine (2, X=I or Br), the organometallic intermediate is prepared by transmetallation with an alkyl Grignard reagent e.g. isopropylmagnesium chloride, and the formylating agent is N,N-dimethylformamide. The transmetallation and subsequent formylation are best performed with cooling, the transmetallation typically at temperatures between −78 and −50° C. and the formylation with N,N-dimethylformamide at 0° C.

Step B: Benzaldehyde derivatives of general formula 3 are converted to racemic secondary benzylic alcohols of general formula 4 by reaction with a nucleophilic reagent. Preferred nucleophilic reagents are alkyl Grignard reagents e.g. methylmagnesium chloride though other Grignard reagents (alternative alkyl groups or halide counter ions) or nucleophilic reagents based on different metals may be equally effective. Addition of the nucleophile to the aldehyde is best performed with cooling, typically at 0° C.

Step C: Racemic secondary benzylic alcohols of general formula 4 are oxidized to acetophenone derivatives of general formula 5 which results in loss of the chiral center which was created in step B. Oxidation of secondary benzylic alcohols to acetophenone derivatives is a transformation which is well known in the chemical literature and for which many reagents are known for efficiently performing the transformation. Reagents which may be used for effectively performing this transformation are manganese dioxide or pyridinium chlorochromate. Although a large excess of manganese dioxide is typically required in order to achieve efficient conversion to the acetophenone, the reagent is relatively mild and a wide range of substituents in the benzylic alcohol of general formula 4 are tolerated.

Step D: Acetophenone derivatives of general formula 5 exist in equilibrium with the enol tautomer of the ketone. The enol form of compounds of general formula 5 contain a reactive carbon-carbon double bond which can react with molecular bromine to introduce a bromine atom on the carbon adjacent to acetophenone carbonyl group and form α-bromoketone derivatives of general formula 6. Compounds of general formula 6 are also subject to keto-enol tautomerism and may therefore be further brominated at the α-position to form dibromoalkylketone derivatives, and in the case where R4=hydrogen, eventually tribromomethylketone derivatives can be formed. It is possible to preferentially form the monobrominated derivatives of general formula 6 by limiting the amount of bromine used to effect bromination and by appropriate control of other reaction conditions such as solvent, temperature and rate of addition of reagents.

Step E: α-Bromoketone derivatives of general formula 6 are reactive alkylating agents and may be used as the electrophilic components in nucleophilic substitution reactions. In step E an α-amino acid derivative of general formula 7 is first converted to the corresponding carboxylate salt by reaction with a metal carbonate salt. A preferred metal carbonate is cesium carbonate as the resulting cesium carboxylate salts are known to be effective nucleophiles. The cesium salts of α-amino acid derivative of general formula 7 react with α-bromoketone derivatives of general formula 6 to initially form ester derivatives by displacement of the reactive bromide in compounds of general formula 6 by the carboxylate salt in compounds of general formula 7. This reaction is facilitated in the presence of polar aprotic solvents, N,N-dimethylformamide being an example of one such preferred solvent. Following isolation, the intermediate ester derivatives can be converted into imidazole derivatives of general formula 8 by heating in the presence of ammonium acetate. Heating with microwave irradiation is a particularly efficient and rapid method of forming imidazole derivatives of general formula 8 from the initially formed ester derivatives formed in this step. Alternative methods of forming the imidazole ring, such as heating in an inert solvent such as xylene with azeotropic removal of water to drive the reaction to completion may also be employed to form the imidazole derivatives of general formula 8 from the initially formed ester derivatives.

Step E is most conveniently performed on an α-amino acid derivative of general formula 7 which bears a protecting group ($PG_1$) on the α-amine nitrogen. A suitable choice for protecting group PG1 is one which renders the α-amine nitrogen inert to the reaction conditions employed during step E but which may be removed during step F of the synthetic sequence without causing undesired modifications to the rest of the compound when exposed to the conditions required for the removal of the protecting group. Preferred choices for protecting group $PG_1$ may be made by reference to organic chemistry text books (e.g. Greene's Protective Groups in Organic Synthesis Fourth Edition., Peter G. M. Wuts and Theodora W. Greene, ISBN 0-471-69754-0), the original chemistry literature or would be known to one knowledgeable in the art of organic synthesis. In particular carbamate based protecting groups, e.g. tert-butyloxycarbonyl is preferred when no acid labile functional groups are present elsewhere in the molecule but other amine protecting groups may also be effective.

In the case where compounds of general formula 7 contain a chiral center at the α-carbon, the preferred stereochemistry is S.

Step F: This step in the synthetic sequence entails the removal of protecting group PG1 from compounds of general formula 8 to form free amine containing compounds of general formula 9 in preparation for subsequent elaboration. Choice of protecting group for PG1 and conditions to best achieve its removal may be made by reference to standard organic chemistry text books (as cited in step E), the original chemistry literature or would be known to one knowledgeable in the art of organic synthesis. This choice is influenced by what other potentially reactive functional groups are present in compounds of general formula 8 and the requirement of avoiding undesired reactions elsewhere in the starting material or product of the reaction, compounds of general formulae 8 and 9 respectively. In the case where the amine protecting group PG1 present in compounds of general formula 8 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the amine of general formula 9, from which the free amine of general formula 9 can be liberated after treatment with base.

Step G: Compounds of general formula 11 are obtained by combining amines of general formula 9 with a compound containing an α-amino acid functional group of general formula 10. Step G is most conveniently performed on compounds of general formula 10 which contain an α-amino acid which bears a protecting group ($PG_2$) on the α-amine nitrogen. The criteria for choice of the protecting group PG2 are the same as described for the choice of protecting group PG1 in step E. In particular carbamate based protecting groups, e.g. tert-butyloxycarbonyl is preferred when no acid labile functional groups are present elsewhere in the molecule but other amine protecting groups may also be effective.

In the case where compounds of general formula 10 contain a chiral center at the α-carbon, the preferred stereochemistry is R.

Step H: Compounds of general formula 1 as are claimed in the present invention can be obtained from compounds of general formula 11 by removal of protecting group PG2 and cyclization of the intermediate amine to form a hydantoin ring. Choice of protecting group PG2 and conditions to best achieve its removal may be made by reference to standard organic chemistry text books (as described in step E), the original chemistry literature or would be known to one knowledgeable in the art of organic synthesis. This choice is influenced by what other potentially reactive functional groups are present in compounds of general formula 11 and the need to avoid undesired reactions elsewhere in the starting material of general formula 11 or the intermediate amine which is liberated from the deprotection. In the case where the amine protecting group PG2 present in compounds of general formula 11 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the intermediate amine, from which the free amine can be liberated after treatment with base.

Compounds of general formula 1 can be obtained from the intermediate amine obtained by removal of protecting group PG2 by cyclization in the presence of phosgene or equivalent reagent, i.e. a carbonyl group directly attached to two displaceable groups. A preferred reagent for effecting the cyclization to compounds of general formula 1 is trichloromethyl chloroformate which functions in the reaction mixture as two equivalents of phosgene. Cyclization with trichloromethyl chloroformate to give compounds of general formula 1 is generally rapid and is typically performed at low temperature (<0° C.) and in the presence of a carefully controlled amount of base to neutralize the hydrogen chloride formed during the cyclization but to avoid unnecessary isomerization of the potentially labile chiral center on the newly formed hydantoin ring.

Another preferred reagent for effecting cyclization to compounds of general formula 1 from the amine intermediates obtained by deprotection of compounds of general formula 11 is bis-pentafluorophenyl carbonate. When bis-pentafluorophenyl carbonate is used to effect cyclization, a pentafluorophenyl carbamate is initially formed which subsequently cyclizes to compounds of general formula 1. For cyclization to occur at a useful rate at between 0° C. and ambient temperature the intermediate pentafluorophenyl carbamate may require treatment with an amine base e.g. diisopropylethylamine.

It will be apparent to one skilled in the art of organic synthesis that the product of step C, acetophenone of general formula 5, belongs to a class of compounds well known in the field of organic chemistry. There are therefore many alternative methods known in the organic chemistry literature for the synthesis of acetophenone derivatives of general formula 5 which are either generally applicable to the class or to more specific examples from within this chemical class. One alternative route for the preparation of acetophenone derivatives of general formula 5 is shown in scheme 2. In addition several acetophenone derivatives of general formula 5 are commercially available.

Scheme 2: Alternative route for preparation of acetophenone derivatives 5.

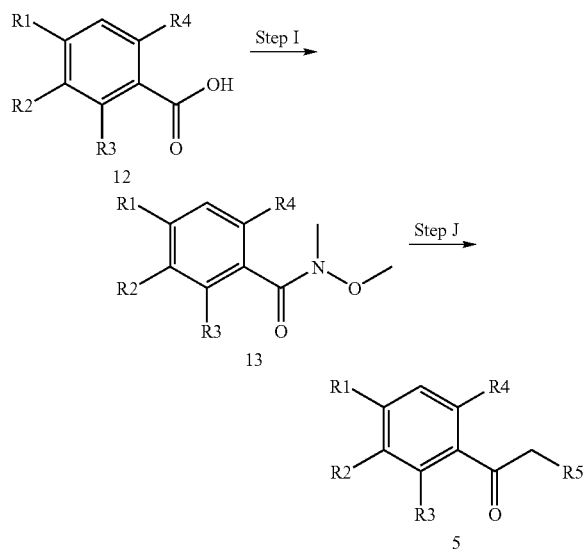

Step I: Benzoic acid derivatives of general formula 12 are condensed with N,O-dimethylhydroxylamine to give N-methoxy-N-methyl amides of general formula 13. One convenient way of performing this condensation is by the use of a peptide coupling reagent such as the uronium based reagent O-benzotriazol-1-yl-N,N, N',N'-tetramethyluronium hexafluororophosphate. Alternative peptide coupling reagents may be equally effective in performing this condensation. In addition it may be possible to perform this condensation by prior activation of the carboxylic acid functional group in compounds of general formula 12 to form an active acylating agent with which to acylate N,O-dimethylhydroxylamine. Typical reactive acylating agents which may be employed include acyl halides and acid anhydrides though additional choices for acylating agents may also be suitable for use in step 1 and would be apparent to one knowledgeable in the art of organic synthesis.

Step J: N-Methoxy-N-methyl amides of general formula 13 when treated with nucleophilic organometallic reagents cleanly form acetophenone derivatives of general formula 5 with little or no contamination with the tertiary benzylic alcohol arising from addition of the nucleophilic organometallic reagent to the carbonyl of the acetophenone of general formula 5. Preferred nucleophilic organometallic reagents for use in this step are alkyl Grignard reagents e.g. methylmagnesium chloride.

It will be apparent to one knowledgeable in the art of organic synthesis that when one or more of the substituents labeled R1 through R7 in the compounds shown in schemes 1 and 2 are in and of themselves chemically reactive groups, or contains chemically reactive groups, then additional modification of the compounds of general formula 1 through 11 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in schemes 1 and 2. Alternatively, if the newly elaborated group is not chemically inert or can interfere with the remaining steps in the synthetic sequence it may be necessary to temporarily mask the reactive functional group with an appropriate protecting group. If a protecting group is introduced which is not required in the final compound of general structure 1 then it may either be removed under the conditions remaining in the synthetic sequence shown in schemes 1 and 2 or by introduction of an additional deprotection step into the synthetic sequence depending upon the nature of the protecting group employed.

It will also be apparent to one skilled in the art of organic synthesis that final choice of reagents and reaction conditions in the steps outlined above and shown in schemes 1 and 2 will to some extent be dependent upon the exact nature of the variable substituents R1 to R7 present. Ultimate selection of reagents and reaction conditions to best perform the outlined transformations can be performed by one skilled in the art of organic synthesis by reference to the examples which are contained herein, by reference to published literature examples or if needs be by empirical observation and optimization.

The reaction conditions for the above reactions can vary to a certain extent.

Methods to perform the above described reactions and processes would be apparent to those of ordinary skill in the art based on the present disclosure, or can be deduced in analogy from the examples. Starting materials are commercially available or can be made by methods analogous to those described in the Examples.

Compound $IC_{50}$ Determination in MEK Cascade Assay

The evaluation of the compounds as MEK inhibitor was performed in a bead-based FP assay termed IMAP assay with MEK cascade components. In brief, the assay was performed in a reaction solution containing 10 mM HEPES, pH 7.0, 10 mM $MgCl_2$, 50 mM NaCl, 0.1 mM $NaVO_4$, and 1 m M DTT in the presence of 50 μm ATP, 1 nM c-RAF, 22.5 nM MEK, 90.5 nM ERK, and 0.5 μM FITC-labeled ERK (FITC-Aca-Ala-Ala-Ala-Thr-Gly-Pro-Leu-Ser-Pro-Gly-Pro-Phe-Ala-NH2 (SEQ ID NO: 1)). C-RAF, MEK, ERK and the ERK peptide substrates were added sequentially into the reaction buffer. Activated c-Raf phosphorylates MEK, activated MEK phosphorylates ERK, and subsequently activated ERK phosphorylates its peptide substrate. The FITC-labeled peptide substrates, when phosphorylated by the kinase, bind to nanoparticles derivatized with trivalent metal cations through a metal-phospholigand interaction. The result of this bound fluoresceinated phosphorylated product is an increase in polarization signal caused by a decrease in the molecular mobility of the bound product. Ten-point serial dilutions of the compounds were added into the MEK cascade assays before mixing with ERK and ERK peptide substrates. The reaction mixture was incubated for 1 hr at 37° C. The reaction was stopped by transferring 2 μl of reaction mixture to 30 μl of 1:400 IMAP beads buffer, then was incubated overnight at room temperature for binding of IMAP beads. The IMAP assay was performed in a 384-well plate format. The changes in fluorescence polarization were measured by LJL instrument at 485 nm for excitation and 530 for emission. Polarization value (MP) was calculated as the following:

$$(MP) = 1000(\text{intensity vertical} - \text{intensity horizontal}) / (\text{intensity vertical} + \text{intensity horizontal}).$$

Compound $IC_{50}$ values are determined from inter-plate triplicate sets of data. Data were analyzed by using XLfit4 and fitting data to 4 Parameter Logistic Model (Sigmoidal Dose-Response Model), equation $Y=(A+((B-A)/(1+((C/x)^D))))$, where A and B are enzyme activity in the presence of no and infinite inhibitor compound respectively, C is the $IC_{50}$ and D is the hill constant of the compound response.

The compounds of formula I set forth in the Examples below exhibit $IC_{50}$ values of less than 5 micromolar in the above assay.

The following examples shall illustrate preferred embodiments of the present invention but are not intended to limit the scope of the invention.

Example 1

(R)-3-{(1S,2S)-1-[4-Chloro-5-(2-fluoro-4-iodo-phenyl)-1H-imidazol-2-yl]-2-phenyl-propyl}-5-[4-(2-hydroxy-ethoxy)-phenyl]-imidazolidine-2,4-dione

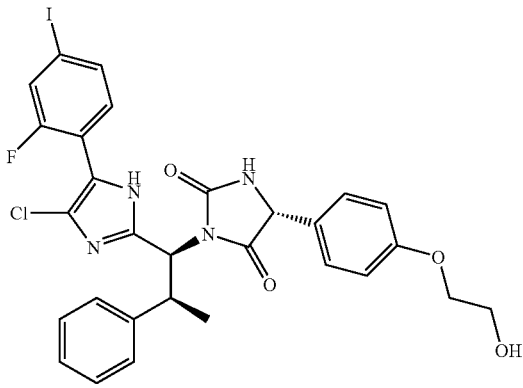

Step 1-A: A solution of 2-fluoro-1,4-diiodo-benzene (804 mg, 2.31 mmol) in tetrahydrofuran (8 mL) was cooled to −78° C. (external) and a 2.0 M solution of isopropylmagnesium chloride in tetrahydrofuran (1.44 mL, 2.89 mmol) added via syringe. The resulting mixture was stirred for 30 minutes while allowing the temperature of the cooling bath to rise to −50° C. The reaction mixture was then immersed in an ice/water bath and anhydrous N,N-dimethylformamide (425 µL, 5.78 mmol) was added by syringe to the reaction mixture. The reaction was stirred at 0° C. for 10 minutes, then at room temperature for 5 minutes. Thin layer chromatography (TLC) indicated the reaction to be complete. The mixture was diluted with saturated aqueous ammonium chloride solution (8 mL) and extracted with diethylether (2×20 mL). The combined organic layers were dried over sodium sulfate and concentrated in vacuo. The resulting residue was purified by chromatography over silica gel gradient eluted with 0 to 15% v/v ethyl acetate/hexanes to give 2-fluoro-4-iodo-benzaldehyde as a fluffy-white solid (389 mg, 67%).

Step 1-B: To a solution of 2-fluoro-4-iodo-benzaldehyde (17.40 g, 69.60 mmol) in anhydrous tetrahydrofuran (300 mL) at −10° C. under an atmosphere of nitrogen was added 3.0 M methylmagnesium chloride in tetrahydrofuran (27.84 mL, 83.52 mmol) via syringe at such a rate as to maintain the temperature of the reaction mixture below 0° C. The reaction was stirred for 30 minutes while warming to room temperature. Saturated aqueous ammonium chloride solution was added and the mixture was diluted with ethyl acetate (200 mL). The organic layer was separated and the aqueous layer was extracted with ethyl acetate (2×50 mL). The organic extracts were combined, washed with water (1×50 mL), brine, dried over sodium sulfate, filtered and concentrated in vacuo. The crude product was purified by chromatography over silica gel gradient eluted with 15 to 40% v/v ethyl acetate/hexanes to give 1-(2-fluoro-4-iodo-phenyl)-ethanol (15.50 g, 84%).

Step 1-C: To a solution of 1-(2-fluoro-4-iodo-phenyl)-ethanol (15.50 g, 58.26 mmol) in dichloromethane (250 mL) was added manganese dioxide (101.26 g, 1.17 mole) and the reaction mixture was heated to reflux for 24 hours. The reaction mixture was cooled, filtered through a pad of celite coated with a thin layer of silica gel and concentrated in vacuo to give 1-(2-fluoro-4-iodo-phenyl)-ethanone (14.04 g, 91%).

Step 1-D: A solution of bromine (2.74 mL, 53.18 mmol) in acetic acid (30 mL) was added dropwise to a solution of 1-(2-fluoro-4-iodo-phenyl)-ethanone (14.04 g, 53.18 mmol) in acetic acid (200 mL) at room temperature under an atmosphere of nitrogen and then stirred for 24 hours. The reaction was concentrated to near dryness in vacuo, diluted with ethyl acetate (200 mL) and basified with saturated aqueous sodium carbonate solution. The organic layer was washed with brine, dried over sodium sulfate, filtered through a pad of silica gel and concentrated in vacuo to give 2-bromo-1-(2-fluoro-4-iodo-phenyl)-ethanone (18.10 g, 99%).

Step 1-E: To a solution of (2S,3S)-2-tert-butoxycarbonylamino-3-phenyl-butyric acid (1.6 g, 5.73 mmol) in 1:1 v/v ethanol/water (50 mL) was added cesium carbonate (933 mg, 2.86 mmol) at room temperature and the resulting solution was stirred for 30 minutes. The reaction was concentrated in vacuo and the residue was dried by azeotropic distillation in vacuo with ethanol (2×50 mL) to remove trace amount of water. The cesium salt was dissolved in N,N-dimethylformamide (20 mL) followed by the addition of 2-bromo-1-(2-fluoro-4-iodo-phenyl)-ethanone (1.96 g, 5.73 mmol) and reaction was stirred for 24 hours at room temperature. The precipitated cesium bromide was removed by filtration through celite and the filtrate was concentrated in vacuo. To a solution of the crude product in toluene (12 mL) was added ammonium acetate (4.42 g, 5.73 mmol) and the mixture was heated by microwave irradiation to 150° C. for 25 minutes. The cooled reaction was poured into ethyl acetate (50 mL), washed with water (2×20 mL), brine, dried over sodium sulfate, filtered and concentrated in vacuo. The crude product was purified by chromatography over silica gel gradient eluted with 10 to 30% v/v ethyl acetate/hexanes to give {(1S,2S)-1-[5-(2-fluoro-4-iodo-phenyl)-1H-imidazol-2-yl]-2-phenyl-propyl}-carbamic acid tert-butyl ester (1.60 g, 55%). HR-MS: calcd for $C_{23}H_{25}FIN_3O_2$ [M+H⁺] 522.1048. Found 522.1045.

Step 1-F: To a solution of {(1S,2S)-1-[5-(2-fluoro-4-iodo-phenyl)-1H-imidazol-2-yl]-2-phenyl-propyl}-carbamic acid tert-butyl ester (1.10 g, 2.11 mmol) in 10:1 v/v acetonitrile/tetrahydrofuran (20 mL) under an atmosphere of nitrogen was added N-chlorosuccinimide (352 mg, 2.64 mmol) and the mixture was refluxed for 24 hours. The reaction was concentrated in vacuo, diluted with ethyl acetate (60 mL) and washed with saturated sodium hydrogen carbonate solution. The organic layer was washed with brine, dried over sodium sulfate, filtered and concentrated in vacuo. To a solution of the crude product in dichloromethane (20 mL) under an atmosphere of nitrogen was added trifluoroacetic acid (6 mL) and the mixture was stirred for one hour. The reaction mixture was concentrated in vacuo then basified with saturated aqueous sodium hydrogen carbonate solution and extracted with ethyl acetate (2×50 mL). The organic extracts were combined, washed with brine, dried over sodium sulfate, filtered and concentrated in vacuo to give (1S,2S)-1-[4-chloro-5-(2-fluoro-4-iodo-phenyl)-1H-imidazol-2-yl]-2-phenyl-propylamine which was used in the subsequent step without further purification (860 mg, 89%).

Step 1-G: To a solution of (1S,2S)-1-[4-chloro-5-(2-fluoro-4-iodo-phenyl)-1H-imidazol-2-yl]-2-phenyl-propylamine (550 mg, 1.21 mmol) in N,N-dimethylformamide (12 mL) was added (R)-tert-butoxycarbonylamino-[4-(2-tert-butoxy-ethoxy)-phenyl]-acetic acid (532 mg, 1.45 mmol) (prepared as described below), N,N-diisopropylethylamine (841 µL, 4.83 mmol), N-hydroxybenzotriazole (212 mg, 1.57 mmol) and O-benzotriazol-1-yl-N,N,N'N'-tetramethyluronium hexafluorophosphate (595 mg, 1.57 mmol). The mixture was stirred under an atmosphere of nitrogen at room temperature for 3 hours. The reaction was poured into water (20 mL) and extracted with ethyl acetate (2×25 mL). The organic extracts were combined, washed with brine, dried over sodium sulfate, filtered and concentrated in vacuo. The crude product was purified by chromatography over silica gel gradient eluted with 20 to 50% v/v ethyl acetate/hexanes to give ((R)-[4-(2-tert-butoxy-ethoxy)-phenyl]-{(1S,2S)-1-[4-chloro-5-(2-fluoro-4-iodo-phenyl)-1H-imidazol-2-yl]-2-phenyl-propylcarbamoyl}-methyl)-carbamic acid tert-butyl ester (440 mg, 45%).

Preparation of (R)-tert-butoxycarbonylamino-[4-(2-tert-butoxy-ethoxy)-phenyl]-acetic acid: A 3 liter, 3-necked round bottom flask equipped with a mechanical stirrer, temperature probe, addition funnel and nitrogen bubbler was charged with (R)-tert-butoxycarbonylamino-(4-hydroxy-phenyl)-acetic acid (67.9 g, 254 mmol) (Salituro, G. M.; Townsend, C. A. J. Am. Chem. Soc. 1990, 112, 760-770) in 1-methyl-pyrrolidin-2-one (225 mL) and then cooled to an internal reaction mixture temperature of 2° C. Aqueous sodium hydroxide (50% by weight) (43.2 g, 0.541 mol) was added over 10 minutes while maintaining the internal reaction mixture temperature below 14° C. The brown solution was stirred for 1 hour while maintaining the internal reaction mixture temperature below 10° C. 2-(2-Iodo-ethoxy)-2-methyl-propane (87.1 g, 382 mmol) containing 2-methoxy-2-methyl-propane (29 mL) was added over 10 minutes while maintaining the internal reaction mixture temperature between 3 and 5° C. After stirring the green colored reaction mixture at ambient temperature for 16 hours. HPLC analysis indicated approximately 20% of unreacted (R)-tert-butoxycarbonylamino-(4-hydroxy-phenyl)-acetic acid present. The reaction mixture was cooled to an internal temperature of 5° C. and additional 2-(2-iodo-ethoxy)-2-methyl-propane (12.1 g, 53.1 mmol) containing 2-methoxy-2-methyl-propane (4 mL) was added over approximately 2 minutes while maintaining an internal reaction mixture temperature of between 5 and 6° C., followed by aqueous sodium hydroxide (50% by weight) (9 g, 113 mmol). The reaction mixture was allowed to warm and stirred at ambient temperature for 2 days. The reaction mixture was cooled to 4° C. and water (1.5 L) added over 1.5 hours while maintaining the internal reaction mixture temperature below 10° C. 2-Methoxy-2-methyl-propane (1.5 L) was added, the reaction mixture partitioned between the 2 phases and the layers separated. The yellow aqueous layer was cooled to 4° C. and 6 N aqueous hydrochloric acid (450 mL, 2.7 mol) added over 5 minutes to form a white precipitate. The aqueous mixture was then extracted with ethyl acetate (2×1 L). The combined ethyl acetate extracts were washed with an aqueous solution of ammonium chloride (15% by weight) (175 mL) followed by an aqueous solution of sodium chloride (20% by weight) (175 mL). The reaction mixture was then concentrated under reduced pressure to give (R)-tert-butoxycarbonylamino-[4-(2-tert-butoxy-ethoxy)-phenyl]-acetic acid as a yellow oil which was suitable for further use without additional purification. HR-MS: calcd for $C_{37}H_{43}ClFIN_4O_4$ [M+H$^+$] 805.2024. Found 805.2017.

Step 1-H: Hydrogen chloride gas was bubbled into a solution of ((R)-[4-(2-tert-butoxy-ethoxy)-phenyl]-{(1S,2S)-1-[4-chloro-5-(2-fluoro-4-iodo-phenyl)-1H-imidazol-2-yl]-2-phenyl-propylcarbamoyl}-methyl)-carbamic acid tert-butyl ester (440 mg, 0.55 mmol) in dioxane for 15 minutes at room temperature and the resulting mixture was allowed to stir under an atmosphere of nitrogen for 3 hours. The reaction was concentrated in vacuo and the residue was dissolved in tetrahydrofuran (15 mL) containing triethylamine (609 µL, 4.37 mmol). Chlorotrimethylsilane (416 µL, 3.28 mmol) was added via syringe at room temperature and the resulting mixture was allowed to stir under an atmosphere of nitrogen for one hour. The reaction was poured into water (10 mL) and extracted with ethyl acetate (2×25 mL). The organic extracts were combined, washed with brine, dried over sodium sulfate, filtered and concentrated in vacuo. The crude product, dissolved in tetrahydrofuran (5 mL) containing N,N-diisopropylethylamine was added via an addition funnel to diphosgene (46 µL, 0.38 mmol) in 1:1 v/v toluene/tetrahydrofuran (5 mL) at −78° C. under an atmosphere of nitrogen with stirring. The reaction was allowed to warm to 10° C. then quenched with ice/water (5 mL) and stirred for 2 minutes. The mixture was acidified with 1.0 N aqueous hydrochloric acid solution (10 mL), stirred for 5 minutes then extracted with ethyl acetate (2×25 mL). The organic extracts were combined, washed with water (2×10 mL), brine, dried over sodium sulfate, filtered and concentrated in vacuo. The crude product was purified by chromatography over silica gel gradient eluted with 50 to 80% v/v ethyl acetate/hexanes to give (R)-3-{(1S,2S)-1-[4-chloro-5-(2-fluoro-4-iodo-phenyl)-1H-imidazol-2-yl]-2-phenyl-propyl}-5-[4-(2-hydroxy-ethoxy)-phenyl]-imidazolidine-2,4-dione (229 mg, 62%). HR-MS: calcd for $C_{29}H_{25}ClFIN_4O_4$ [M+H$^+$] 675.0666. Found 675.0660.

The following examples may be prepared by reference to the procedure outlined in example 1 with any changes to reactants, reagents or reaction conditions as noted in each example.

Example 2

(R)-5-[4-(2-Hydroxy-ethoxy)-phenyl]-3-{(S)-1-[5-(4-iodo-phenyl)-1H-imidazol-2-yl]-2-phenyl-ethyl}-imidazolidine-2,4-dione

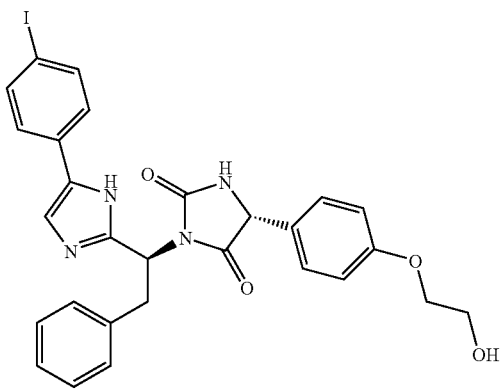

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 2-D; (iii) (S)-2-tert-butoxycarbonylamino-3-phenyl-propionic acid was used in place of (2S,3S)-2-tert-butoxycarbonylamino-3-phenyl-butyric acid in step 2-E; and (iv) chlorination of the 5-position of the imidazole ring with N-chlorosuccinimide in step 2-F was omitted. HR-MS: calcd for $C_{28}H_{25}IN_4O_4$ [M+H$^+$] 609.0993. Found 609.0991.

Example 3

(R)-5-[4-(2-Hydroxy-ethoxy)-phenyl]-3-{(1S,2S)-1-[5-(4-iodo-phenyl)-1H-imidazol-2-yl]-2-phenyl-propyl}-imidazolidine-2,4-dione

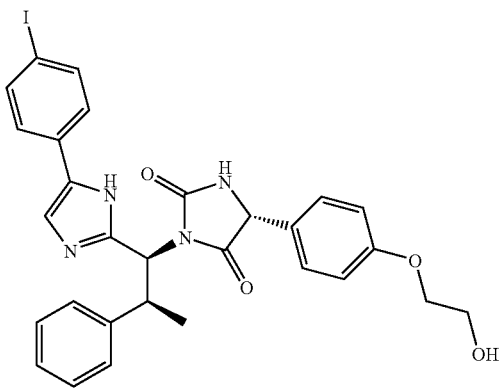

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 3-D; and (iii) chlorination of the 5-position of the imidazole ring with N-chlorosuccinimide in step 3-F was omitted. HR-MS: calcd for $C_{29}H_{27}IN_4O_4$ [M+H$^+$] 623.1150. Found 623.1153.

Example 4

(R)-5-[4-(2-Hydroxy-ethoxy)-phenyl]-3-{(S)-1-[5-(4-iodo-phenyl)-1H-imidazol-2-yl]-2-methyl-propyl}-imidazolidine-2,4-dione

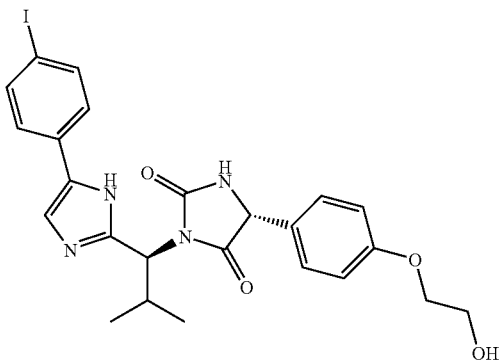

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 4-D; (iii) (S)-2-tert-butoxycarbonylamino-3-methyl-butyric acid was used in place of (2S,3S)-2-tert-butoxycarbonylamino-3-phenyl-butyric acid in step 4-E; and (iv) chlorination of the 5-position of the imidazole ring with N-chlorosuccinimide in step 4-F was omitted. LC-MS: calcd for $C_{24}H_{25}IN_4O_4$ [M+H$^+$] 561. Found 561.

Example 5

(R)-5-[4-(2-Hydroxy-ethoxy)-phenyl]-3-{(1R,2R)-1-[5-(4-iodo-phenyl)-1H-imidazol-2-yl]-2-methoxy-propyl}-imidazolidine-2,4-dione

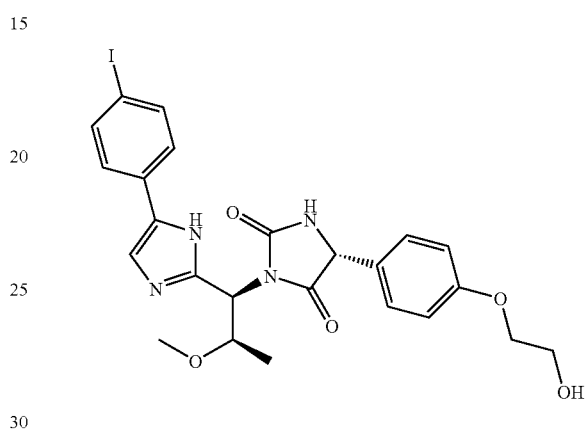

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 5-D; (iii) (2S,3R)-2-tert-butoxycarbonylamino-3-methoxy-butyric acid was used in place of (2S,3S)-2-tert-butoxycarbonylamino-3-phenyl-butyric acid in step 5-E; and (iv) chlorination of the 5-position of the imidazole ring with N-chlorosuccinimide in step 5-F was omitted. LC-MS: calcd for $C_{24}H_{25}IN_4O_5$ [M+H$^+$] 577. Found 577.

Example 6

2-[4-((R)-1-{(1S,2S)-1-[5-(4-Bromo-2-chloro-phenyl)-1H-imidazol-2-yl]-2-phenyl-propyl}-2,5-dioxo-imidazolidin-4-yl)-phenoxy]-N,N-dimethyl-acetamide

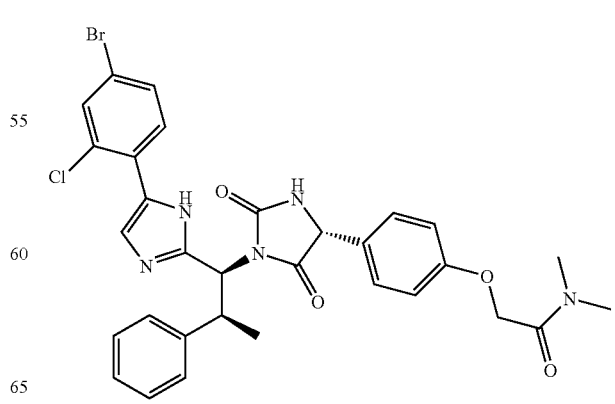

Prepared by the same method as described in example 1 except that (i) steps A, B and C were omitted; (ii) 1-(4-bromo-2-chloro-phenyl)-ethanone (prepared as described below in steps 6-I and 6-J) was used instead of 1-(2-fluoro-4-iodo-phenyl)-ethanone in step 6-D; (iii) chlorination of the 5-position of the imidazole ring with N-chlorosuccinimide in step 6-F was omitted; (iv) (R)-tert-butoxycarbonylamino-(4-dimethylcarbamoylmethoxy-phenyl)-acetic acid (prepared as described below) was used in place of (R)-tert-butoxycarbonylamino-[4-(2-tert-butoxy-ethoxy)-phenyl]-acetic acid in step 6-G; and (v) silylation with chlorotrimethylsilane and triethylamine in step 6-H was omitted.

Step 6-I: A solution of 4-bromo-2-chloro-benzoic acid (3.30 g, 14 mmol), 2-chloro-4,6-dimethoxy-1,3,5-triazine (2.44 g, 14 mmol) and N-methylmorpholine in tetrahydrofuran were stirred for 2 hours at room temperature. N,O-Dimethylhydroxyamine hydrochloride (1.37 g, 14 mmol) and triethylamine (2 mL, 14 mmol) were added and the resulting mixture was stirred for 3 days. The reaction mixture was evaporated and ethyl acetate was added. The mixture was washed with 1N aqueous hydrochloric acid, water, brine, dried over sodium sulfate, filtered and concentrated in vacuo to give 4-bromo-2-chloro-N-methoxy-N-methyl-benzamide (3.52 g, 91%).

Step 6-J: Methyl magnesium bromide (44 mL, 61.6 mmol, 1.4 M in tetrahydrofuran) was added to tetrahydrofuran (50 mL) at −78° C. (4-Bromo-2-chloro-N-methoxy-N-methyl-benzamide (3.52 g, 12.7 mmol) (from step 6-I) in tetrahydrofuran (30 mL) was added. The mixture was stirred at −78° C. for 45 minutes and then at room temperature for 1.5 hours. The reaction mixture was poured into ice water and saturated aqueous ammonium chloride was added. The mixture was extracted with ethyl acetate (3 times) and the combined organic extracts were washed with brine, dried over sodium sulfate, filtered and concentrated in vacuo. The crude product was recrystallized from ethyl acetate/hexanes to give 1-(4-bromo-2-chloro-phenyl)-ethanone as a white solid (1.1 g, 37%).

Preparation of (R)-tert-butoxycarbonyl amino-(4-dimethylcarbamoyl methoxy-phenyl)-acetic acid: Prepared by the same method as described in example 1, step 1-G for the preparation of (R)-tert-butoxycarbonylamino-[4-(2-tert-butoxy-ethoxy)-phenyl]-acetic acid except that 2-chloro-N,N-dimethyl-acetamide was used in place of 2-(2-iodo-ethoxy)-2-methyl-propane and the preparation performed as follows: Sodium hydride (0.88 g, 22 mmol, 60% in mineral oil) was added portionwise to a stirred and cooled (ice bath) solution of (S)-tert-butoxycarbonylamino-(4-hydroxy-phenyl)-acetic acid (2.67 g, 10 mmol) in N,N-dimethylformamide (50 mL). 2-Chloro-N,N-dimethyl-acetamide (1.22 g, 10 mmol) was added and the mixture was stirred for three days. The mixture was diluted with water and extracted with ether. The aqueous layer was acidified to pH=2 and extracted with ethyl acetate. The combined organic extracts were washed with water, brine, dried over sodium sulfate, filtered and following evaporation of the solvents (S)-tert-butoxycarbonylamino-(4-dimethylcarbamoylmethoxy-phenyl)-acetic acid was obtained as a white solid (2.68 g, 76%). HR-MS: calcd for $C_{31}H_{29}BrClN_5O_4$ [M+H$^+$] 650.1164. Found 650.1166.

Example 7

2-[4-((R)-1-{(1S,2S)-1-[5-(4-Chloro-2-fluoro-phenyl)-1H-imidazol-2-yl]-2-phenyl-propyl}-2,5-dioxo-imidazolidin-4-yl)-phenoxy]-N,N-dimethyl-acetamide

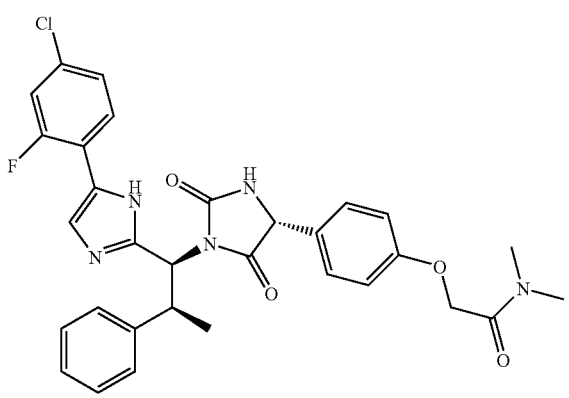

Prepared by the same method as described in example 1 except that (i) steps A, B and C were omitted; (ii) commercially available 1-(4-chloro-2-fluoro-phenyl)-ethanone was used in place of 1-(2-fluoro-4-iodo-phenyl)-ethanone in step 7-D (ii) chlorination of the 5-position of the imidazole ring with N-chlorosuccinimide in step 7-F was omitted; (iii) (R)-tert-butoxycarbonylamino-(4-dimethylcarbamoylmethoxy-phenyl)-acetic acid (prepared as described in example 6) was used in place of (R)-tert-butoxycarbonylamino-[4-(2-tert-butoxy-ethoxy)-phenyl]-acetic acid in step 7-G; and (iv) silylation with chlorotrimethylsilane and triethylamine in step 7-H was omitted. HR-MS: calcd for $C_{31}H_{29}ClFN_5O_4$ [M+H$^+$] 590.1965. Found 590.1964.

Example 8

((R)-1-{(1S,2S)-1-[5-(4-Iodo-phenyl)-1H-imidazol-2-yl]-2-phenyl-propyl}-2,5-dioxo-imidazolidin-4-yl)-acetic Acid; Hydrochloride Salt

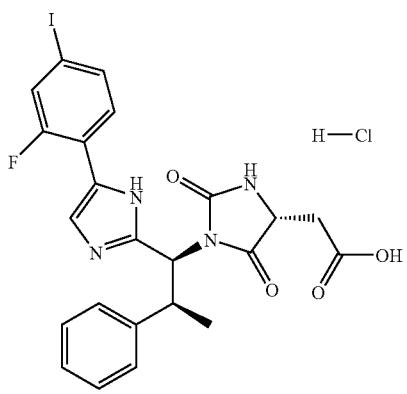

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 8-D; (iii) chlorination of the 5-position of the imidazole ring with N-chlorosuccinimide in step 8-F was omitted; (iv) commercially available (R)-2-(9H-fluoren-9-ylmethoxycarbonylamino)-succinic acid 4-tert-butyl ester was used in place of (R)-tert-butoxycarbonylamino-[4-(2-tert-butoxy-ethoxy)-phenyl]-acetic acid and O-benzotriazol-1-yl-N,N,N',N'-bis(tetramethylene)uronium hexafluororophosphate was used as the coupling reagent in place of O-benzotriazol-1-yl-N,N,N',N'-tetramethyluronium hexafluororophosphate in step 8-G; and (v) step H was replaced by steps 8-K to 8-M described below.

Step 8-K: To a solution of (R)-3-(9H-fluoren-9-ylmethoxycarbonylamino)-N-{(1S,2S)-1-[5-(4-iodo-phenyl)-1H-imidazol-2-yl]-2-phenyl-propyl}-succinamic acid tert-butyl ester (1.5 g, 1.88 mmol) (from step 8-G) in methylene chloride (30 mL) was added piperidine (6 mL). The mixture was stirred at room temperature for 1 hour. The reaction mixture was concentrated in vacuo and the residue was purified by chromatography over silica gel gradient eluted from 100% methylene chloride to 10% v/v methanol/methylene chloride in 30 minutes to give ((R)-3-amino-N-{(1S,2S)-1-[5-(4-iodo-phenyl)-1H-imidazol-2-yl]-2-phenyl-propyl}-succinamic acid tert-butyl ester (0.93 g, 86%). LC-MS: calcd for $C_{26}H_{31}IN_4O_3$ [M+H$^+$] 575. Found 575.

Step 8-L: A solution of ((R)-3-amino-N-{(1S,2S)-1-[5-(4-iodo-phenyl)-1H-imidazol-2-yl]-2-phenyl-propyl}-succinamic acid tert-butyl ester (400 mg, 0.7 mmol) in tetrahydrofuran (3 mL) containing N,N-diisopropylethylamine (0.37 mL, 2.1 mmol) was added via an addition funnel to diphosgene (0.059 mL, 0.49 mmol) in a 1:1 v/v mixture of toluene/tetrahydrofuran (6 mL) at –40° C. under an atmosphere of nitrogen with stirring. The reaction was stirred at this temperature for 20 minutes and then allowed to warm to 10° C. before quenching with ice/water (5 mL). After stirring for 2 minutes the mixture was extracted with ethyl acetate (2×25 mL). The organic extracts were combined, washed with water (2×10 mL), brine, dried over sodium sulfate, filtered and concentrated in vacuo. The crude product was purified by chromatography over silica gel gradient eluted with 0 to 50% v/v ethyl acetate/hexanes to give ((R)-1-{(1S,2S)-1-[5-(4-iodo-phenyl)-1H-imidazol-2-yl]-2-phenyl-propyl}-2,5-dioxo-imidazolidin-4-yl)-acetic acid tert-butyl ester (120 mg, 29%). LC-MS: calcd for $C_{27}H_{29}IN_4O_4$ [M+H$^+$] 601. Found 601

Step 8-M: To ((R)-1-{(1S,2S)-1-[5-(4-iodo-phenyl)-1H-imidazol-2-yl]-2-phenyl-propyl}-2,5-dioxo-imidazolidin-4-yl)-acetic acid tert-butyl ester (120 mg, 0.2 mmol) was added 4 N hydrogen chloride in p-dioxane (2 mL, 0.8 mmol). The mixture was stirred at room temperature for 2 hours. The reaction mixture was concentrated in vacuo and hexane was added to form a precipitate. The solid was collected by filtration and dried to give ((R)-1-{(1S,2S)-1-[5-(4-iodo-phenyl)-1H-imidazol-2-yl]-2-phenyl-propyl}-2,5-dioxo-imidazolidin-4-yl)-acetic acid; hydrochloride salt as a light yellow solid (120 mg, 100%). LC-MS: calcd for $C_{23}H_{21}IN_4O_4$ [M+H$^+$] 545. Found 545.

Example 9

N-(2-Hydroxy-ethoxy)-2-((R)-1-{(1S,2S)-1-[5-(4-iodo-phenyl)-1H-imidazol-2-yl]-2-phenyl-propyl}-2,5-dioxo-imidazolidin-4-yl)-acetamide

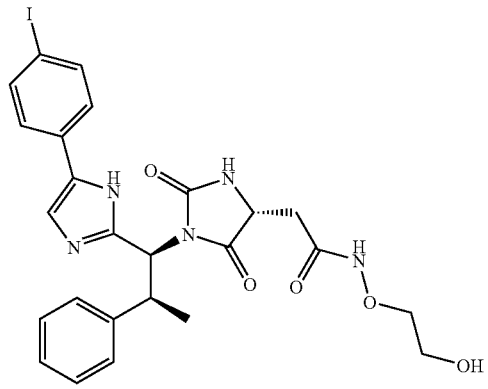

Step 9-N: To a solution of ((R)-1-{(1S,2S)-1-[5-(4-iodo-phenyl)-1H-imidazol-2-yl]-2-phenyl-propyl}-2,5-dioxo-imidazolidin-4-yl)-acetic acid; hydrochloride salt (114 mg, 0.21 mmol) (prepared as described in example 8), O-(2-vinyloxy-ethyl)-hydroxylamine (26 mg, 0.25 mmol) (prepared as described in WO 02/06213) and N,N-diisopropylethyl amine (0.11 mL, 0.63 mmol) in N,N-dimethylformamide (2 mL) was added O-benzotriazol-1-yl-N,N,N',N'-bis(tetramethylene)uronium hexafluororophosphate (110 mg, 0.25 mmol). The reaction mixture was stirred for 1 hour at room temperature then diluted with ethyl acetate and the organic layer washed successively with saturated aqueous sodium carbonate then brine, dried over sodium sulfate, filtered, concentrated and the residue purified by chromatography over silica gel eluted with ethyl acetate to give 2-((R)-1-{(1S,2S)-1-[5-(4-iodo-phenyl)-1H-imidazol-2-yl]-2-phenyl-propyl}-2,5-dioxo-imidazolidin-4-yl)-N-(2-vinyloxy-ethoxy)-acetamide (81 mg, 61%) as a solid. LC-MS: calcd for $C_{27}H_{28}IN_5O_5$ [M+H$^+$] 630. Found 630.

Step 9-O: To a solution of 2-((R)-1-{(1S,2S)-1-[5-(4-iodo-phenyl)-1H-imidazol-2-yl]-2-phenyl-propyl}-2,5-dioxo-imidazolidin-4-yl)-N-(2-vinyloxy-ethoxy)-acetamide (64 mg, 0.1 mmol) in methanol (3 mL) was added aqueous 1 N hydrochloric acid (3 mL). The mixture was stirred at room temperature for 3 hours. Saturated aqueous sodium carbonate solution (10 mL) was added and the reaction mixture was extracted with ethyl acetate (2×50 mL). The organic layers were successively washed with saturated aqueous sodium carbonate solution then brine, dried over sodium sulfate, filtered, concentrated and the residue purified by chromatography over silica gel gradient eluted from 100% methylene chloride up to 10% v/v methanol/methylene chloride during 30 minutes to give N-(2-hydroxy-ethoxy)-2-((R)-1-{(1S,2S)-1-[5-(4-iodo-phenyl)-1H-imidazol-2-yl]-2-phenyl-propyl}-2,5-dioxo-imidazolidin-4-yl)-acetamide as a white solid (42 mg, 61%). LC-MS: calcd for $C_{25}H_{26}IN_5O_5$ [M+H$^+$] 604. Found 604.

Example 10

3-((R)-1-{(S)-1-[5-(4-Iodo-phenyl)-1H-imidazol-2-yl]-2-methyl-propyl}-2,5-dioxo-imidazolidin-4-yl)-propionic Acid; Hydrochloride Salt

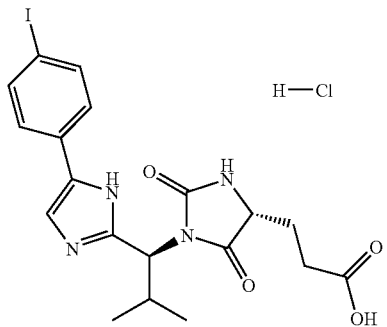

Prepared by the same method as described in example 8 except that (i) commercially available (S)-2-tert-butoxycarbonylamino-3-methyl-butyric acid was used in place of (2S, 3S)-2-tert-butoxycarbonylamino-3-phenyl-butyric acid in step 10-E; and (ii) commercially available (R)-2-(9H-fluoren-9-ylmethoxycarbonylamino)-pentanedioic acid 5-tert-butyl ester was used in place of (R)-2-(9H-fluoren-9-ylmethoxycarbonylamino)-succinic acid 4-tert-butyl ester in step 10-G. LC-MS: calcd for $C_{19}H_{21}IN_4O_4$ [M+H$^+$] 497. Found 497.

Example 11

N-(2-Hydroxy-ethoxy)-3-((R)-1-{(S)-1-[5-(4-iodo-phenyl)-1H-imidazol-2-yl]-2-methyl-propyl}-2,5-dioxo-imidazolidin-4-yl)-propionamide

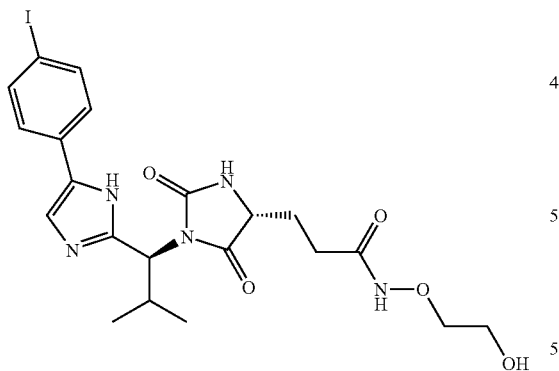

Prepared by the same method as described in example 9 except that (i) 3-((R)-1-{(S)-1-[5-(4-iodo-phenyl)-1H-imidazol-2-yl]-2-methyl-propyl}-2,5-dioxo-imidazolidin-4-yl)-propionic acid; hydrochloride salt (prepared as described in example 10) was used in place of ((R)-1-{(1S,2S)-1-[5-(4-iodo-phenyl)-1H-imidazol-2-yl]-2-phenyl-propyl}-2,5-dioxo-imidazolidin-4-yl)-acetic acid; hydrochloride salt in step 11-N; and (ii) following the chromatographic purification in step 11-O two products were obtained, N-(2-hydroxy-ethoxy)-3-((R)-1-{(S)-1-[5-(4-iodo-phenyl)-1H-imidazol-2-yl]-2-methyl-propyl}-2,5-dioxo-imidazolidin-4-yl)-propionamide and 3-((R)-1-{(S)-1-[5-(4-iodo-phenyl)-1H-imidazol-2-yl]-2-methyl-propyl}-2,5-dioxo-imidazolidin-4-yl)-propionic acid methyl ester (described in example 12). LC-MS: calcd for $C_{21}H_{26}IN_5O_5$ [M+H$^+$] 556. Found 556.

Example 12

3-((R)-1-{(S)-1-[5-(4-Iodo-phenyl)-1H-imidazol-2-yl]-2-methyl-propyl}-2,5-dioxo-imidazolidin-4-yl)-propionic Acid Methyl Ester

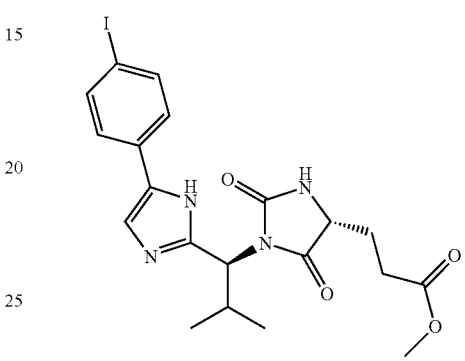

Prepared as described in example 11. LC-MS: calcd for $C_{20}H_{23}IN_4O_4$ [M+H$^+$] 511. Found 511.

Example 13

(R)-5-Cyclopropylmethyl-3-{(1S,2S)-1-[5-(2-fluoro-4-iodo-phenyl)-4-methyl-1H-imidazol-2-yl]-2-phenyl-propyl}-imidazolidine-2,4-dione

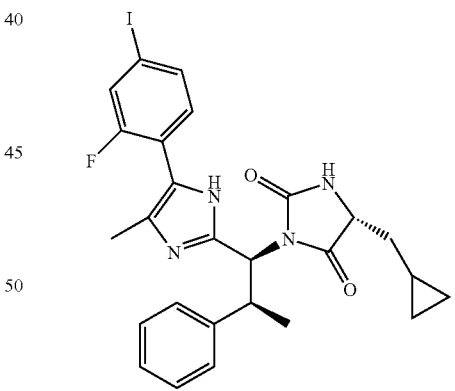

Prepared by the same method as described in example 1 except that (i) steps A, B and C were omitted; (ii) 1-(2-fluoro-4-iodo-phenyl)-propan-1-one (prepared as described below) was used in place of 1-(2-fluoro-4-iodo-phenyl)-ethanone in step 13-D; (iii) chlorination of the 5-position of the imidazole ring with N-chlorosuccinimide in step 13-F was omitted, and (iv) in step 13-G commercially available (R)-2-tert-butoxycarbonylamino-3-cyclopropyl-propionic acid was used in place of (R)-tert-butoxycarbonylamino-[4-(2-tert-butoxy-ethoxy)-phenyl]-acetic acid.

Preparation of 1-(2-fluoro-4-iodo-phenyl)-propan-1-one: A mixture of 3-fluoro-iodobenzene (98% purity) (17.6 g, 77.7 mmol) and aluminum chloride (99% purity) (9.41 g, 69.93 mmol) in 1,2 dichloroethane (60 mL) was cooled in an ice/water bath with stirring for 30 minutes. To this was added propionyl chloride (98% purity) (6.97 g, 73.81 mmol). The mixture was slowly warmed to 70° C. over 6 hours. The mixture was then poured into a 1:1 v/v mixture of ice/water and ethyl acetate. 6N Aqueous hydrochloric acid was then carefully added (20 mL) and the mixture extracted with ethyl acetate (2×100 mL). The combined organic extracts were then washed with 5% w/v aqueous sodium hydrogen sulfite (100 mL) and water (3×200 mL), dried over sodium sulfate, filtered and the filtrate passed over a plug of silica gel (1"×3") and eluted with ethyl acetate (200 mL). The organic eluant was concentrated in vacuo to give a brown oil (16 g) that was further purified using a 300 g ISCO Teledyne column gradient eluted with 0 to 5% v/v ethyl acetate in hexanes over 1.5 hours. Fractions containing pure product were combined and concentrated in vacuo to give 1-(2-fluoro-4-iodo-phenyl)-propan-1-one as a yellow solid (1.35 g, 6.6%). Fractions containing impure product were reprocessed using a 120 g ISCO Teledyne column gradient eluted with 0 to 5% v/v ethyl acetate in hexanes over 50 minutes to obtain additional 1-(2-fluoro-4-iodo-phenyl)-propan-1-one as a yellow solid (1.66 g, 8.1%). HR-MS: calcd for $C_{26}H_{26}FIN_4O_2$ [M+H$^+$] 573.1157. Found 573.1153.

Example 14

(R)-3-{(1S,2S)-1-[5-(4-Bromo-2-methyl-phenyl)-1H-imidazol-2-yl]-2-phenyl-propyl}-5-[4-(2-hydroxy-ethoxy)-phenyl]-imidazolidine-2,4-dione

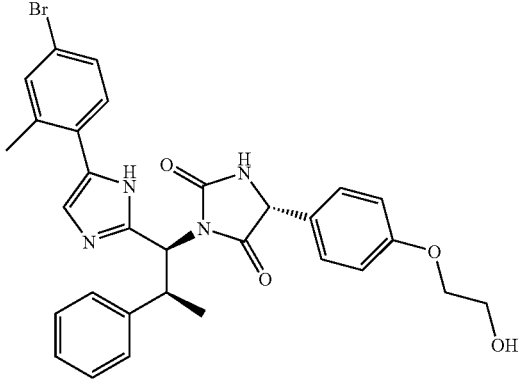

Prepared by the same method as described in example 1 except that (i) steps A, B and C were omitted; (ii) 1-(4-bromo-2-methyl-phenyl)-ethanone (prepared as described below in steps 14-I and 14-J) was used in place of 1-(2-fluoro-4-iodo-phenyl)-ethanone in step 14-D; and (iii) chlorination of the 5-position of the imidazole ring with N-chlorosuccinimide in step 14-F was omitted.

Step 14-I: To a solution of 4-bromo-2-methyl-benzoic acid (1.00 g, 4.65 mmol) in methylene chloride (40 mL) at room temperature, were added N-ethyl-N'-(3-dimethylaminopropyl)carbodiimide hydrochloride (0.936 g, 4.88 mmol), triethylamine (1.49 mL, 1.07 mmol) and N,O-dimethylhydroxylamine hydrochloride (0.544 g, 5.86 mmol). The mixture was stirred at room temperature overnight and then diluted with ethyl acetate (50 mL) and washed with 0.5 M aqueous sodium hydroxide solution (75 mL). The aqueous layer was separated, extracted with ethyl acetate (50 mL) and the organic extracts combined, washed with brine, dried over sodium sulfate, filtered and concentrated in vacuo. The crude product was purified by chromatography over silica gel gradient eluted between 0 and 50% v/v ethyl acetate in hexanes to give 4-bromo-N-methoxy-2,N-dimethyl-benzamide (886 mg, 74%).

Step 14-J: To a solution of 4-bromo-N-methoxy-2,N-dimethyl-benzamide (886 mg, 3.43 mmol) in anhydrous tetrahydrofuran (20 mL) at −60° C. under an atmosphere of nitrogen was added 3.0 M methylmagnesium chloride in tetrahydrofuran (1.26 mL, 3.78 mmol) via syringe. The reaction was stirred for 20 minutes at −60° C., then at room temperature for 30 minutes. Saturated aqueous ammonium chloride solution was added, the mixture was poured into a separatory funnel and extracted with diethyl ether (3×50 mL). The combined organic extracts were dried over sodium sulfate, filtered and concentrated in vacuo to give 1-(4-bromo-2-methyl-phenyl)-ethanone (700 mg, 96%). HR-MS: calcd for $C_{30}H_{29}BrN_4O_4$ [M+H$^+$] 589.1445. Found 589.1445.

Example 15

2-[4-((R)-1-{(1S,2S)-1-[5-(4-Bromo-2-fluoro-phenyl)-4-ethyl-1H-imidazol-2-yl]-2-phenyl-propyl}-2,5-dioxo-imidazolidin-4-yl)-phenoxy]-N,N-dimethyl-acetamide

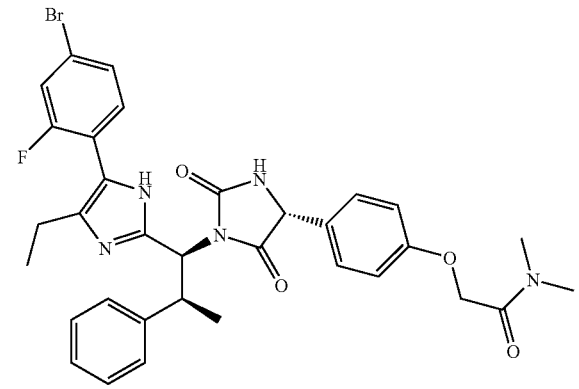

Prepared by the same method as described in example 6 except that (i) 4-bromo-2-fluorobenzoic acid was used in place of 4-bromo-2-chlorobenzoic acid in step 15-I and (ii) n-propyl magnesium chloride (in place of ethyl magnesium chloride) was reacted with 4-bromo-2-fluoro-N-methoxy-N-methyl-benzamide (from step 15-I) in step 15-J. HR-MS: calcd for $C_{33}H_{33}BrFN_5O_4$ [M+H$^+$] 662.1773. Found 662.1773.

Example 16

(R)-5-[4-(2-Hydroxy-ethoxy)-phenyl]-3-[(S)-1-[5-(4-iodo-phenyl)-1H-imidazol-2-yl]-2-(2-trifluoromethyl-phenyl)-ethyl]-imidazolidine-2,4-dione

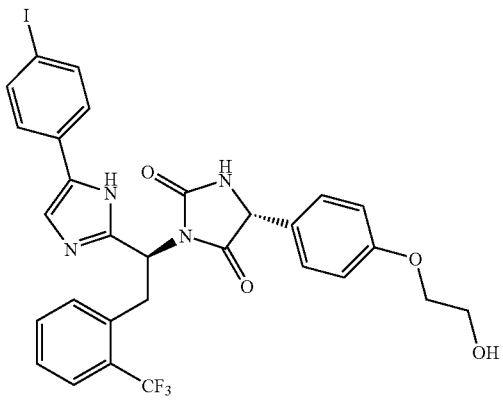

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 16-D; (iii) (S)-2-tert-butoxycarbonylamino-3-(2-trifluoromethyl-phenyl)-propionic acid was used in place of (2S,3S)-2-tert-butoxycarbonylamino-3-phenyl-butyric acid in step 16-E; and (iv) chlorination of the 5-position of the imidazole ring with N-chlorosuccinimide in step 16-F was omitted. HR-MS: calcd for $C_{29}H_{24}F_3IN_4O_4$ $[M+H^+]$ 677.0867. Found 677.0873.

Example 17

(R)-3-{(1S,2S)-1-[5-(2-Fluoro-phenyl)-1H-imidazol-2-yl]-2-phenyl-propyl}-5-[4-(2-hydroxy-ethoxy)-phenyl]-imidazolidine-2,4-dione

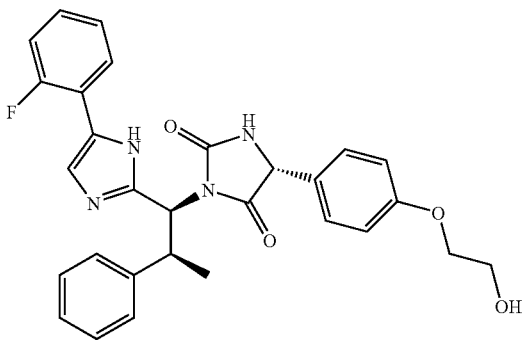

Prepared by the same method as described in example 1 except that (i) chlorination of the 5-position of the imidazole ring with N-chlorosuccinimide was omitted and a solution of 4.0M hydrogen chloride in p-dioxane was used during the deprotection stage in step 17-F; (ii) {(1S,2S)-1-[5-(2-fluoro-phenyl)-1H-imidazol-2-yl]-2-phenyl-propyl}-carbamic acid tert-butyl ester (prepared as described below in step 17-I) was used in place of {(1S,2S)-1-[5-(2-fluoro-4-iodo-phenyl)-1H-imidazol-2-yl]-2-phenyl-propyl}-carbamic acid tert-butyl ester in step 17-G; (iii) during the deprotection stage of step 17-H, a solution of 1:1 v/v trifluoroacetic acid in methylene chloride was used in place of hydrogen chloride gas and p-dioxane; and (iv) silylation with chlorotrimethylsilane and triethylamine in step 17-H was omitted.

Step 17-I: To a degassed mixture of {(1S,2S)-1-[5-(2-fluoro-4-iodo-phenyl)-1H-imidazol-2-yl]-2-phenyl-propyl}-carbamic acid tert-butyl ester (150 mg, 0.288 mmol) in toluene (5 mL) and 1:1 v/v deionized water/ethanol (2 mL) were added dichlorobis(tricyclohexylphosphine)palladium (II) (6.4 mg, 0.009 mmol), cyclopropylboronic acid (27 mg, 0.314 mmol), potassium carbonate (159 mg, 1.15 mmol) and the mixture refluxed for 3 hours under an atmosphere of nitrogen. The mixture was diluted with ethyl acetate (50 mL) and washed with water (50 mL). The aqueous layer was washed with ethyl acetate (50 mL) and the combined organic extracts were washed with brine, dried over sodium sulfate, filtered and concentrated in vacuo. The crude product was purified by chromatography over silica gel gradient eluted between 0 and 40% v/v ethyl acetate in hexanes to give {(1S,2S)-1-[5-(2-fluoro-phenyl)-1H-imidazol-2-yl]-2-phenyl-propyl}-carbamic acid tert-butyl ester (122 mg, 107%) which was then used in step 17-G. HR-MS: calcd for $C_{29}H_{27}FN_4O_4$ $[M+H^+]$ 515.2089. Found 515.2089.

Example 18

(R)-3-{(S)-1-[5-(4-Iodo-phenyl)-1H-imidazol-2-yl]-2-phenyl-ethyl}-5-prop-2-ynyl-imidazolidine-2,4-dione

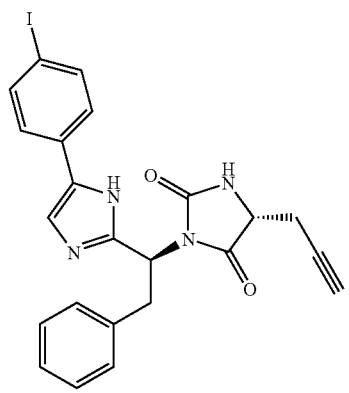

Prepared by the same method as described in example 1 except that (i) steps A, B, and C were omitted; (ii) commercially available 1-(4-iodo-phenyl)-ethanone was used in place of 1-(2-fluoro-4-iodo-phenyl)-ethanone in step 18-D; (iii) (S)-2-tert-butoxycarbonylamino-3-phenyl-propionic acid was used in place of (2S,3S)-2-tert-butoxycarbonylamino-3-phenyl-butyric acid in step 18-E; (iv) chlorination of the 5-position of the imidazole ring with N-chlorosuccinimide in step 18-F was omitted; (v) (R)-2-tert-butoxycarbonylamino-pent-4-ynoic acid was used in place of (R)-tert-butoxycarbonylamino-[4-(2-tert-butoxy-ethoxy)-phenyl]-acetic acid in step 18-G; and (vi) in step 18-H, formic acid (neat) heated to 30° C. was used in place of trifluoroacetic acid and silylation with chlorotrimethylsilane and triethylamine was omitted. HR-MS: calcd for $C_{23}H_{19}IN_4O_2$ $[M+H^+]$ 511.0626. Found 511.0623.

Example 19

(R)-3-{(1S,2S)-1-[5-(4-Bromo-2-chloro-phenyl)-1H-imidazol-2-yl]-2-phenyl-propyl}-5-cyclopropyl-imidazolidine-2,4-dione

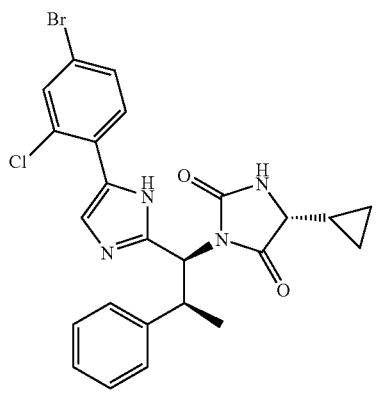

Prepared by the same method as described in example 1 except that (i) steps A, B and C were omitted; (ii) 1-(4-bromo-2-chloro-phenyl)-ethanone (prepared as described in example 6, steps 6-I and 6-J) was used in place of 1-(2-fluoro-4-iodo-phenyl)-ethanone in step 19-D; (iii) chlorination of the 5-position of the imidazole ring with N-chlorosuccinimide in step 19-F was omitted; (iv) commercially available (R)-tert-butoxycarbonylamino-cyclopropyl-acetic acid was used in place of (R)-tert-butoxycarbonylamino-[4-(2-tert-butoxy-ethoxy)-phenyl]-acetic acid in step 19-G; and (v) silylation with chlorotrimethylsilane and triethylamine in step 19-H was omitted. HR-MS: calcd for $C_{24}H_{22}BrClN_4O_2$ [M+H$^+$] 513.0688. Found 513.0685.

Example 20

(R)-3-{(1S,2S)-1-[4-Chloro-5-(4-chloro-2-fluoro-phenyl)-1H-imidazol-2-yl]-2-phenyl-propyl}-5-[4-(2-hydroxy-ethoxy)-phenyl]-imidazolidine-2,4-dione

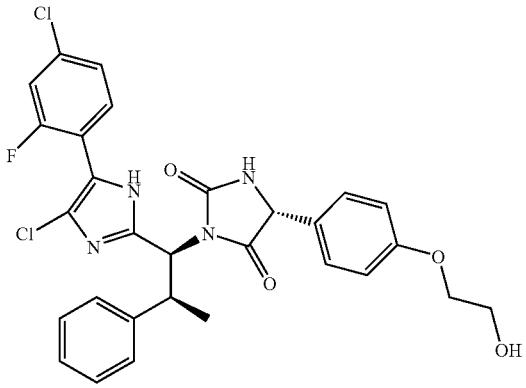

Prepared by the same method as described in example 1 except that (i) steps A, B and C were omitted; and (ii) commercially available 1-(4-chloro-2-fluoro-phenyl)-ethanone was used in place of 1-(2-fluoro-4-iodo-phenyl)-ethanone in step 20-D. HR-MS: calcd for $C_{29}H_{25}Cl_2FN_4O_4$ [M+H$^+$] 583.1310. Found 583.1313.

Example 21

(R)-3-{(S)-1-[5-(4-Bromo-3-fluoro-phenyl)-1H-imidazol-2-yl]-2-phenyl-ethyl}-5-[4-(2-hydroxy-ethoxy)-phenyl]-imidazolidine-2,4-dione

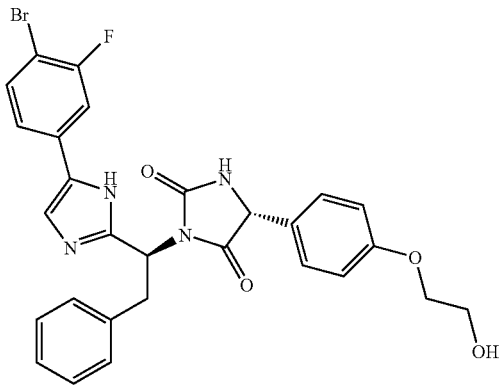

Prepared by the same method as described in example 1 except that (i) steps A, B and C were omitted; (ii) 1-(4-bromo-3-fluoro-phenyl)-propan-1-one was used in place of 1-(2-fluoro-4-iodo-phenyl)-ethanone in step 21-D; (iii) (S)-2-tert-butoxycarbonylamino-3-phenyl-propionic acid was used in place of (2S,3S)-2-tert-butoxycarbonylamino-3-phenyl-butyric acid in step 21-E; and (iv) chlorination of the 5-position of the imidazole ring with N-chlorosuccinimide in step 21-F was omitted. 1-(4-Bromo-3-fluoro-phenyl)-propan-1-one was prepared as described in example 6 for the preparation of 1-(4-bromo-2-chloro-phenyl)-ethanone except that 4-bromo-3-fluorobenzoic acid was used in place of 4-bromo-2-chlorobenzoic acid in step 21-I. HR-MS: calcd for $C_{28}H_{24}BrFN_4O_4$ [M+H$^+$] 579.1038. Found 579.1038.

Example 22

(R)-3-{(1S,2S)-1-[5-(2-Fluoro-4-iodo-phenyl)-1H-imidazol-2-yl]-2-methyl-butyl}-5-[4-(2-hydroxy-ethoxy)-phenyl]-imidazolidine-2,4-dione

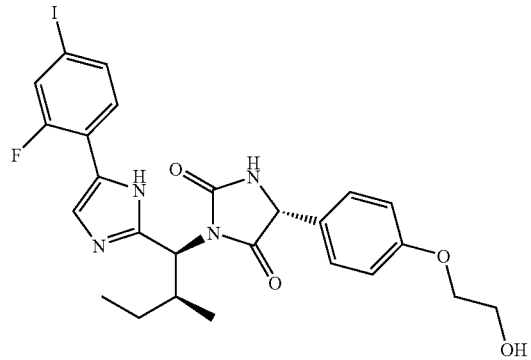

Prepared by the same method as described in example 1 except that (i) in step 22-E (2S,3S)-2-tert-butoxycarbonylamino-3-methyl-pentanoic acid was used in place of (2S,3S)-2-tert-butoxycarbonylamino-3-phenyl-butyric acid; and (ii) chlorination of the 5-position of the imidazole ring with N-chlorosuccinimide in step 22-F was omitted. HR-MS: calcd for $C_{25}H_{26}FIN_4O_4$ [M+H$^+$] 593.1056. Found 593.1055.

Example 23

(R)-3-{(S)-1-[5-(2-Fluoro-4-iodo-phenyl)-1H-imidazol-2-yl]-2-thiazol-4-yl-ethyl}-5-[4-(2-hydroxy-ethoxy)-phenyl]-imidazolidine-2,4-dione

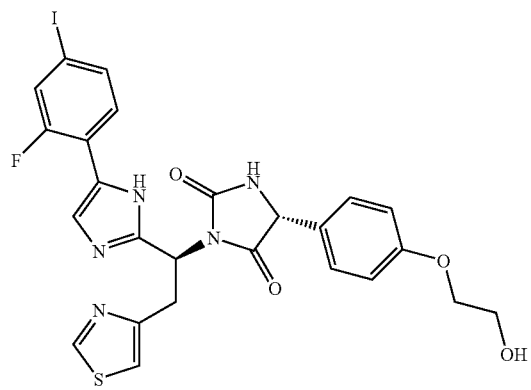

Prepared by the same method as described in example 1 except that (i) in step 23-E (S)-2-tert-butoxycarbonylamino-3-thiazol-4-yl-propionic acid was used in place of (2S,3S)-2-tert-butoxycarbonylamino-3-phenyl-butyric acid; and (ii) chlorination of the 5-position of the imidazole ring with N-chlorosuccinimide in step 23-F was omitted. HR-MS: calcd for $C_{25}H_{21}FlN_5O_4S$ [M+H$^+$] 634.0416. Found 634.0415.

Example 24

(R)-3-{(S)-Cyclopropyl-[5-(2-fluoro-4-iodo-phenyl)-1H-imidazol-2-yl]-methyl}-5-[4-(2-hydroxy-ethoxy)-phenyl]-imidazolidine-2,4-dione

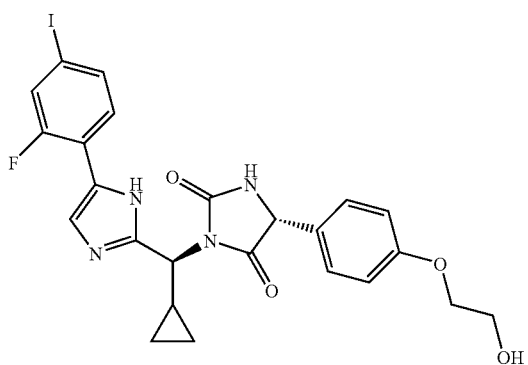

Prepared by the same method as described in example 1 except that (i) in step 24-E (S)-tert-butoxycarbonylamino-cyclopropyl-acetic acid was used in place of (2S,3S)-2-tert-butoxycarbonylamino-3-phenyl-butyric acid; and (ii) chlorination of the 5-position of the imidazole ring with N-chlorosuccinimide in step 24-F was omitted. HR-MS: calcd for $C_{24}H_{22}FlN_4O_4$ [M+H$^+$] 577.0743. Found 577.0739.

Example 25

(R)-3-[(S)-1-[5-(2-Fluoro-4-iodo-phenyl)-1H-imidazol-2-yl]-2-(2-fluoro-phenyl)-ethyl]-5-[4-(2-hydroxy-ethoxy)-phenyl]-imidazolidine-2,4-dione

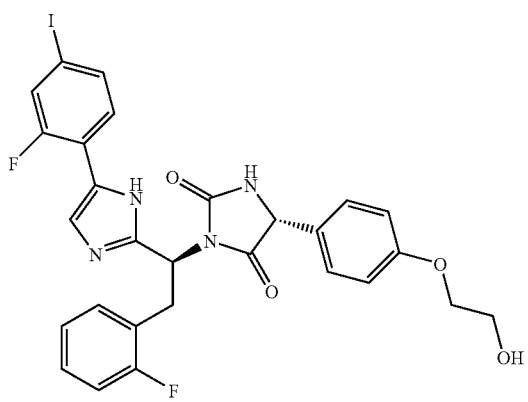

Prepared by the same method as described in example 1 except that (i) in step 25-E (S)-2-tert-butoxycarbonylamino-3-(2-fluoro-phenyl)-propionic acid was used in place of (2S,3S)-2-tert-butoxycarbonylamino-3-phenyl-butyric acid; and (ii) chlorination of the 5-position of the imidazole ring with N-chlorosuccinimide in step 25-F was omitted. HR-MS: calcd for $C_{28}H_{23}F_2IN_4O_4$ [M+H$^+$] 645.0805. Found 645.0800.

Example 26

(R)-3-{(S)-1-[5-(2-Fluoro-4-iodo-phenyl)-1H-imidazol-2-yl]-3-phenyl-propyl}-5-[4-(2-hydroxy-ethoxy)-phenyl]-imidazolidine-2,4-dione

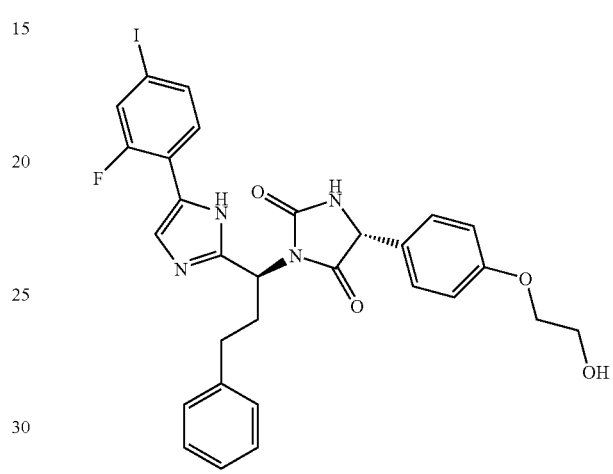

Prepared by the same method as described in example 1 except that (i) in step 26-E (S)-2-tert-butoxycarbonylamino-4-phenyl-butyric acid was used in place of (2S,3S)-2-tert-butoxycarbonylamino-3-phenyl-butyric acid; and (ii) chlorination of the 5-position of the imidazole ring with N-chlorosuccinimide in step 26-F was omitted. HR-MS: calcd for $C_{29}H_{26}FlN_4O_4$ [M+H$^+$] 641.1056. Found 641.1050.

Example 27

(R)-3-{(S)-2-(2-Chloro-phenyl)-1-[5-(2-fluoro-4-iodo-phenyl)-1H-imidazol-2-yl]-ethyl}-5-[4-(2-hydroxy-ethoxy)-phenyl]-imidazolidine-2,4-dione

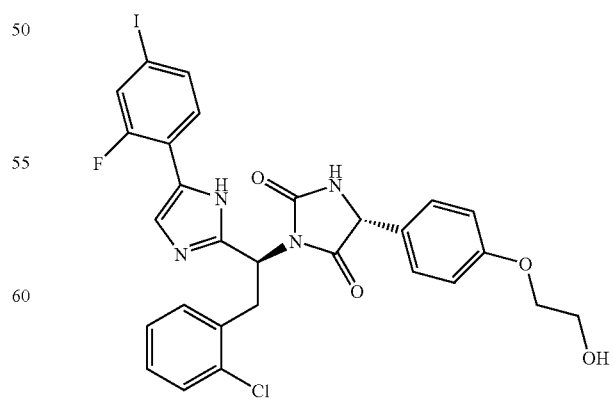

Prepared by the same method as described in example 1 except that (i) in step 27-E (S)-2-tert-butoxycarbonylamino- 3-(2-chloro-phenyl)-propionic acid was used in place of (2S, 3S)-2-tert-butoxycarbonylamino-3-phenyl-butyric acid; and (ii) chlorination of the 5-position of the imidazole ring with N-chlorosuccinimide in step 27-F was omitted. HR-MS: calcd for $C_{28}H_{23}ClFIN_4O_4$ [M+H$^+$] 661.0510. Found 661.0505.

Example 28

(R)-5-[4-(2-Hydroxy-ethoxy)-phenyl]-3-[(S)-1-[5-(4-iodo-phenyl)-1H-imidazol-2-yl]-2-(4-methoxy-phenyl)-ethyl]-imidazolidine-2,4-dione

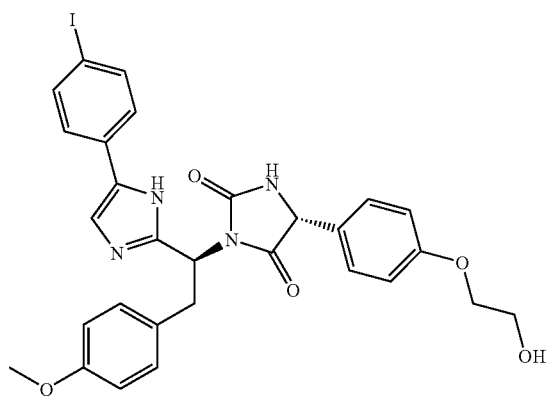

Prepared by the same method as described in example 1 except that (i) steps A, B, and C were omitted; (ii) commercially available 1-(4-iodo-phenyl)-ethanone was used in place of 1-(2-fluoro-4-iodo-phenyl)-ethanone in step 28-D; (iii) (S)-2-tert-butoxycarbonylamino-3-(4-methoxy-phenyl)-propionic acid was used in place of (2S,3S)-2-tert-butoxycarbonylamino-3-phenyl-butyric acid in step 28-E; and (iv) chlorination of the 5-position of the imidazole ring with N-chlorosuccinimide in step 28-F was omitted. HR-MS: calcd for $C_{29}H_{27}IN_4O_5$ [M+H$^+$] 639.1099. Found 639.1095.

Example 29

(R)-3-{(1R,2R)-1-[5-(2-Fluoro-4-iodo-phenyl)-1H-imidazol-2-yl]-2-methoxy-propyl}-5-[4-(2-hydroxy-ethoxy)-phenyl]-imidazolidine-2,4-dione

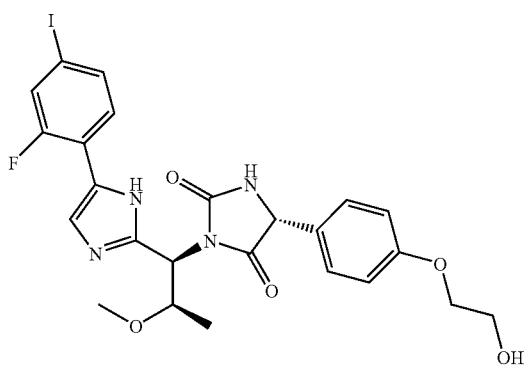

Prepared by the same method as described in example 1 except that (i) in step 29-E (2S,3R)-2-tert-butoxycarbonylamino-3-methoxy-butyric acid was used in place of (2S,3S)-2-tert-butoxycarbonylamino-3-phenyl-butyric acid; and (ii) chlorination of the 5-position of the imidazole ring with N-chlorosuccinimide in step 29-F was omitted. HR-MS: calcd for $C_{24}H_{24}FIN_4O_5$ [M+H$^+$] 595.0848. Found 595.0848.

Example 30

(R)-3-{(1S,2S)-1-[5-(4-Ethynyl-2-fluoro-phenyl)-1H-imidazol-2-yl]-2-phenyl-propyl}-5-[4-(2-hydroxy-ethoxy)-phenyl]-imidazolidine-2,4-dione

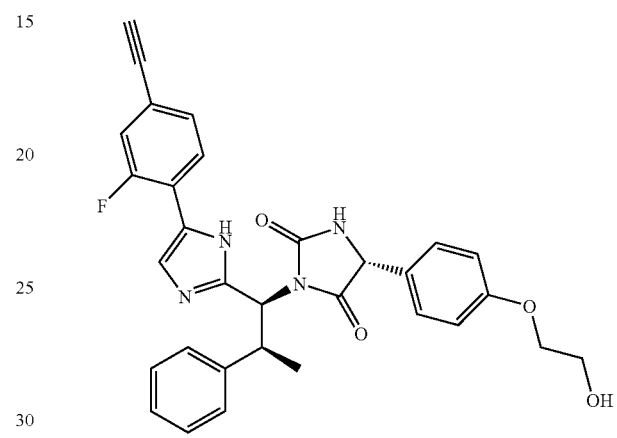

Prepared by the same method as described in example 1 except that (i) step 30-P (see below) was performed following step 30-E and prior to performing step 30-F; (ii) in step 30-F, chlorination of the 5-position of the imidazole ring with N-chlorosuccinimide was omitted and formic acid (neat) heated to 30° C. was used in place of trifluoroacetic acid to effect removal of the tert-butyloxycarbonyl protecting group in {(1S,2S)-1-[5-(2-fluoro-4-trimethylsilanylethynyl-phenyl)-1H-imidazol-2-yl]-2-phenyl-propyl}-carbamic acid tert-butyl ester; (iii) in step 30-H, 4.0 M hydrogen chloride in p-dioxane (5.0 equivalents) was used in place of hydrogen chloride gas and subsequently the trimethylsilyl protecting group was removed (according to the procedure in step 30-Q) prior to cyclization with diphosgene; and (iv) the product from step 30-H was deprotected according to the procedure in step 30-R.

Step 30-P: A solution of {(1S,2S)-1-[5-(2-fluoro-4-iodo-phenyl)-1H-imidazol-2-yl]-2-phenyl-propyl}-carbamic acid tert-butyl ester (286 mg, 0.55 mmol) (prepared in step 30-E), copper (I) iodide (10.50 mg, 0.055 mmol) and dichlorobis(triphenylphosphine)palladium(II) (39 mg, 0.055 mmol) in N,N-dimethylformamide (5 mL) was degassed with dry nitrogen with stirring for 5 minutes. Triethylamine (229 µL, 1.65 mmol) and trimethylsilylacetylene (233 µL, 1.65 mmol) were added and the resulting solution was stirred for 24 hours at room temperature. The reaction was poured into ethyl acetate (25 mL) and washed with water (2×10 mL). The organic layer was washed with brine, dried over sodium sulfate, filtered and concentrated in vacuo. The residue was purified by chromatography over silica gel gradient eluted between 10 and 50% v/v ethyl acetate in hexanes to give {(1S,2S)-1-[5-(2-fluoro-4-trimethylsilanylethynyl-phenyl)-1H-imidazol-2-yl]-2-phenyl-propyl}-carbamic acid tert-butyl ester (260 mg, 96%). HR-MS: calcd for $C_{28}H_{34}FN_3O_2Si$ [M+H$^+$] 492.2477. Found 492.2475.

Step 30-Q: To a solution of 2-amino-2-[4-(2-tert-butoxy-ethoxy)-phenyl]-N-{(1S,2S)-1-[5-(2-fluoro-4-trimethylsilanylethynyl-phenyl)-1H-imidazol-2-yl]-2-phenyl-propyl}-acetamide (290 mg, 0.45 mmol) in tetrahydrofuran (10 mL) at room temperature under an atmosphere of nitrogen was added 1.0 M tetrabutylammonium fluoride in tetrahydrofuran (680 μL, 0.68 mmol) and the resulting solution was allowed to stir for 2 hours. The reaction was poured into ethyl acetate (50 mL), washed with water (2×20 mL), brine, dried over sodium sulfate, filtered and concentrated in vacuo to give 2-amino-2-[4-(2-tert-butoxy-ethoxy)-phenyl]-N-{(1S,2S)-1-[5-(4-ethynyl-2-fluoro-phenyl)-1H-imidazol-2-yl]-2-phenyl-propyl}-acetamide which was used without further purification (250 mg, 97%).

Step 30-R: To a solution of (R)-5-[4-(2-tert-butoxy-ethoxy)-phenyl]-3-{(1S,2S)-1-[5-(4-ethynyl-2-fluoro-phenyl)-1H-imidazol-2-yl]-2-phenyl-propyl}-imidazolidine-2,4-dione (293 mg, 0.49 mmol) in 1:1 v/v dichloromethane/acetonitrile (10 mL) at 0° C. under an atmosphere of nitrogen was added sodium iodide (148 mg, 0.99 mmol) followed by chlorotrimethylsilane (184 μL, 1.45 mmol) and the resulting mixture was allowed to stir for 30 minutes. Additional sodium iodide (148 mg, 0.99 mmol) followed by chlorotrimethylsilane (184 μL, 1.45 mmol) was added and stirring continued for 45 minutes. The reaction was then poured into ethyl acetate (30 mL) and washed with 10% w/v aqueous sodium thiosulfate solution. The organic extract was washed with brine, dried over sodium sulfate, filtered and concentrated in vacuo. The residue was purified by chromatography over silica gel eluted with 80 to 100% v/v ethyl acetate in hexanes to give (R)-3-{(1S,2S)-1-[5-(4-ethynyl-2-fluoro-phenyl)-1H-imidazol-2-yl]-2-phenyl-propyl}-5-[4-(2-hydroxy-ethoxy)-phenyl]-imidazolidine-2,4-dione (59 mg, 22%). HR-MS: calcd for $C_{31}H_{27}FN_4O_4$ [M+H$^+$] 539.2089. Found 539.2086.

Example 31

(R)-3-[(S)-1-[5-(2-Fluoro-4-iodo-phenyl)-1H-imidazol-2-yl]-2-(4-fluoro-phenyl)-ethyl]-5-[4-(2-hydroxy-ethoxy)-phenyl]-imidazolidine-2,4-dione

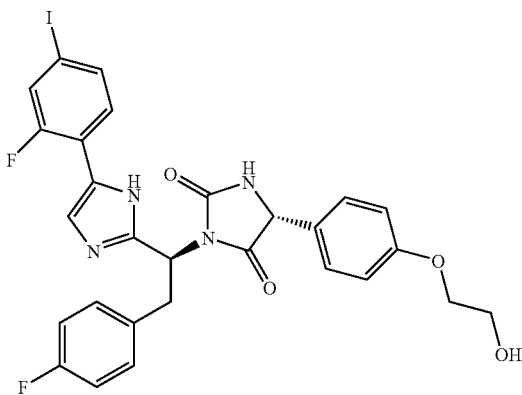

Prepared by the same method as described in example 1 except that (i) (S)-2-tert-butoxycarbonylamino-3-(4-fluoro-phenyl)-propionic acid was used in place of (2S,3S)-2-tert-butoxycarbonylamino-3-phenyl-butyric acid in step 31-E; and (ii) chlorination of the 5-position of the imidazole ring with N-chlorosuccinimide in step 31-F was omitted. HR-MS: calcd for $C_{28}H_{23}F_2IN_4O_4$ [M+H$^+$] 645.0805. Found 645.0803.

Example 32

4-((S)-2-[5-(2-Fluoro-4-iodo-phenyl)-1H-imidazol-2-yl]-2-{(R)-4-[4-(2-hydroxy-ethoxy)-phenyl]-2,5-dioxo-imidazolidin-1-yl}-ethyl)-benzonitrile

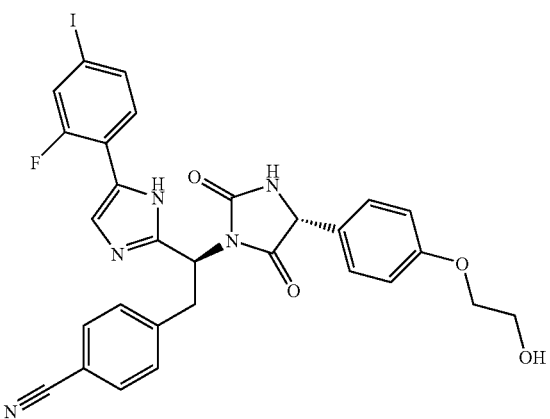

Prepared by the same method as described in example 1 except that (i) (S)-2-tert-butoxycarbonylamino-3-(4-cyano-phenyl)-propionic acid was used in place of (2S,3S)-2-tert-butoxycarbonylamino-3-phenyl-butyric acid in step 32-E; and (ii) chlorination of the 5-position of the imidazole ring with N-chlorosuccinimide in step 32-F was omitted. HR-MS: calcd for $C_{29}H_{23}FIN_5O_4$ [M+H$^+$] 652.0852. Found 652.0854.

Example 33

(R)-5-[4-((R)-2,3-Dihydroxy-propoxy)-phenyl]-3-{(S)-1-[5-(2-fluoro-4-iodo-phenyl)-1H-imidazol-2-yl]-2-methyl-propyl}-imidazolidine-2,4-dione

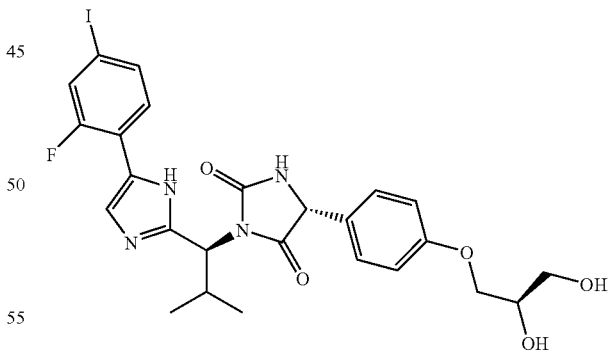

Prepared by the same method as described in example 1 except that (i) (S)-2-tert-butoxycarbonylamino-3-methyl-butyric acid was used in place of (2S,3S)-2-tert-butoxycarbonylamino-3-phenyl-butyric acid in step 33-E; (ii) chlorination of the 5-position of the imidazole ring with N-chlorosuccinimide in step F was omitted; and (iii) (R)-tert-butoxycarbonylamino-[4-((S)-2,2-dimethyl-[1,3]dioxolan-4-ylmethoxy)-phenyl]-acetic acid (prepared as described below in steps 33-S and 33-T) was used in place of (R)-tert-butoxycarbonylamino-[4-(2-tert-butoxy-ethoxy)-phenyl]-acetic acid in step 33-G.

Step 33-S: To a solution of (S)-2,2-dimethyl-1,3-dioxolane-4-methanol (5.22 g, 39.5 mmol) in dichloromethane (60 mL) at 0° C. under an atmosphere of dry argon were added triethylamine (11 mL, 79 mmol) and 2,5-dichlorosulfonyl chloride (10.18 g, 41.5 mmol) and the mixture left to stir and warm slowly to ambient temperature overnight. The reaction mixture was diluted with dichloromethane and washed with water. The aqueous layer was separated and washed once with dichloromethane. The combined organic layers were washed with saturated aqueous sodium hydrogen carbonate solution (once), brine (once), dried over sodium sulfate, filtered and concentrated in vacuo to leave an oily residue. The residue was purified by chromatography over silica gel gradient eluted form 0 to 40% v/v ethyl acetate in hexanes to give 2,5-dichloro-benzenesulfonic acid (R)-2,2-dimethyl-[1,3]dioxolan-4-ylmethyl ester as a colorless solid (11.06 g, 82%).

Step 33-T: To a stirred solution of (R)-tert-butoxycarbonylamino-(4-hydroxy-phenyl)-acetic acid (1.4 g, 5.24 mmol) in dry N,N-dimethylformamide (25 mL) at 0° C. under an atmosphere of dry argon was added sodium hydride (60% suspension in mineral oil) (290 mg, 0.12 mmol) and the mixture stirred at 0° C. for 15 minutes. 2,5-Dichloro-benzenesulfonic acid (R)-2,2-dimethyl-[1,3]dioxolan-4-ylmethyl ester (2.14 mmol, 6.29 mmol) was added to the reaction mixture to form a yellow solution which was stirred at ambient temperature for 5 minutes before warming to 100° C. for 10 minutes. The reaction mixture which by now contained a heavy precipitate was cooled to ambient temperature, diluted with ethyl acetate, cooled to 0° C. and treated with an equal volume of water. The stirred mixture was acidified to pH≈4 with 1 M aqueous hydrochloric acid. The organic layer was separated and the aqueous layer extracted with ethyl acetate. The combined organic layers were washed with water (three times), dried over sodium sulfate, filtered through a thin pad of silica gel and concentrated in vacuo to give (R)-tert-butoxycarbonylamino-[4-((S)-2,2-dimethyl-[1,3]dioxolan-4-ylmethoxy)-phenyl]-acetic acid as a pale yellow solid foam which was of adequate purity for subsequent use in step 33-G without additional purification (1.96 g, 96%). HR-MS: calcd for $C_{25}H_{26}FlN_4O_5$ [M+H$^+$] 609.1005. Found 609.1006.

Example 34

(R)-3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione

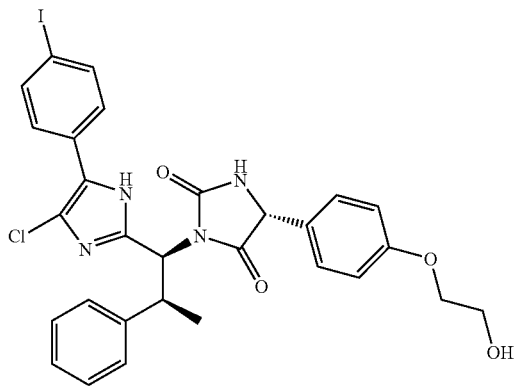

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 34-D; and (iii) following removal of the tert-butyl carbamate and tert-butyl ether protecting groups the cyclization in step 34-H was effected as described below.

Step 34-H: Following treatment with hydrogen chloride gas in p-dioxane to effect removal of tert-butyl carbamate and tert-butyl ether protecting groups the resulting solution was treated with 1:1 saturated aqueous sodium hydrogen carbonate/brine then extracted with ethyl acetate (3×). The combined ethyl acetate extracts were washed with brine, dried with sodium sulfate, filtered and concentrated in vacuo to provide crude (R)-2-amino-N-{(1S,2S)-1-[4-chloro-5-(4-iodo-phenyl)-1H-imidazol-2-yl]-2-phenyl-propyl}-2-[4-(2-hydroxy-ethoxy)-phenyl]-acetamide which was used immediately without further purification.

To a solution of (R)-2-amino-N-{(1S,2S)-1-[4-chloro-5-(4-iodo-phenyl)-1H-imidazol-2-yl]-2-phenyl-propyl}-2-[4-(2-hydroxy-ethoxy)-phenyl]-acetamide (1.00 g, 1.58 mmol) in tetrahydrofuran (30 mL) was added bis-pentafluorophenyl carbonate (750 mg, 1.90 mmol) and the mixture stirred at 0° C. for 1.5 hours. N,N-Diisopropylethylamine (290 µL, 1.66 mmol) was added and the reaction mixture stirred for an additional 15 minutes at 0° C. before diluting with ethyl acetate (50 mL), washing with water (2×25 mL), washing with brine (2×25 mL), drying over sodium sulfate, filtering and concentrating in vacuo. The residue was purified by chromatography over silica gel gradient eluted up to 9:1 v/v ethyl acetate in hexanes to give after concentration of the product containing fractions (R)-3-{(1S,2S)-1-[4-chloro-5-(4-iodo-phenyl)-1H-imidazol-2-yl]-2-phenyl-propyl}-5-[4-(2-hydroxy-ethoxy)-phenyl]-imidazolidine-2,4-dione as a colorless solid (800 mg, 77%). HR-MS: calcd for $C_{29}H_{26}ClIN_4O_4$ [M+H$^+$] 657.0760. Found 657.0764.

Example 35

(R)-3-{(1S,2S)-1-[5-(2-Chloro-4-iodo-phenyl)-1H-imidazol-2-yl]-2-phenyl-propyl}-5-[4-(2-hydroxy-ethoxy)-phenyl]-imidazolidine-2,4-dione

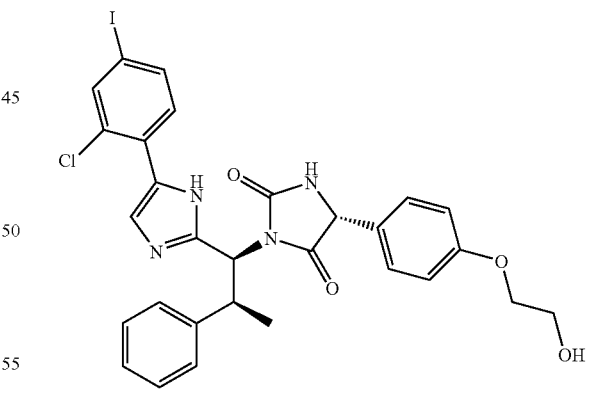

Prepared by the same method as described in example 1 except that (i) in step 35-A 2-chloro-1,4-diiodo-benzene was used in place of 2-fluoro-1,4-diiodo-benzene; (ii) chlorination of the 5-position of the imidazole ring with N-chlorosuccinimide in step F was omitted; and (iii) cyclization of (R)-2-amino-N-{(1S,2S)-1-[5-(2-chloro-4-iodo-phenyl)-1H-imidazol-2-yl]-2-phenyl-propyl}-2-[4-(2-hydroxy-ethoxy)-phenyl]-acetamide in step 35-H was performed as described in example 34. HR-MS: calcd for $C_{29}H_{26}ClIN_4O_4$ [M+H$^+$] 657.07600. Found 657.0757.

Example 36

(R)-5-[4-((R)-2,3-Dihydroxy-propoxy)-phenyl]-3-{(1S,2S)-1-[5-(2-fluoro-4-iodo-phenyl)-1H-imidazol-2-yl]-2-phenyl-propyl}-imidazolidine-2,4-dione

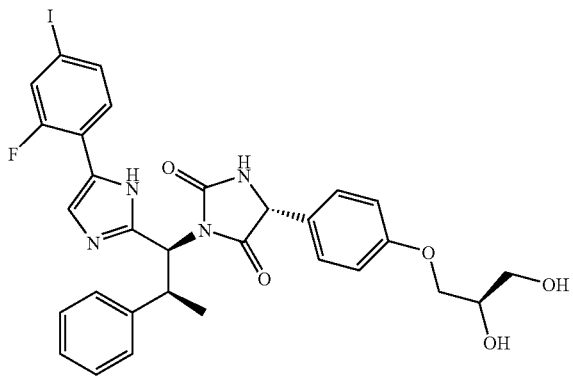

Prepared by the same method as described in example 1 except that (i) chlorination of the 5-position of the imidazole ring with N-chlorosuccinimide in step F was omitted; (ii) (R)-tert-butoxycarbonylamino-[4-((S)-2,2-dimethyl-[1,3]dioxolan-4-ylmethoxy)-phenyl]-acetic acid (prepared as described in example 33) was used in place of (R)-tert-butoxycarbonylamino-[4-(2-tert-butoxy-ethoxy)-phenyl]-acetic acid in step 36-G, and (iii) cyclization of (R)-2-amino-2-[4-((R)-2,3-dihydroxy-propoxy)-phenyl]-N-{(1S,2S)-1-[5-(2-fluoro-4-iodo-phenyl)-1H-imidazol-2-yl]-2-phenyl-propyl}-acetamide in step 36-H was performed as described in example 34. HR-MS: calcd for $C_{30}H_{28}FIN_4O_5$ [M+H$^+$] 671.1161. Found 671.1156.

Example 37

(R)-3-{(1S,2S)-1-[5-(2-Chloro-4-iodo-phenyl)-1H-imidazol-2-yl]-2-phenyl-propyl}-5-[4-((R)-2,3-dihydroxy-propoxy)-phenyl]-imidazolidine-2,4-dione

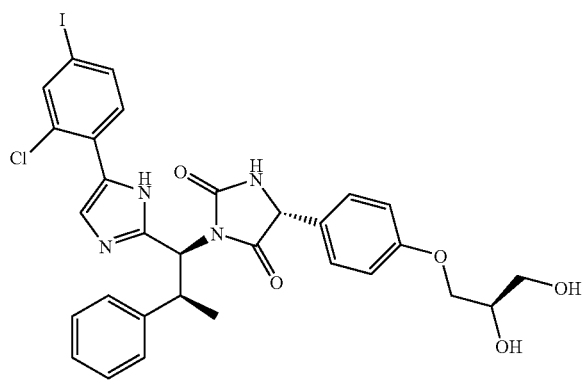

Prepared by the same method as described in example 36 except that in step 37-A 2-chloro-1,4-diiodo-benzene was used in place of 2-fluoro-1,4-diiodo-benzene. HR-MS: calcd for $C_{30}H_{28}ClIN_4O_5$ [M+H$^+$] 687.0866. Found 687.0869.

Example 38

3-((R)-1-{(S)-1-[5-(4-Iodo-phenyl)-1H-imidazol-2-yl]-2-methyl-propyl}-2,5-dioxo-imidazolidin-4-yl)-propionic Acid Tert-Butyl Ester

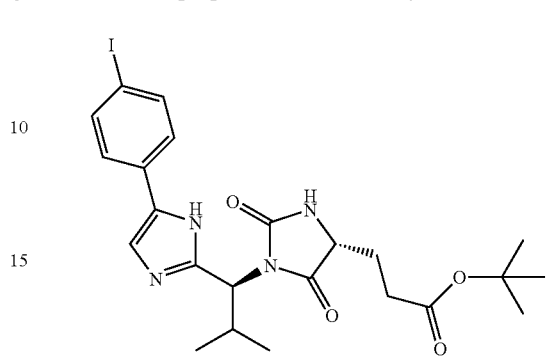

Prepared by the same method as described in example 10 except that step 10-M was omitted. LC-MS: calcd for $C_{23}H_{29}IN_4O_4$ [M+H$^+$] 553. Found 553.

Example 39

3-((R)-1-{(S)-1-[5-(4-Iodo-phenyl)-1H-imidazol-2-yl]-2-methyl-propyl}-2,5-dioxo-imidazolidin-4-yl)-N-(2-vinyloxy-ethoxy)-propionamide

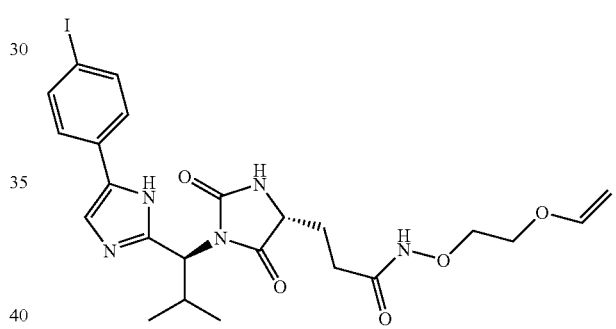

Prepared by the same method as described in example 11 except that step 11-0 was omitted. LC-MS: calcd for $C_{23}H_{28}IN_5O_5$ [M+H$^+$] 582. Found 582.

Example 40

(R)-5-[4-(2-Hydroxy-ethoxy)-phenyl]-3-{(S)-1-[5-(4-iodo-phenyl)-1H-imidazol-2-yl]-1-methyl-2-phenyl-ethyl}-imidazolidine-2,4-dione

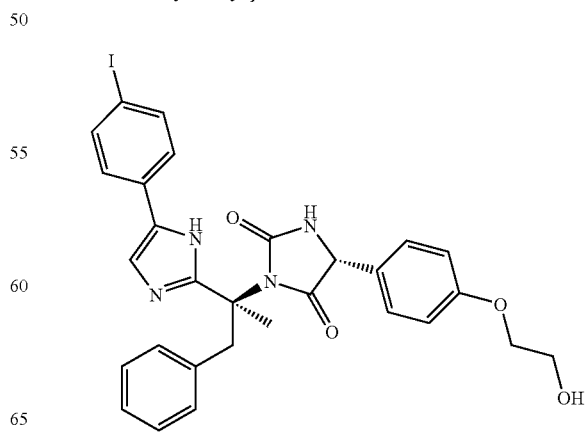

Prepared by the same method as described in example 1 except that (i) steps A, B and C were omitted; (ii) commercially available 1-(4-iodo-phenyl)-ethanone was used in place of 1-(2-fluoro-4-iodo-phenyl)-ethanone in step 40-D; (iii) (S)-2-tert-butoxycarbonylamino-2-methyl-3-phenyl-propionic acid was used in place of (2S,3S)-2-tert-butoxycarbonylamino-3-phenyl-butyric acid in step 40-E and (iv) chlorination of the 5-position of the imidazole ring with N-chlorosuccinimide in step 40-F was omitted. LC-MS: calcd for $C_{29}H_{27}IN_4O_4$ [M+H$^+$] 623. Found 623.

Example 41

(R)-3-{(S)-2-(4-Fluoro-phenyl)-1-[5-(4-iodo-phenyl)-1H-imidazol-2-yl]-ethyl}-5-[4-(2-hydroxy-ethoxy)-phenyl]-imidazolidine-2,4-dione

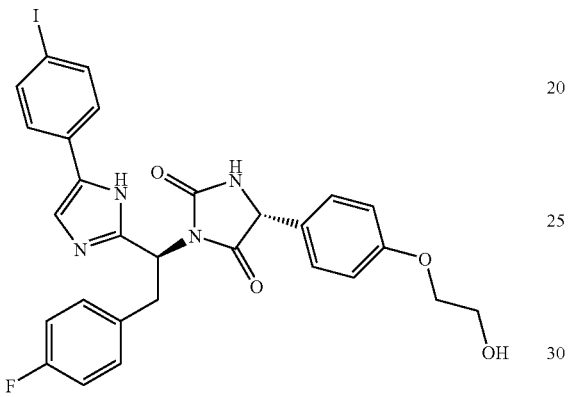

Prepared by the same method as described in example 1 except that (i) steps A, B, and C were omitted; (ii) commercially available 1-(4-iodo-phenyl)-ethanone was used in place of 1-(2-fluoro-4-iodo-phenyl)-ethanone in step 41-D; (iii) (S)-2-tert-butoxycarbonylamino-3-(4-fluoro-phenyl)-propionic acid was used in place of (2S,3S)-2-tert-butoxycarbonylamino-3-phenyl-butyric acid in step 41-E and (iv) chlorination of the 5-position of the imidazole ring with N-chlorosuccinimide in step 41-F was omitted. HR-MS: calcd for $C_{28}H_{24}FIN_4O_4$ [M+H$^+$] 627.0899. Found 627.0904.

Example 42

2-((R)-1-{(1S,2S)-1-[5-(4-Iodo-phenyl)-1H-imidazol-2-yl]-2-phenyl-propyl}-2,5-dioxo-imidazolidin-4-yl)-N-(2-vinyloxy-ethoxy)-acetamide

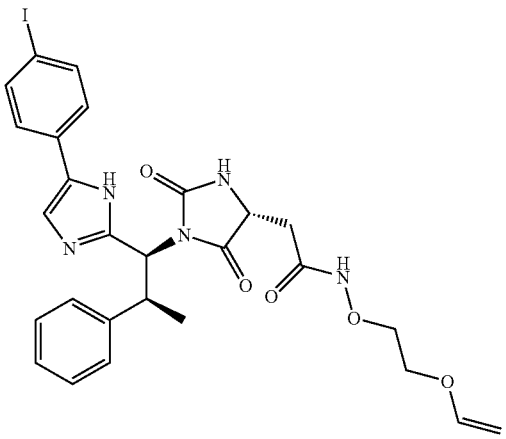

Prepared by the same method as described in example 9 except that step 42-O was omitted. HR-MS: calcd for $C_{27}H_{28}IN_5O_5$ [M+H$^+$] 630. Found 630.

Example 43

(R)-3-{(S)-1-[4-Chloro-5-(4-iodo-phenyl)-1H-imidazol-2-yl]-2-phenyl-ethyl}-5-[4-(2-hydroxy-ethoxy)-phenyl]-imidazolidine-2,4-dione

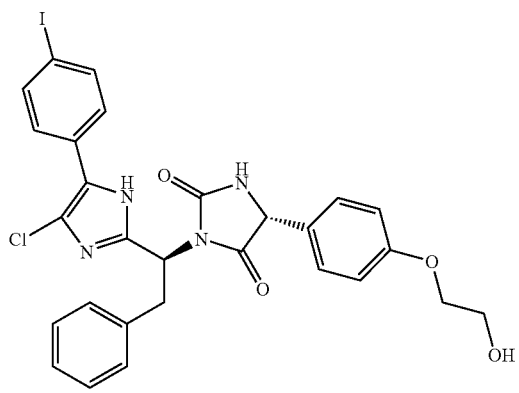

Prepared by the same method as described in example 1 except that (i) steps A, B, and C were omitted; (ii) commercially available 1-(4-iodo-phenyl)-ethanone was used in place of 1-(2-fluoro-4-iodo-phenyl)-ethanone in step 43-D and (iii) (S)-2-tert-butoxycarbonylamino-3-phenyl-propionic acid was used in place of (2S,3S)-2-tert-butoxycarbonylamino-3-phenyl-butyric acid in step 43-E. HR-MS: calcd for $C_{28}H_{24}ClIN_4O_4$ [M+H$^+$] 643.0604. Found 643.0601.

Example 44

(R)-3-[5-(2-Fluoro-4-iodo-phenyl)-1H-imidazol-2-ylmethyl]-5-[4-(2-hydroxy-ethoxy)-phenyl]-imidazolidine-2,4-dione

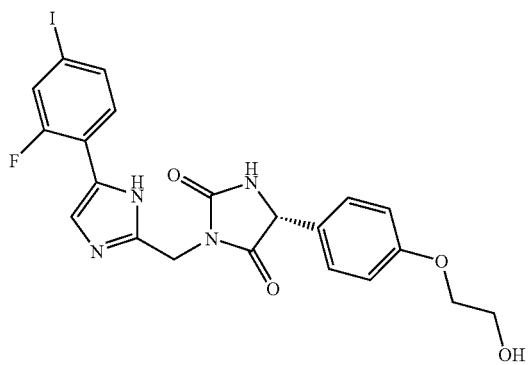

Prepared by the same method as described in example 22 except that in step 44-E tert-butoxycarbonylamino-acetic acid was used in place of (2S,3S)-2-tert-butoxycarbonylamino-3-methyl-pentanoic acid. HR-MS: calcd for $C_{21}H_{18}FIN_4O_4$ [M+H$^+$] 537.0430. Found 537.0428.

Example 45

(R)-3-{(S)-1-[5-(2-Fluoro-4-iodo-phenyl)-1H-imidazol-2-yl]-ethyl}-5-[4-(2-hydroxy-ethoxy)-phenyl]-imidazolidine-2,4-dione

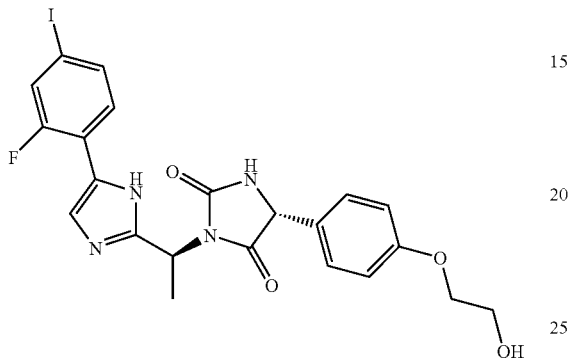

Prepared by the same method as described in example 44 except that in step 45-E (S)-2-tert-butoxycarbonylamino-propionic acid was used in place of tert-butoxycarbonylamino-acetic. HR-MS: calcd for $C_{22}H_{20}FIN_4O_4$ [M+H$^+$] 551.0586. Found 551.0594.

Example 46

(R)-5-[4-((R)-2,3-Dihydroxy-propoxy)-phenyl]-3-{(S)-1-[5-(2-fluoro-4-iodo-phenyl)-1H-imidazol-2-yl]-ethyl}-imidazolidine-2,4-dione

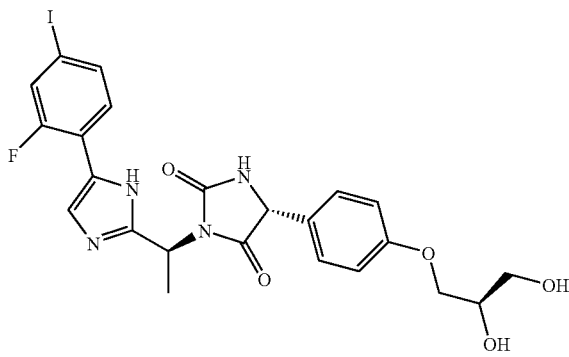

Prepared by the same method as described in example 45 except that in step 46-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{23}H_{22}FIN_4O_5$ [M+H$^+$] 581.0692. Found 581.0691.

Example 47

(R)-3-{(S)-1-[5-(2-Fluoro-4-iodo-phenyl)-1H-imidazol-2-yl]-2-methyl-propyl}-5-[4-(2-hydroxy-ethoxy)-phenyl]-imidazolidine-2,4-dione

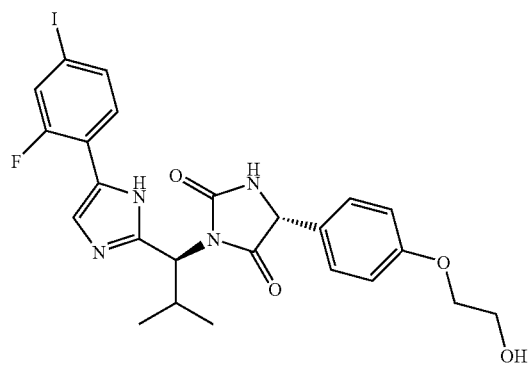

Prepared by the same method as described in example 44 except that in step 47-E (S)-2-tert-butoxycarbonylamino-3-methylbutyric acid was used in place of tert-butoxycarbonylamino-acetic acid. HR-MS: calcd for $C_{24}H_{24}FIN_4O_4$ [M+H$^+$] 579.0899. Found 579.0898.

Example 48

(R)-3-{(S)-1-[5-(2-Fluoro-4-iodo-phenyl)-1H-imidazol-2-yl]-3-methyl-butyl}-5-[4-(2-hydroxy-ethoxy)-phenyl]-imidazolidine-2,4-dione

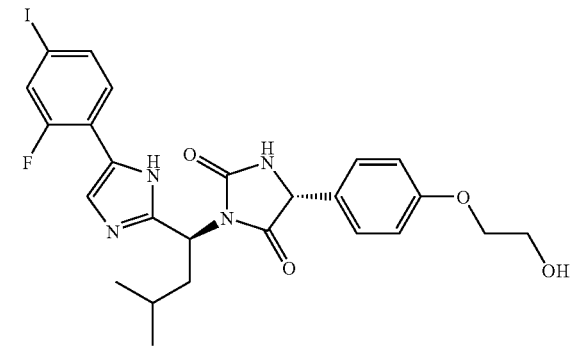

Prepared by the same method as described in example 1 except that (i) (S)-2-tert-butoxycarbonylamino-4-methyl-pentanoic acid was used in place of (2S,3S)-2-tert-butoxycarbonylamino-3-phenyl-butyric acid in step 48-E and (ii) chlorination of the 5-position of the imidazole ring with N-chlorosuccinimide in step 48-F was omitted. HR-MS: calcd for $C_{25}H_{26}FIN_4O_4$ [M+H$^+$] 593.1056. Found 593.1052.

Example 49

(R)-3-{(S)-2-Cyclohexyl-1-[5-(2-fluoro-4-iodo-phenyl)-1H-imidazol-2-yl]-ethyl}-5-[4-(2-hydroxy-ethoxy)-phenyl]-imidazolidine-2,4-dione

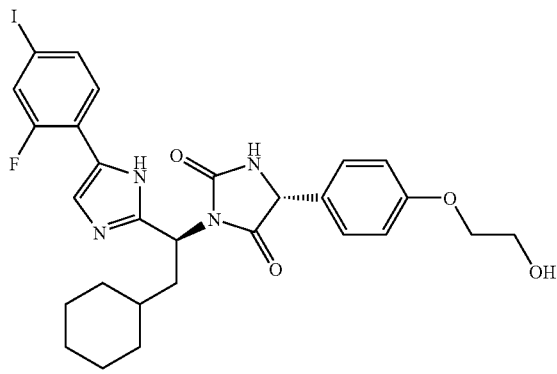

Prepared by the same method as described in example 1 except that (i) (S)-2-tert-butoxycarbonylamino-3-cyclohexyl-propionic acid was in place of (2S,3S)-2-tert-butoxycarbonylamino-3-phenyl-butyric acid in step 49-E and (ii) chlorination of the 5-position of the imidazole ring with N-chlorosuccinimide in step 49-F was omitted. HR-MS: calcd for $C_{28}H_{30}FIN_4O_4$ [M+H$^+$] 633.1369. Found 633.1364.

Example 50

(R)-3-{1-[5-(2-Fluoro-4-iodo-phenyl)-1H-imidazol-2-yl]-cyclopropyl}-5-[4-(2-hydroxy-ethoxy)-phenyl]-imidazolidine-2,4-dione

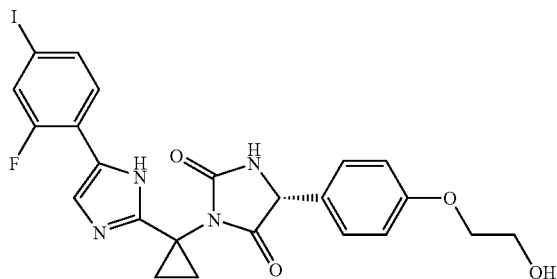

Prepared by the same method as described in example 44 except that in step 50-E 1-tert-butoxycarbonylamino-cyclopropanecarboxylic acid was used in place of tert-butoxycarbonylamino-acetic acid. HR-MS: calcd for $C_{23}H_{20}FIN_4O_4$ [M+H$^+$] 563.0586. Found 563.0588.

Example 51

5-[4-((R)-2,3-Dihydroxy-propoxy)-phenyl]-3-{(1R,2R)-1-[5-(2-fluoro-4-iodo-phenyl)-1H-imidazol-2-yl]-2-methoxy-propyl}-imidazolidine-2,4-dione

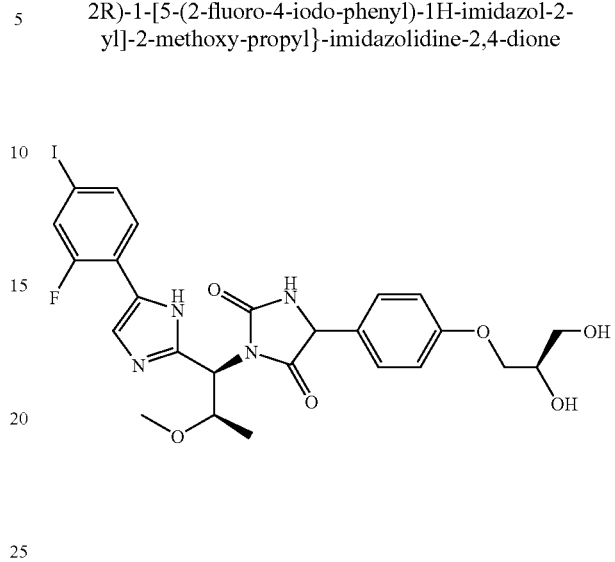

Prepared by the same method as described in example 46 except that in step 51-E (2S,3R)-2-tert-butoxycarbonylamino-3-methoxy-butyric acid was used in place of (S)-2-tert-butoxycarbonylamino-propionic acid. Following chromatographic purification the final product was found to have isomerized to a 1:1 mixture of isomers at the 5-position of the imidazolidine-2,4-dione ring. HR-MS: calcd for $C_{25}H_{26}FIN_4O_6$ [M+H$^+$] 625.0954. Found 625.0956.

Example 52

(R)-3-{(S)-1-[5-(2-Fluoro-4-iodo-phenyl)-1H-imidazol-2-yl]-2-phenyl-ethyl}-5-[4-(2-hydroxy-ethoxy)-phenyl]-imidazolidine-2,4-dione

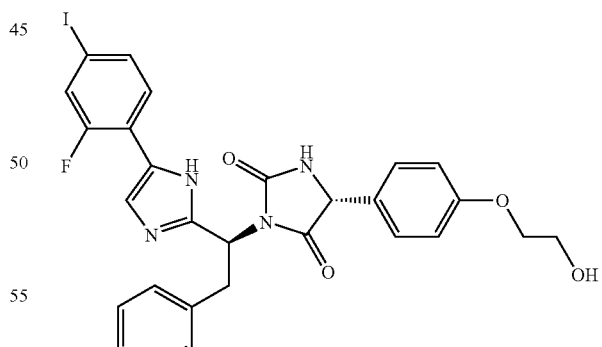

Prepared by the same method as described in example 1 except that (i) (S)-2-tert-butoxycarbonylamino-3-phenyl-propionic acid was in place of (2S,3S)-2-tert-butoxycarbonylamino-3-phenyl-butyric acid in step 52-E and (ii) chlorination of the 5-position of the imidazole ring with N-chlorosuccinimide in step 52-F was omitted. HR-MS: calcd for $C_{28}H_{24}FIN_4O_4$ [M+H$^+$] 627.0899. Found 627.0903.

Example 53

(R)-3-{(S)-1-[5-(2-Fluoro-4-iodo-phenyl)-1H-imidazol-2-yl]-2-phenyl-ethyl}-5-[4-(2-methoxy-ethoxy)-phenyl]-imidazolidine-2,4-dione

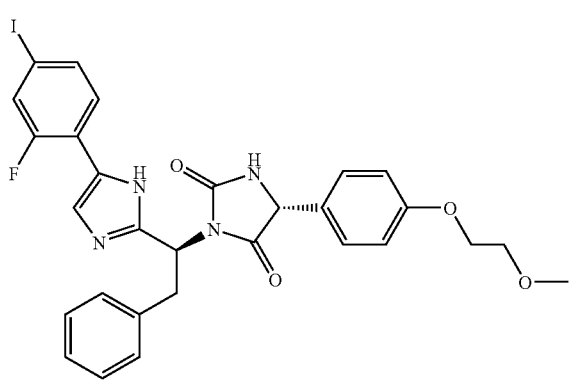

Prepared by the same method as described in example 1 except that (i) (2S)-2-tert-butoxycarbonylamino-3-phenyl-propionic acid was used in place of (2S,3S)-2-tert-butoxycarbonylamino-3-phenyl-butyric acid in step 53-E; (ii) chlorination of the 5-position of the imidazole ring with N-chlorosuccinimide in step 53-F was omitted and (iii) (R)-tert-butoxycarbonylamino-[4-(2-methoxy-ethoxy)-phenyl]-acetic acid was used in place of (R)-tert-butoxycarbonylamino-[4-(2-tert-butoxy-ethoxy)-phenyl]-acetic acid in step 53-G. (R)-tert-Butoxycarbonylamino-[4-(2-methoxy-ethoxy)-phenyl]-acetic acid was prepared as described in example 1 for the preparation of (R)-tert-butoxycarbonylamino-[4-(2-tert-butoxy-ethoxy)-phenyl]-acetic acid except that 1-bromo-2-methoxy-ethane was used in place of 2-(2-iodo-ethoxy)-2-methyl-propane. HR-MS: calcd for $C_{29}H_{26}FIN_4O_4$ [M+H$^+$] 641.1056. Found 641.1053.

Example 54

(R)-5-[4-((R)-2,3-Dihydroxy-propoxy)-phenyl]-3-{(S)-1-[5-(2-fluoro-4-iodo-phenyl)-1H-imidazol-2-yl]-2-phenyl-ethyl}-imidazolidine-2,4-dione

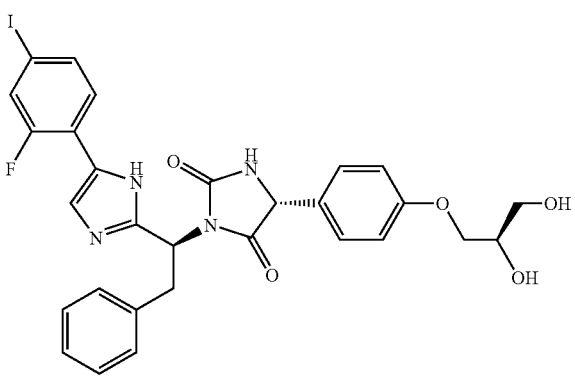

Prepared by the same method as described in example 33 except that (S)-2-tert-butoxycarbonylamino-3-phenyl-propionic acid was used in place of (S)-2-tert-butoxycarbonylamino-3-methyl-butyric acid in step 54-E. HR-MS: calcd for $C_{29}H_{26}FIN_4O_5$ [M+H$^+$] 657.1005. Found 657.1005.

Example 55

(R)-3-{(1S,2S)-1-[5-(2-Fluoro-4-iodo-phenyl)-1H-imidazol-2-yl]-2-phenyl-propyl}-5-[4-(2-hydroxy-ethoxy)-phenyl]-imidazolidine-2,4-dione

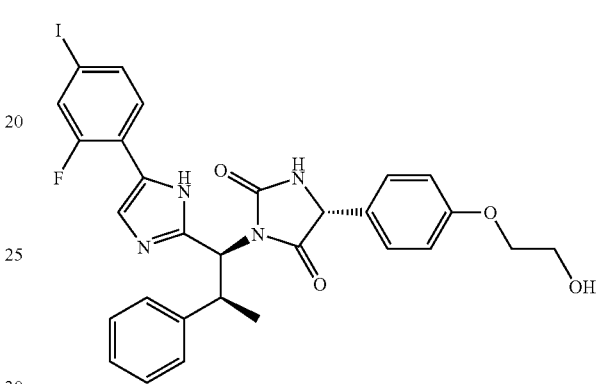

Prepared by the same method as described in example 1 except that chlorination of the 5-position of the imidazole ring with N-chlorosuccinimide in step 55-F was omitted. HR-MS: calcd for $C_{29}H_{26}FIN_4O_4$ [M+H$^+$] 641.1056. Found 641.1052.

Example 56

(R)-3-{(1S,2S)-1-[5-(2-Fluoro-4-iodo-phenyl)-1H-imidazol-2-yl]-2-phenyl-propyl}-5-[4-(2-methoxy-ethoxy)-phenyl]-imidazolidine-2,4-dione

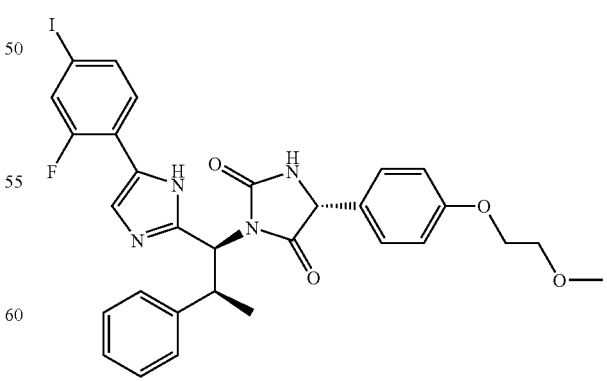

Prepared by the same method as described in example 53 except (2S,3S)-2-tert-butoxycarbonylamino-3-phenyl-butyric acid was used in place of (2S)-2-tert-butoxycarbonylamino-3-phenyl-propionic acid. HR-MS: calcd for $C_{30}H_{28}FIN_4O_4$ [M+H$^+$] 655.1212. Found 655.1215.

Example 57

(R)-3-{(1S,2S)-1-[5-(2-Fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione

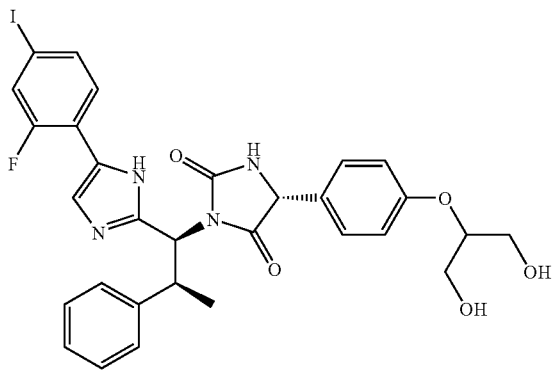

Prepared by the same method as described in example 1 except that (i) chlorination of the 5-position of the imidazole ring with N-chlorosuccinimide in step 57-F was omitted and (ii) (R)-tert-butoxycarbonylamino-[4-(2-hydroxy-1-hydroxymethyl-ethoxy)-phenyl]-acetic acid (prepared as described below in steps 57-V, 57-W and 57-X) was used in place of (R)-tert-butoxycarbonylamino-[4-(2-tert-butoxy-ethoxy)-phenyl]-acetic acid in step 57-G.

Step 57-V: To a solution of 1,3-bis-benzyloxy-propan-2-ol (3.07 g, 11.27 mmol) in dichloromethane (60 mL) at 0° C. under an atmosphere of nitrogen were added triethylamine (3.14 mL, 22.54 mmol), dimethyl-pyridin-4-yl-amine (0.68 g, 5.57 mmol) and 2,5-dichlorosulfonyl chloride (3.32 g, 13.52 mmol) and the mixture left to stir and warm slowly to ambient temperature overnight. The reaction mixture was diluted with dichloromethane and washed with water. The aqueous layer was separated and washed once with dichloromethane. The combined organic layers were washed with saturated aqueous sodium hydrogen carbonate solution (once), brine (once), dried over sodium sulfate, filtered and concentrated in vacuo. The residue was purified by chromatography over silica gel eluted with 10% v/v ethyl acetate in hexanes to give 2,5-dichloro-benzenesulfonic acid 2-benzyloxy-1-benzyloxymethyl-ethyl ester as a white solid (4.20 g, 77%).

Step 57-W: To a stirred solution of (R)-tert-butoxycarbonylamino-(4-hydroxy-phenyl)-acetic acid (1.0 g, 3.74 mmol) in dry N,N-dimethylformamide (20 mL) at 0° C. under an atmosphere of nitrogen was added sodium hydride (60% suspension in mineral oil) (0.33 g, 8.23 mmol) and the mixture stirred at 0° C. for 15 minutes. 2,5-dichloro-benzenesulfonic acid 2-benzyloxy-1-benzyloxymethyl-ethyl ester (2.20 g, 4.57 mmol) was added to the reaction mixture to form a yellow solution which was stirred at ambient temperature for 5 minutes before warming to 100° C. for 10 minutes. The reaction mixture which by now contained a heavy precipitate was cooled to ambient temperature, diluted with ethyl acetate, cooled to 0° C. and treated with an equal volume of water. The stirred mixture was acidified to pH≈4 with 1 M aqueous hydrochloric acid. The organic layer was separated and the aqueous layer extracted with ethyl acetate. The combined organic layers were washed with water (three times), dried over sodium sulfate, filtered through a thin pad of silica gel and concentrated in vacuo to give (R)-[4-(2-benzyloxy-1-benzyloxymethyl-ethoxy)-phenyl]-tert-butoxycarbonylamino-acetic acid (1.20 g, 80%).

Step 57-X: A hydrogenation vessel containing a solution of (R)-[4-(2-benzyloxy-1-benzyloxymethyl-ethoxy)-phenyl]-tert-butoxycarbonylamino-acetic acid (3.86 g, 7.4 mmol) in methanol (30 mL) was purged with nitrogen and 10% palladium on carbon (300 mg) added. The atmosphere above the methanol solution was exchanged for hydrogen and the reaction mixture stirred vigorously for 30 minutes at ambient temperature. The reaction mixture was filtered through a pad of celite and concentrated in vacuo to give (R)-tert-butoxycarbonylamino-[4-(2-hydroxy-1-hydroxymethyl-ethoxy)-phenyl]-acetic acid which was used without additional purification (2.43 g, 96%). HR-MS: calcd for $C_{30}H_{28}FIN_4O_5$ [M+H$^+$] 671.1161. Found 671.1158.

Example 58

(R)-5-[4-((R)-2,3-Dihydroxy-propoxy)-phenyl]-3-{(S)-1-[5-(2-fluoro-4-iodo-phenyl)-1H-imidazol-2-yl]-2-thiazol-4-yl-ethyl}-imidazolidine-2,4-dione

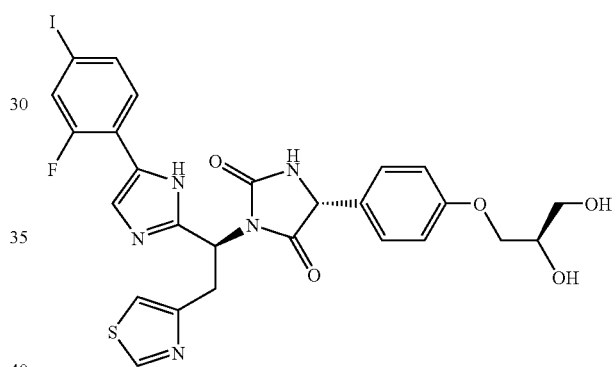

Prepared by the same method as described in example 46 except that in step 58-E (S)-2-tert-butoxycarbonylamino-3-thiazol-4-yl-propionic acid was used in place of (S)-2-tert-butoxycarbonylamino-propionic acid. HR-MS: calcd for $C_{26}H_{23}FIN_5O_5S$ [M+H$^+$] 664.0522. Found 654.0522.

Example 59

(R)-3-{(S)-1-[5-(2-Fluoro-4-iodo-phenyl)-4-methyl-1H-imidazol-2-yl]-2-methyl-propyl}-5-[4-(2-hydroxy-ethoxy)-phenyl]-imidazolidine-2,4-dione

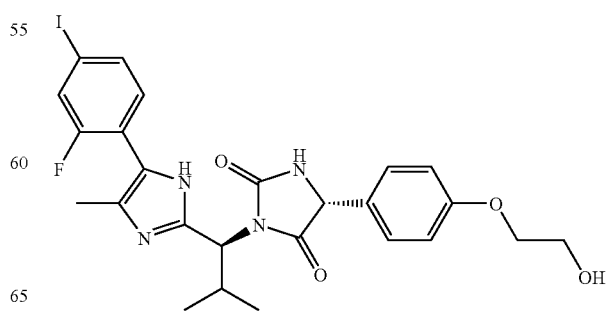

Prepared by the same method as described in example 1 except that (i) steps A, B and C were omitted; (ii) 1-(2-fluoro-4-iodo-phenyl)-propan-1-one (prepared as described in example 13) was used in place of 1-(2-fluoro-4-iodo-phenyl)-ethanone in step 59-D; (iii) (S)-2-tert-butoxycarbonylamino-3-methylbutyric acid was used in place of (2S,3S)-2-tert-butoxycarbonylamino-3-phenyl-butyric acid in step 59-E and (iv) chlorination of the 5-position of the imidazole ring with N-chlorosuccinimide in step 59-F was omitted. HR-MS: calcd for $C_{25}H_{26}FIN_4O_4$ [M+H$^+$] 593.1056. Found 593.1052.

Example 60

(R)-5-[4-((R)-2,3-Dihydroxy-propoxy)-phenyl]-3-{(S)-1-[5-(2-fluoro-4-iodo-phenyl)-4-methyl-1H-imidazol-2-yl]-2-methyl-propyl}-imidazolidine-2,4-dione

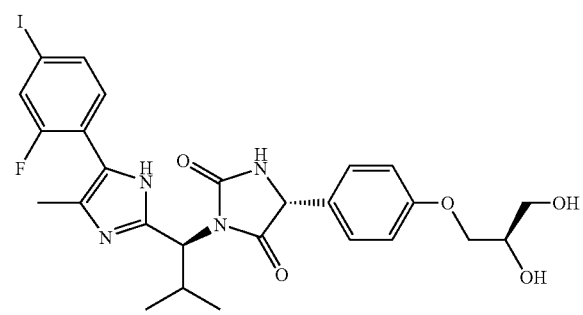

Prepared by the same method as described in example 59 except that in step 60-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{26}H_{28}FIN_4O_5$ [M+H$^+$] 623.1161. Found 623.1160.

Example 61

(R)-3-{(1S,2S)-1-[5-(2-Fluoro-4-iodo-phenyl)-4-methyl-1H-imidazol-2-yl]-2-methyl-butyl}-5-[4-(2-hydroxy-ethoxy)-phenyl]-imidazolidine-2,4-dione

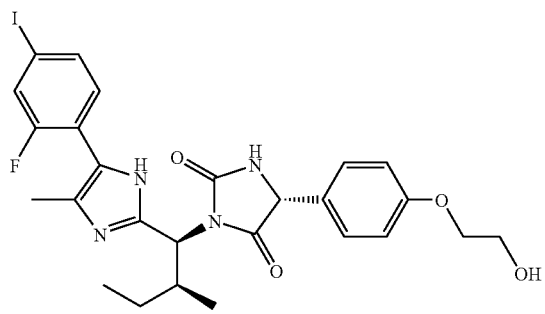

Prepared by the same method as described in example 59 except that in step 61-E (2S,3S)-2-tert-butoxycarbonylamino-3-methyl-pentanoic acid was used in place of (S)-2-tert-butoxycarbonylamino-3-methyl-butyric acid. HR-MS: calcd for $C_{26}H_{28}FIN_4O_4$ [M+H$^+$] 607.1212. Found 607.1211.

Example 62

(R)-5-[4-((R)-2,3-Dihydroxy-propoxy)-phenyl]-3-{(1S,2S)-1-[5-(2-fluoro-4-iodo-phenyl)-4-methyl-1H-imidazol-2-yl]-2-methyl-butyl}-imidazolidine-2,4-dione

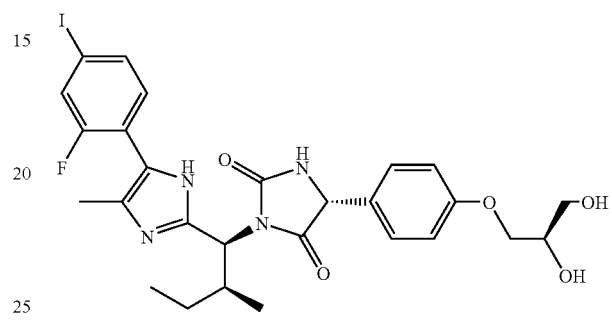

Prepared by the same method as described in example 60 except that in step 62-E (2S,3S)-2-tert-butoxycarbonylamino-3-methyl-pentanoic acid was used in place of (S)-2-tert-butoxycarbonylamino-3-methylbutyric acid. HR-MS: calcd for $C_{27}H_{30}FIN_4O_5$ [M+H$^+$] 637.1318. Found 637.1316.

Example 63

(R)-3-{(1R,2R)-1-[5-(2-Fluoro-4-iodo-phenyl)-4-methyl-1H-imidazol-2-yl]-2-methoxy-propyl}-5-[4-(2-hydroxy-ethoxy)-phenyl]-imidazolidine-2,4-dione

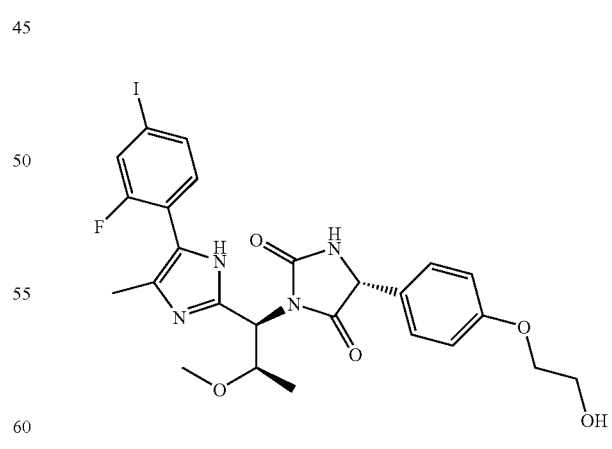

Prepared by the same method as described in example 59 except that in step 63-E (2S,3R)-2-tert-butoxycarbonylamino-3-methoxy-butyric acid was used in place of (S)-2- tert-butoxycarbonylamino-3-methylbutyric acid. HR-MS: calcd for $C_{25}H_{26}FIN_4O_5$ [M+H$^+$] 609.1005. Found. 609.1006.

Example 64

(R)-5-[4-((R)-2,3-Dihydroxy-propoxy)-phenyl]-3-{(1R,2R)-1-[5-(2-fluoro-4-iodo-phenyl)-4-methyl-1H-imidazol-2-yl]-2-methoxy-propyl}-imidazolidine-2,4-dione

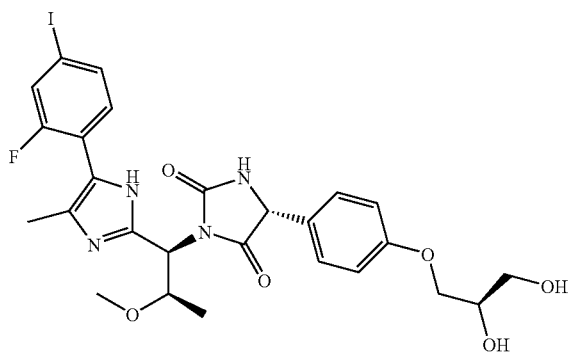

Prepared by the same method as described in example 60 except that in step 64-E (2S,3R)-2-tert-butoxycarbonylamino-3-methoxy-butyric acid was used in place of (S)-2-tert-butoxycarbonylamino-3-methylbutyric acid. HR-MS: calcd for $C_{26}H_{28}FIN_4O_6$, [M+H$^+$] 639.1111. Found. 639.1109.

Example 65

(R)-3-{(S)-1-[5-(2-Fluoro-4-iodo-phenyl)-4-methyl-1H-imidazol-2-yl]-2-phenyl-ethyl}-5-[4-(2-hydroxy-ethoxy)-phenyl]-imidazolidine-2,4-dione

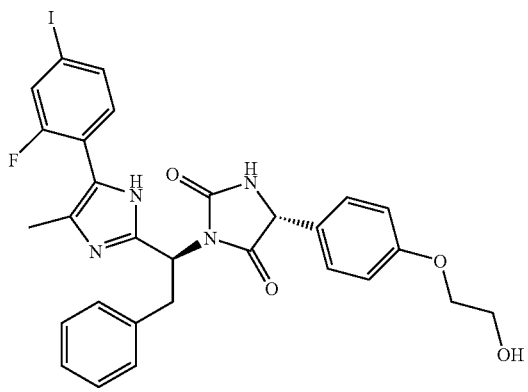

Prepared by the same method as described in example 59 except that in step 65-E (S)-2-tert-butoxycarbonylamino-3-phenyl-propionic acid was used in place of (S)-2-tert-butoxy-carbonylamino-3-methylbutyric acid. HR-MS: calcd for $C_{29}H_{26}FIN_4O_4$ [M+H$^+$] 641.1056. Found. 641.1053.

Example 66

(R)-5-[4-((R)-2,3-Dihydroxy-propoxy)-phenyl]-3-{(S)-1-[5-(2-fluoro-4-iodo-phenyl)-4-methyl-1H-imidazol-2-yl]-2-phenyl-ethyl}-imidazolidine-2,4-dione

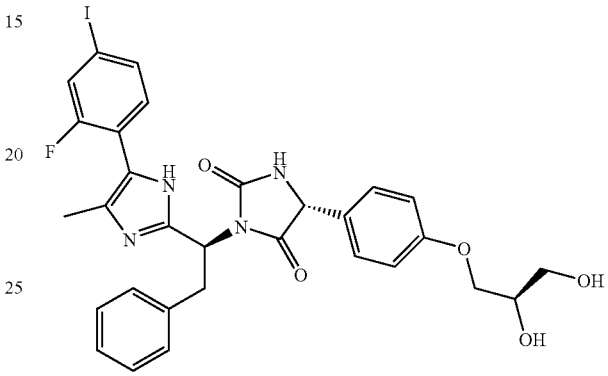

Prepared by the same method as described in example 60 except that in step 66-E (S)-2-tert-butoxycarbonylamino-3-phenyl-propionic acid was used in place of (S)-2-tert-butoxycarbonylamino-3-methylbutyric acid. HR-MS: calcd for $C_{30}H_{28}FIN_4O_5$ [M+H$^+$] 671.1161. Found. 671.1156.

Example 67

(R)-5-Cyclopropyl-3-{(1S,2S)-1-[5-(2-fluoro-4-iodo-phenyl)-4-methyl-1H-imidazol-2-yl]-2-phenyl-propyl}-imidazolidine-2,4-dione

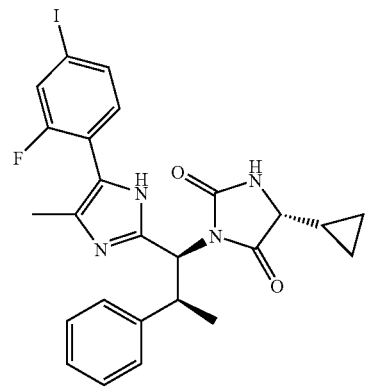

Prepared by the same method as described in example 13 except that in step 67-G commercially available (R)-tert-butoxycarbonylamino-cyclopropyl-acetic acid was used in place of (R)-2-tert-butoxycarbonylamino-3-cyclopropyl-propionic acid. HR-MS: calcd for $C_{25}H_{24}FIN_4O_2$ [M+H$^+$] 559.1001. Found 559.0997.

Example 68

(R)-3-{(1S,2S)-1-[5-(2-Fluoro-4-iodo-phenyl)-4-methyl-1H-imidazol-2-yl]-2-phenyl-propyl}-5-[4-(2-hydroxy-ethoxy)-phenyl]-imidazolidine-2,4-dione

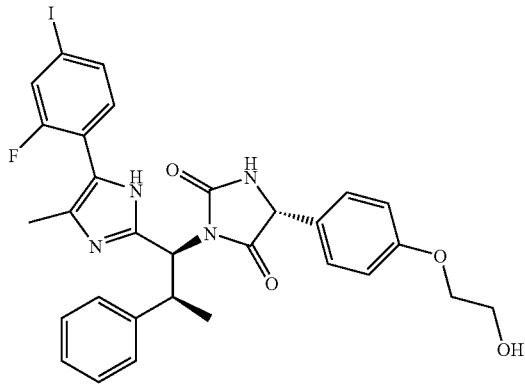

Prepared by the same method as described in example 1 except that (i) steps A, B and C were omitted; (ii) 1-(2-fluoro-4-iodo-phenyl)-propan-1-one (prepared as described in example 13) was used in place of 1-(2-fluoro-4-iodo-phenyl)-ethanone in step 68-D and (iii) chlorination of the 5-position of the imidazole ring with N-chlorosuccinimide in step 68-F was omitted. HR-MS: calcd for $C_{30}H_{28}FIN_4O_4$ [M+H$^+$] 655.1212. Found. 655.1210.

Example 69

(R)-5-[4-((R)-2,3-Dihydroxy-propoxy)-phenyl]-3-{(1S,2S)-1-[5-(2-fluoro-4-iodo-phenyl)-4-methyl-1H-imidazol-2-yl]-2-phenyl-propyl}-imidazolidine-2,4-dione

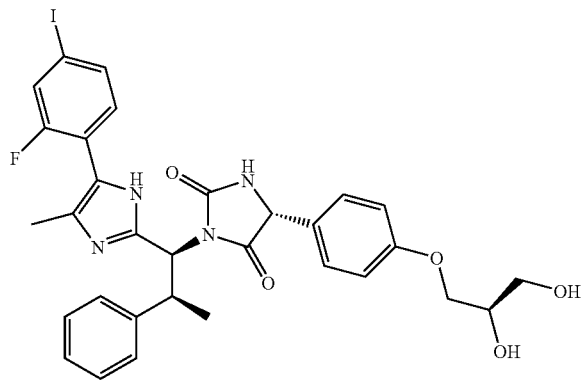

Prepared by the same method as described in example 68 except that in step 69-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{31}H_{30}FIN_4O_5$ [M+H$^+$] 685.1318. Found. 685.1317.

Example 70

(R)-5-[4-((S)-2,3-Dihydroxy-propoxy)-phenyl]-3-{(1S,2S)-1-[5-(2-fluoro-4-iodo-phenyl)-4-methyl-1H-imidazol-2-yl]-2-phenyl-propyl}-imidazolidine-2,4-dione

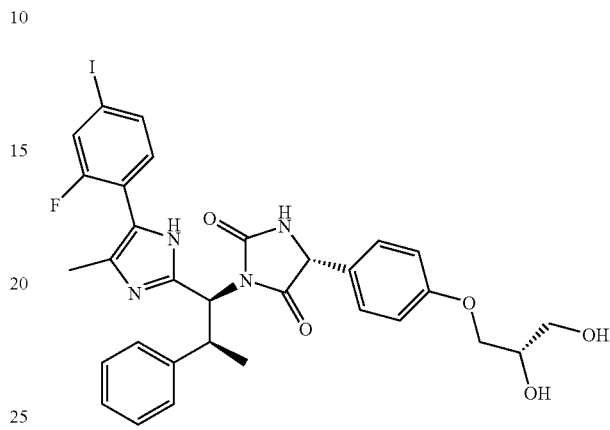

Prepared by the same method as described in example 68 except that in step 70-G (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-(2-tert-butoxy-ethoxy)-phenyl]-acetic acid. (R)-tert-Butoxycarbonylamino-[4-((R)-2,2-dimethyl-[1,3]dioxolan-4-ylmethoxy)-phenyl]-acetic acid was prepared as described in steps 33-T and 33-U except that in step 70-T (R)-2,2-dimethyl-1,3-dioxolane-4-methanol was used in place of (S)-2,2-dimethyl-1,3-dioxolane-4-methanol. HR-MS: calcd for $C_{31}H_{30}FIN_4O_5$ [M+H$^+$] 685.1318. Found 685.1322.

Example 71

(R)-3-{(1S,2S)-1-[5-(2-Fluoro-4-iodo-phenyl)-4-methyl-1H-imidazol-2-yl]-2-phenyl-propyl}-5-[4-(2-hydroxy-1-hydroxymethyl-ethoxy)-phenyl]-imidazolidine-2,4-dione

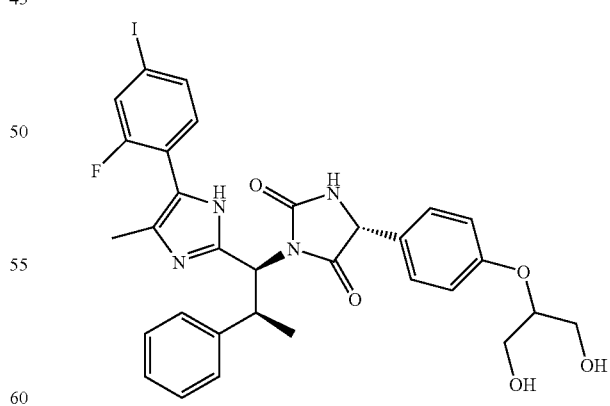

Prepared by the same method as described in example 68 except that (R)-tert-butoxycarbonylamino-[4-(2-hydroxy-1-hydroxymethyl-ethoxy)-phenyl]-acetic acid (prepared as described in steps 57-V, 57-W and 57-X) was used in place of (R)-tert-butoxycarbonylamino-[4-(2-tert-butoxy-ethoxy)-phenyl]-acetic acid in step 71-G. HR-MS: calcd for $C_{31}H_{30}FIN_4O_5$ [M+H$^+$] 685.1318. Found 685.1321.

Example 72

2-[4-((R)-1-{(1S,2S)-1-[5-(2-Fluoro-4-iodo-phenyl)-4-methyl-1H-imidazol-2-yl]-2-phenyl-propyl}-2,5-dioxo-imidazolidin-4-yl)-phenoxy]-N,N-dimethyl-acetamide

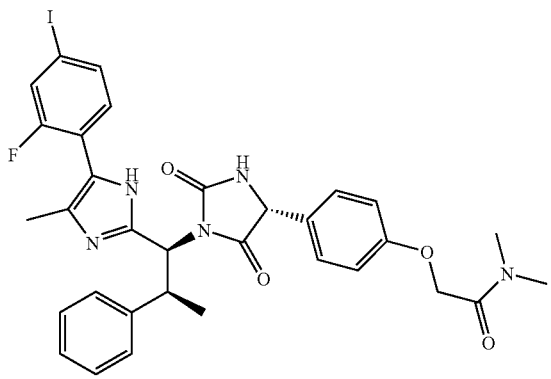

Prepared by the same method as described in example 1 except that (i) steps A, B and C were omitted; (ii) 1-(2-fluoro-4-iodo-phenyl)-propan-1-one (prepared as described in example 13) was used in place of 1-(2-fluoro-4-iodo-phenyl)-ethanone in step 72-D; (iii) chlorination of the 5-position of the imidazole ring with N-chlorosuccinimide in step 72-F was omitted and (iv) (R)-tert-butoxycarbonylamino-(4-dimethylcarbamoylmethoxy-phenyl)-acetic acid (prepared as described in example 6) was used in place of (R)-tert-butoxycarbonylamino-[4-(2-tert-butoxy-ethoxy)-phenyl]-acetic acid in step 72-G. HR-MS: calcd for $C_{32}H_{31}FIN_5O_4$ [M+H$^+$] 696.1478. Found 696.1475.

Example 73

(R)-3-{(1S,2S)-1-[4-Chloro-5-(2-fluoro-4-iodo-phenyl)-1H-imidazol-2-yl]-2-phenyl-propyl}-5-[4-((R)-2,3-dihydroxy-propoxy)-phenyl]-imidazolidine-2,4-dione

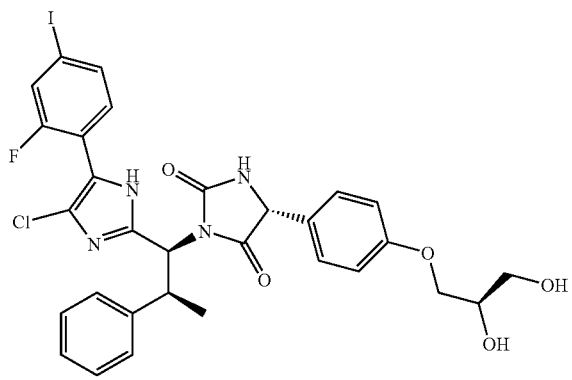

Prepared by the same method as described in example 1 except that (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid in step 73-G. HR-MS: calcd for $C_{30}H_{27}ClFIN_4O_5$ [M+H$^+$] 705.0772. Found 705.0768.

Example 74

(R)-3-{(1S,2S)-1-[4-Chloro-5-(2-fluoro-4-iodo-phenyl)-1H-imidazol-2-yl]-2-phenyl-propyl}-5-[4-((S)-2,3-dihydroxy-propoxy)-phenyl]-imidazolidine-2,4-dione

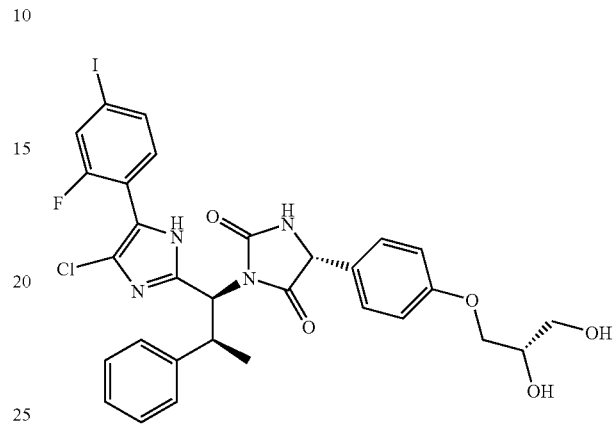

Prepared by the same method as described in example 1 except that (i) (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-(2-tert-butoxy-ethoxy)-phenyl]-acetic acid in step 74-G and (ii) cyclization of (R)-2-amino-N-{(1S,2S)-1-[4-chloro-5-(2-fluoro-4-iodo-phenyl)-1H-imidazol-2-yl]-2-phenyl-propyl}-2-[4-((S)-2,3-dihydroxy-propoxy)-phenyl]-acetamide in step 74-H was performed as described in step 34-H. (R)-tert-Butoxycarbonylamino-[4-((R)-2,2-dimethyl-[1,3]dioxolan-4-ylmethoxy)-phenyl]-acetic acid was prepared as described in steps 33-T and 33-U except that in step 70-T (R)-2,2-dimethyl-1,3-dioxolane-4-methanol was used in place of (S)-2,2-dimethyl-1,3-dioxolane-4-methanol. HR-MS: calcd for $C_{30}H_{27}ClFIN_4O_5$ [M+H$^+$] 705.0772. Found 705.0771.

Example 75

(R)-3-{(1S,2S)-1-[4-Chloro-5-(2-fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione

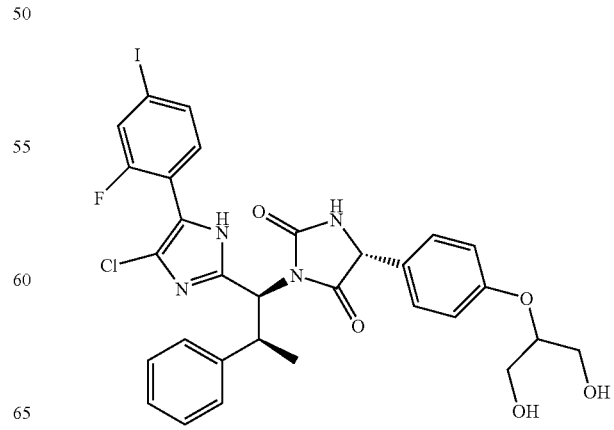

Prepared by the same method as described in example 1 except that (i) (R)-tert-butoxycarbonylamino-[4-(2-hydroxy-1-hydroxymethyl-ethoxy)-phenyl]-acetic acid (prepared as described in steps 57-V, 57-W and 57-X) was used in place of (R)-tert-butoxycarbonylamino-[4-(2-tert-butoxy-ethoxy)-phenyl]-acetic acid in step 75-G and (ii) cyclization of (R)-2-amino-N-{(1S,2S)-1-[4-chloro-5-(2-fluoro-4-iodo-phenyl)-1H-imidazol-2-yl]-2-phenyl-propyl}-2-[4-(2-hydroxy-1-hydroxymethyl-ethoxy)-phenyl]-acetamide in step 75-H was performed as described in step 34-H. HR-MS: calcd for $C_{30}H_{27}ClFIN_4O_5$ [M+H$^+$] 705.0772. Found 705.0772.

Example 76

(R)-3-{(1S,2S)-1-[5-(2,6-Difluoro-4-iodo-phenyl)-1H-imidazol-2-yl]-2-phenyl-propyl}-5-[4-(2-hydroxy-ethoxy)-phenyl]-imidazolidine-2,4-dione

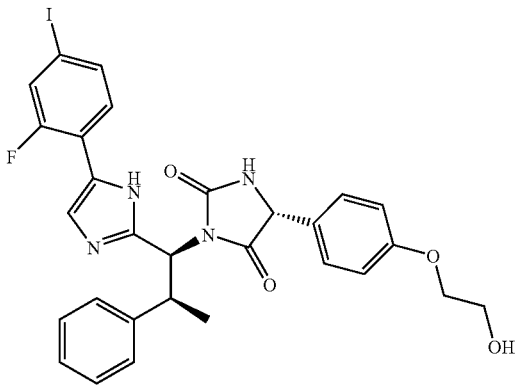

Prepared by the same method as described in example 1 except that (i) steps A, B and C were omitted; (ii) 1-(2,6-difluoro-4-iodo-phenyl)-ethanone (prepared according to the procedure described in steps 76-Y and step 76-Z below) was used in place of 1-(2-fluoro-4-iodo-phenyl)-ethanone in step 76-D; (iii) chlorination of the 5-position of the imidazole ring with N-chlorosuccinimide in step 76-F was omitted and (iv) following removal of the tert-butyl carbamate and tert-butyl ether protecting groups, the cyclization of (R)-2-amino-N-{(1S,2S)-1-[5-(2,6-difluoro-4-iodo-phenyl)-1H-imidazol-2-yl]-2-phenyl-propyl}-2-[4-(2-hydroxy-ethoxy)-phenyl]-acetamide in step 76-H was performed as described in step 34-H.

Step 76-X: To a solution of 2.5 M n-butyl lithium in hexanes (2 mL, 5.0 mmol) and tetrahydrofuran (20 mL) at –78° C. under an atmosphere of nitrogen was added dropwise tetramethylpiperidine (0.85 mL, 5.0 mmol). The resulting light yellow solution was stirred for approximately 15 minutes, then 1,3-difluoro-5-iodo-benzene (1 g, 4.17 mmol) was added dropwise. This solution was stirred at –78° C. for 1 hour, followed by the addition of acetaldehyde (0.70 mL, 12.5 mmol) via syringe. The reaction mixture was stirred at –78° C. for 10 minutes then allowed to warm to room temperature. TLC indicated the reaction to be complete. The reaction was quenched with saturated aqueous ammonium chloride solution (2 mL), diluted with water (50 mL) and extracted with ethyl acetate (2×30 mL). The combined organic layers were dried over sodium sulfate and concentrated in vacuo. The crude product was purified by chromatography over silica gel gradient eluted with 0 to 25% v/v ethyl acetate/hexanes to give 1-(2,6-difluoro-4-iodo-phenyl)-ethanol (561 mg, 47%).

Step 76-Y: To a solution of 1-(2,6-difluoro-4-iodo-phenyl)-ethanol (561 mg, 1.98 mmol) in methylene chloride (25 mL) cooled in an ice/water bath were added 2,2,6,6-tetramethylpiperidine-1-oxyl (TEMPO) (3 mg, 0.12 mmol), sodium hydrogen carbonate (75 mg, 0.89 mmol) and tetrabutylammonium bromide (19 mg, 0.06 mmol). To this resulting mixture was added a 5% aqueous sodium hypochlorite solution in a dropwise manner until TLC indicated the reaction to be complete. The reaction mixture was diluted with methylene chloride (50 mL) and brine (100 mL) and the organic layer separated. The organic layer was dried over sodium sulfate, filtered through a pad of silica gel and concentrated in vacuo to give 1-(2,6-difluoro-4-iodo-phenyl)-ethanone (526 mg, 94%). HR-MS: calcd for $C_{29}H_{25}F_2IN_4O_4$ [M+H$^+$] 659.0962. Found 659.0962.

Example 77

(R)-3-{(1S,2S)-1-[5-(2,6-Difluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione

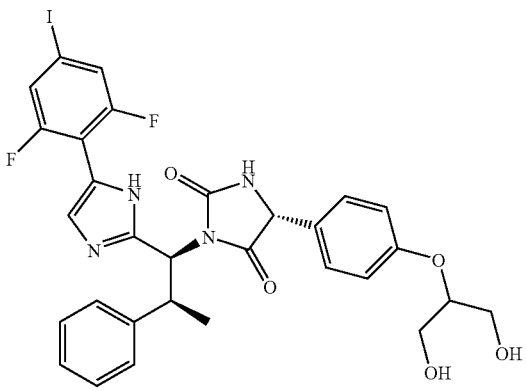

Prepared by the same method as described in example 1 except that (i) steps A, B and C were omitted; (ii) 1-(2,6-difluoro-4-iodo-phenyl)-ethanone (prepared as described in steps 76-Y and 76-Z) was used in place of 1-(2-fluoro-4-iodo-phenyl)-ethanone in step 76-D; (iii) chlorination of the 5-position of the imidazole ring with N-chlorosuccinimide in step 77-F was omitted; (iv) (R)-tert-butoxycarbonylamino-[4-(2-hydroxy-1-hydroxymethyl-ethoxy)-phenyl]-acetic acid (prepared as described in steps 57-V, 57-W and 57-X) was used in place of (R)-tert-butoxycarbonylamino-[4-(2-hydroxy-ethoxy)-phenyl]-acetic acid in step 77-G and (v) the cyclization of (R)-2-amino-N-{(1S,2S)-1-[5-(2,6-difluoro-4-iodo-phenyl)-1H-imidazol-2-yl]-2-phenyl-propyl}-2-[4-(2-hydroxy-1-hydroxymethyl-ethoxy)-phenyl]-acetamide in step 76-H was performed as described in step 34-H. HR-MS: calcd for $C_{30}H_{27}F_2IN_4O_5$ [M+H$^+$] 689.1067. Found 689.1068.

Example 78

(R)-3-[5-(2-Chloro-4-iodo-phenyl)-1H-imidazol-2-ylmethyl]-5-[4-(2-hydroxy-ethoxy)-phenyl]-imidazolidine-2,4-dione

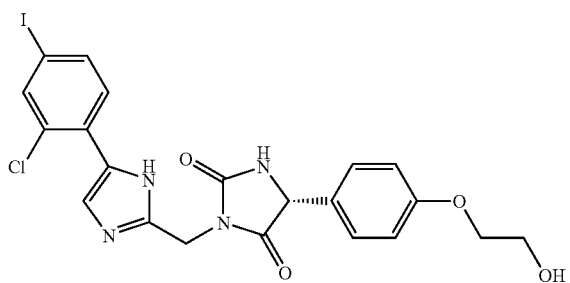

Prepared by the same method as described in example 44 except that in step 78-A 2-chloro-1,4-diiodo-benzene was used in place of 2-fluoro-1,4-diiodo-benzene. HR-MS: calcd for $C_{21}H_{18}ClIN_4O_4$ [M+H$^+$] 553.0134. Found 553.0132.

Example 79

(R)-3-{(S)-1-[5-(2-Chloro-4-iodo-phenyl)-1H-imidazol-2-yl]-ethyl}-5-[4-(2-hydroxy-ethoxy)-phenyl]-imidazolidine-2,4-dione

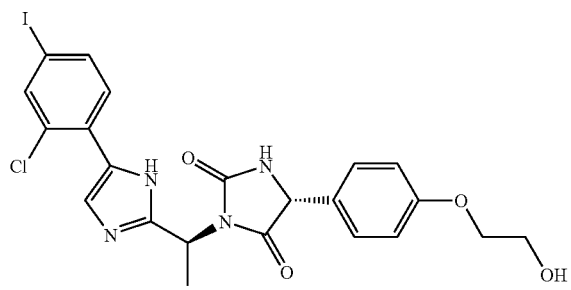

Prepared by the same method as described in example 35 except that in step 79-E (S)-2-tert-butoxycarbonylamino-propionic acid was used in place of (2S,3S)-2-tert-butoxycarbonylamino-3-phenyl-butyric acid. HR-MS: calcd for $C_{22}H_{20}ClIN_4O_4$ [M+H$^+$] 567.0291. Found 567.0293.

Example 80

(R)-3-{(S)-1-[5-(2-Chloro-4-iodo-phenyl)-1H-imidazol-2-yl]-butyl}-5-[4-(2-hydroxy-ethoxy)-phenyl]-imidazolidine-2,4-dione

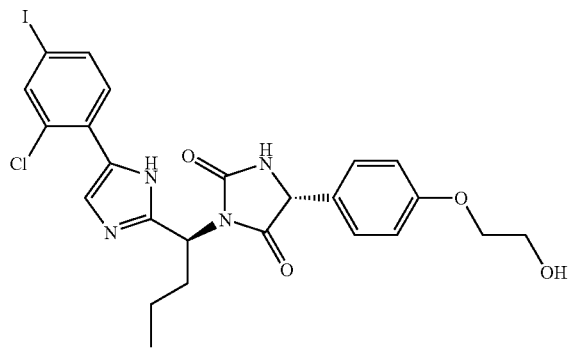

Prepared by the same method as described in example 1 except that (i) 2-chloro-1,4-diiodo-benzene was used in place of 2-fluoro-1,4-diiodo-benzene in step 80-A; (ii) (S)-2-tert-butoxycarbonylamino-pentanoic acid was used in place of (2S,3S)-2-tert-butoxycarbonylamino-3-phenyl-butyric acid in step 80-E; (iii) chlorination of the 5-position of the imidazole ring with N-chlorosuccinimide in step 80-F was omitted and (iv) removal of protecting groups and cyclization to form the hydantoin in step 80-H was performed as described in step 34-H. HR-MS: calcd for $C_{24}H_{24}ClIN_4O_4$ [M+H$^+$] 595.0604. Found 595.0603.

Example 81

(R)-3-{(S)-1-[5-(2-Chloro-4-iodo-phenyl)-1H-imidazol-2-yl]-pentyl}-5-[4-(2-hydroxy-ethoxy)-phenyl]-imidazolidine-2,4-dione

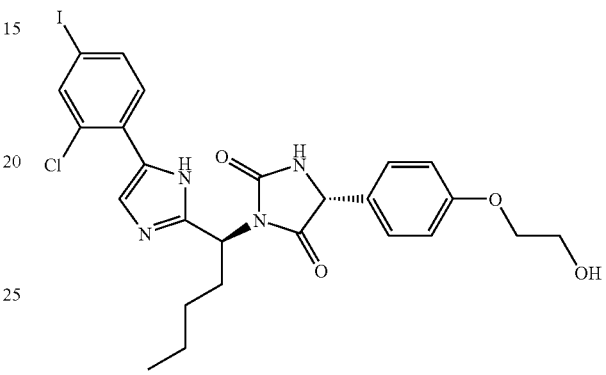

Prepared by the same method as described in example 80 except that (S)-2-tert-butoxycarbonylamino-hexanoic acid was used in place of (S)-2-tert-butoxycarbonylamino-pentanoic acid in step 81-E. HR-MS: calcd for $C_{25}H_{26}ClIN_4O_4$ [M+H$^+$] 609.0760. Found 609.0765.

Example 82

(R)-3-{(S)-1-[5-(2-Chloro-4-iodo-phenyl)-1H-imidazol-2-yl]-3-methyl-butyl}-5-[4-(2-hydroxy-ethoxy)-phenyl]-imidazolidine-2,4-dione

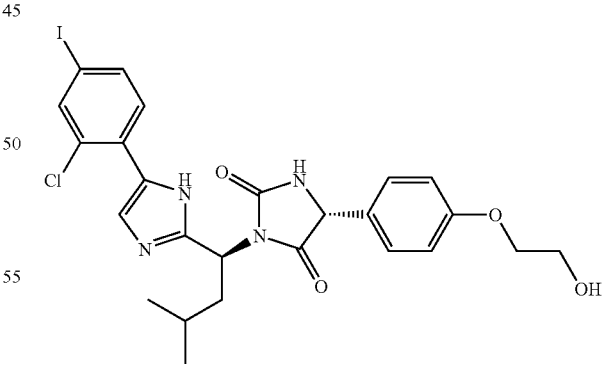

Prepared by the same method as described in example 1 except that (i) in step 82-A step 2-chloro-1,4-diiodo-benzene was used in place of 2-fluoro-1,4-diiodo-benzene; (ii) in step 82-E (S)-2-tert-butoxycarbonylamino-4-methyl-pentanoic acid was used in place of (2S,3S)-2-tert-butoxycarbonylamino-3-phenyl-butyric acid, and (ii) chlorination of the 5-position of the imidazole ring with N-chlorosuccinimide in step 82-F was omitted. HR-MS: calcd for $C_{25}H_{26}ClIN_4O_4$ [M+H$^+$] 609.0760. Found 609.0757.

Example 83

(R)-3-{(S)-1-[5-(2-Chloro-4-iodo-phenyl)-1H-imidazol-2-yl]-2-phenyl-ethyl}-5-[4-(2-hydroxy-ethoxy)-phenyl]-imidazolidine-2,4-dione

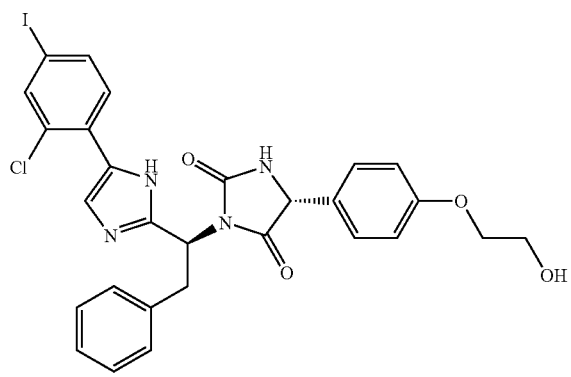

Prepared by the same method as described in example 78 except that in step 83-E (S)-2-tert-butoxycarbonylamino-3-phenyl-propionic acid was used in place of tert-butoxycarbonylamino-acetic acid. HR-MS: calcd for $C_{28}H_{24}ClIN_4O_4$ [M+H$^+$] 643.0604. Found 643.0602.

Example 84

(R)-3-{(S)-1-[5-(2-Chloro-4-iodo-phenyl)-1H-imidazol-2-yl]-2-phenyl-ethyl}-5-[4-((R)-2,3-dihydroxy-propoxy)-phenyl]-imidazolidine-2,4-dione

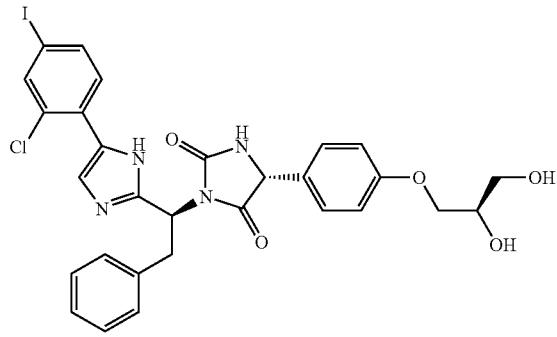

Prepared by the same method as described in example 37 except that in step 84-E (S)-2-tert-butoxycarbonylamino-3-phenyl-propionic acid was used in place of (2S,3S)-2-tert-butoxycarbonylamino-3-phenyl-butyric acid. HR-MS: calcd for $C_{29}H_{26}ClIN_4O_5$ [M+H$^+$] 673.0709. Found 673.0705.

Example 85

2-[4-((R)-1-{(S)-1-[5-(2-Chloro-4-iodo-phenyl)-1H-imidazol-2-yl]-2-phenyl-ethyl}-2,5-dioxo-imidazolidin-4-yl)-phenoxy]-N,N-dimethyl-acetamide

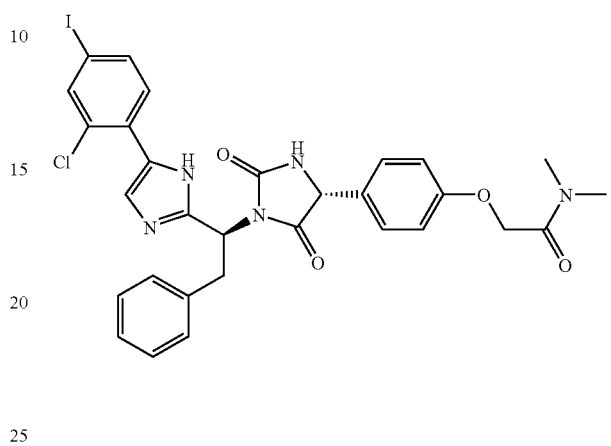

Prepared by the same method as described in example 83 except that in step 85-G (R)-tert-butoxycarbonylamino-(4-dimethylcarbamoylmethoxy-phenyl)-acetic acid (prepared as described in example 6) was used in place of (R)-tert-butoxycarbonylamino-[4-(2-tert-butoxy-ethoxy)-phenyl]-acetic acid. HR-MS: calcd for $C_{30}H_{27}ClIN_5O_4$ [M+H$^+$] 684.0869. Found 684.0870.

Example 86

(R)-3-{(1S,2S)-1-[5-(2-Chloro-4-iodo-phenyl)-1H-imidazol-2-yl]-2-phenyl-propyl}-5-cyclopropyl-imidazolidine-2,4-dione

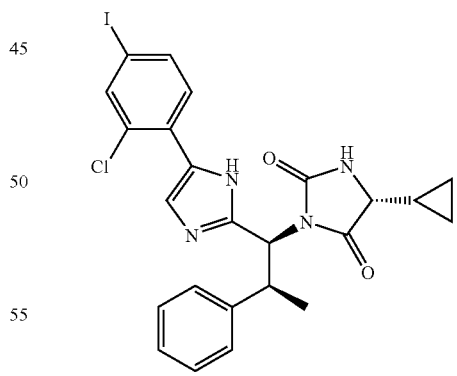

Prepared by the same method as described in example 37 except that in step 86-G (R)-tert-butoxycarbonylamino-cyclopropyl-acetic acid was used in place of (R)-tert-butoxycarbonylamino-[4-((S)-2,2-dimethyl-[1,3]dioxolan-4-ylmethoxy)-phenyl]-acetic acid. HR-MS: calcd for $C_{24}H_{22}ClIN_4O_2$ [M+H$^+$] 561.0549. Found 561.0550.

Example 87

3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione

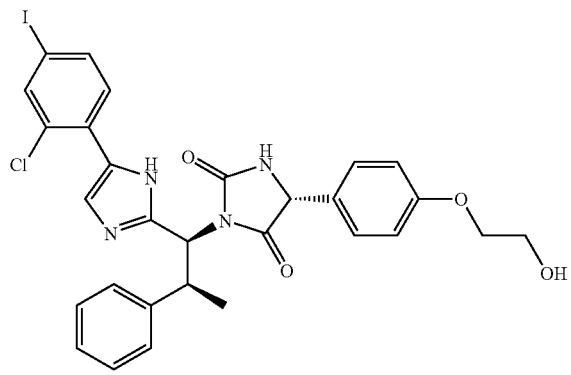

Prepared by the same method as described in example 35 except that the final material from that example ((R)-3-{(1S,2S)-1-[5-(2-chloro-4-iodo-phenyl)-1H-imidazol-2-yl]-2-phenyl-propyl}-5-[4-(2-hydroxy-ethoxy)-phenyl]-imidazolidine-2,4-dione) was dissolved in methanol and refluxed for 12 hours. The solvent was removed in vacuo and the residue was purified by chromatography over silica gel gradient eluted form 40 to 80% v/v ethyl acetate in hexanes to give the compound cited above as a mixture of isomers at the 5-position of the imidazolidine-2,4-dione ring. HR-MS: calcd for $C_{29}H_{26}ClIN_4O_4$ [M+H$^+$] 657.0760. Found 657.0759.

Example 88

(R)-3-{(1S,2S)-1-[5-(2-Chloro-4-iodo-phenyl)-1H-imidazol-2-yl]-2-phenyl-propyl}-5-[4-((S)-2,3-dihydroxy-propoxy)-phenyl]-imidazolidine-2,4-dione

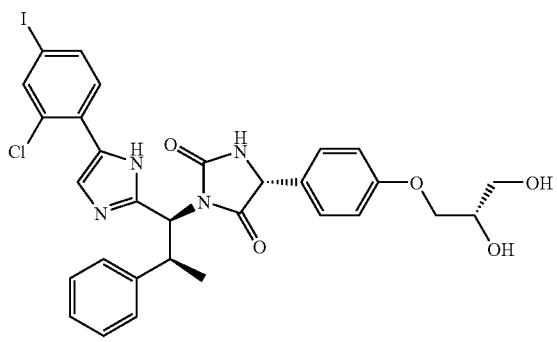

Prepared by the same method as described in example 37 except that in step 88-G (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-((S)-2,2-dimethyl-[1,3]dioxolan-4-ylmethoxy)-phenyl]-acetic acid. (R)-tert-Butoxycarbonylamino-[4-((R)-2,2-dimethyl-[1,3]dioxolan-4-ylmethoxy)-phenyl]-acetic acid was prepared as described in steps 33-T and 33-U except that in step 88-T (R)-2,2-dimethyl-1,3-dioxolane-4-methanol was used in place of (S)-2,2-dimethyl-1,3-dioxolane-4-methanol. HR-MS: calcd for $C_{30}H_{28}ClIN_4O_5$ [M+H$^+$] 687.0866. Found 687.0869.

Example 89

(R)-3-{(1S,2S)-1-[5-(2-Chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione

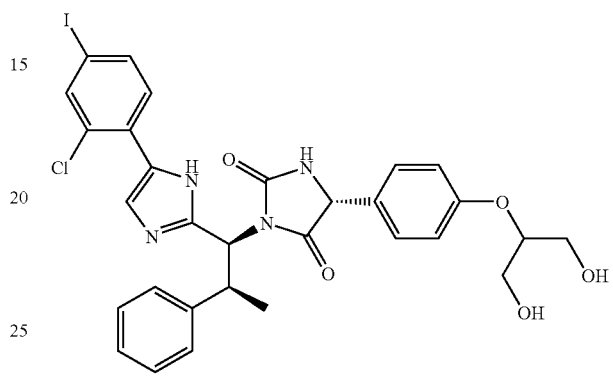

Prepared by the same method as described in example 37 except that in step 89-G (R)-tert-butoxycarbonylamino-[4-(2-hydroxy-1-hydroxymethyl-ethoxy)phenyl]-acetic acid (prepared as described in steps 57-V, 57-W and 57-X) was used in place of (R)-tert-butoxycarbonylamino-[4-((S)-2,2-dimethyl-[1,3]dioxolan-4-ylmethoxy)-phenyl]-acetic acid. HR-MS: calcd for $C_{30}H_{28}ClIN_4O_5$ [M+H$^+$] 687.0866. Found 687.0862.

Example 90

2-[4-((R)-1-{(1S,2S)-1-[5-(2-Chloro-4-iodo-phenyl)-1H-imidazol-2-yl]-2-phenyl-propyl}-2,5-dioxo-imidazolidin-4-yl)-phenoxy]-N,N-dimethyl-acetamide

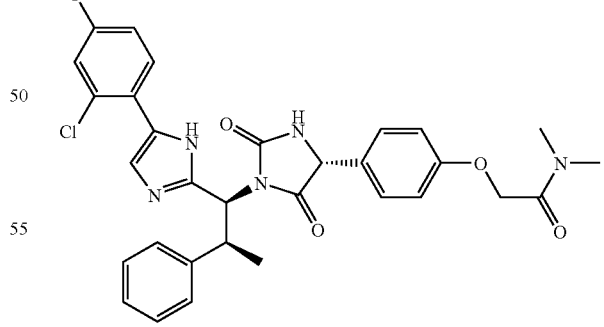

Prepared by the same method as described in example 37 except that in step 90-G (R)-tert-butoxycarbonylamino-(4-dimethylcarbamoylmethoxy-phenyl)-acetic acid (prepared as described in example 6) was used in place of (R)-tert-butoxycarbonylamino-[4-((S)-2,2-dimethyl-[1,3]dioxolan-4-ylmethoxy)-phenyl]-acetic acid. HR-MS: calcd for $C_{31}H_{29}ClIN_5O_4$ [M+H$^+$] 698.1026. Found 698.1024.

Example 91

(R)-3-{(S)-1-[5-(2-Chloro-4-iodo-phenyl)-4-methyl-1H-imidazol-2-yl]-2-methyl-propyl}-5-[4-((R)-2,3-dihydroxy-propoxy)-phenyl]-imidazolidine-2,4-dione

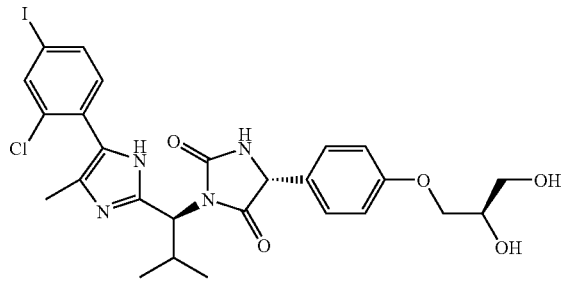

Prepared by the same method as described in example 1 except that (i) in step 91-A 2-chloro-1,4-diiodo-benzene was used in place of 2-fluoro-1,4-diiodo-benzene; (ii) in step 91-B ethylmagnesium bromide was used in place of methylmagnesium chloride; (iii) (S)-2-tert-butoxycarbonylamino-3-methyl-butyric acid was used in place of (2S,3S)-2-tert-butoxycarbonylamino-3-phenyl-butyric acid in step 91-E; (iv) chlorination of the 5-position of the imidazole ring with N-chlorosuccinimide in step 91-F was omitted and (v) (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid in step 91-G. HR-MS: calcd for $C_{26}H_{28}ClIN_4O_5$ [M+H$^+$] 639.0866. Found 639.0860.

Example 92

(R)-3-{(S)-1-[5-(2-Chloro-4-iodo-phenyl)-4-methyl-1H-imidazol-2-yl]-2-phenyl-ethyl}-5-[4-(2-hydroxy-ethoxy)-phenyl]-imidazolidine-2,4-dione

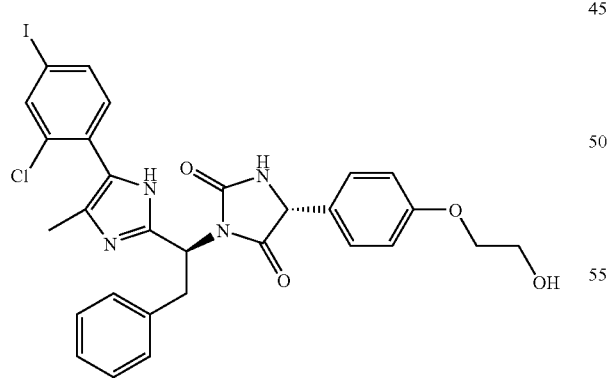

Prepared by the same method as described in example 1 except that (i) in step 92-A 2-chloro-1,4-diiodo-benzene was used in place of 2-fluoro-1,4-diiodo-benzene; (ii) in step 92-B ethylmagnesium bromide was used in place of methylmagnesium chloride; (iii) in step 92-E (S)-2-tert-butoxycarbonylamino-3-phenyl-propionic acid was used in place of (2S,3S)-2-tert-butoxycarbonylamino-3-phenyl-butyric acid and (iv) chlorination of the 5-position of the imidazole ring with N-chlorosuccinimide in step 92-F was omitted. HR-MS: calcd for $C_{29}H_{26}ClIN_4O_4$ [M+H$^+$] 657.0760. Found 657.0766.

Example 93

(R)-3-{(S)-1-[5-(2-Chloro-4-iodo-phenyl)-4-methyl-1H-imidazol-2-yl]-2-phenyl-ethyl}-5-[4-((R)-2,3-dihydroxy-propoxy)-phenyl]-imidazolidine-2,4-dione

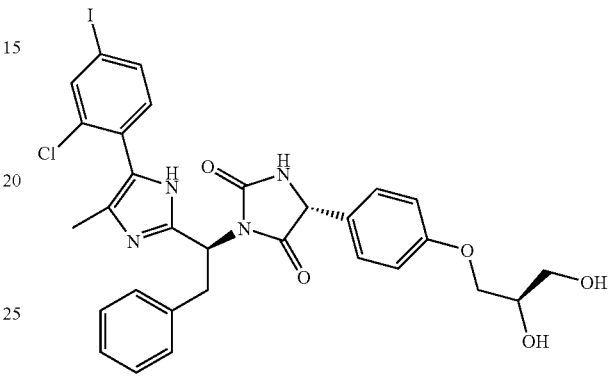

Prepared by the same method as described in example 1 except that (i) in step 93-A 2-chloro-1,4-diiodo-benzene was used in place of 2-fluoro-1,4-diiodo-benzene; (ii) in step 93-B ethylmagnesium bromide was used in place of methylmagnesium chloride; (iii) (S)-2-tert-butoxycarbonylamino-3-phenyl-propionic acid was used in place of (2S,3S)-2-tert-butoxycarbonylamino-3-phenyl-butyric acid in step 93-E; (iv) chlorination of the 5-position of the imidazole ring with N-chlorosuccinimide in step 93-F was omitted and (v) (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid in step 93-G. HR-MS: calcd for $C_{30}H_{28}ClIN_4O_5$ [M+H$^+$] 687.0866. Found 687.0867.

Example 94

(R)-3-{(1S,2S)-1-[5-(2-Chloro-4-iodo-phenyl)-4-methyl-1H-imidazol-2-yl]-2-phenyl-propyl}-5-[4-(2-hydroxy-ethoxy)-phenyl]-imidazolidine-2,4-dione

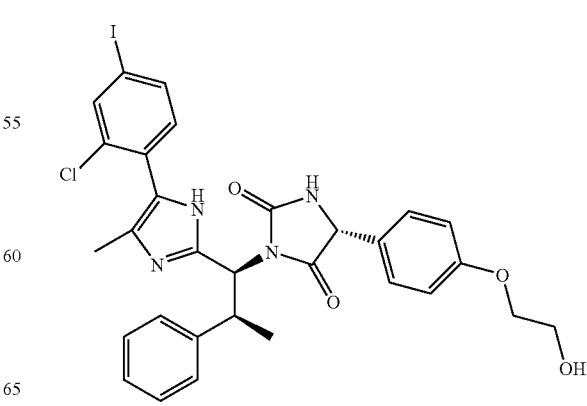

Prepared by the same method as described in example 1 except that (i) in step 94-A 2-chloro-1,4-diiodo-benzene was used in place of 2-fluoro-1,4-diiodo-benzene; (ii) in step 93-B ethylmagnesium bromide was used in place of methylmagnesium chloride and (iii) chlorination of the 5-position of the imidazole ring with N-chlorosuccinimide in step 94-F was omitted. HR-MS: calcd for $C_{30}H_{28}ClIN_4O_4$ [M+H$^+$] 671.0917. Found 671.0917.

Example 95

(R)-3-{(1S,2S)-1-[5-(2-Chloro-4-iodo-phenyl)-4-methyl-1H-imidazol-2-yl]-2-phenyl-propyl}-5-[4-((R)-2,3-dihydroxy-propoxy)-phenyl]-imidazolidine-2,4-dione

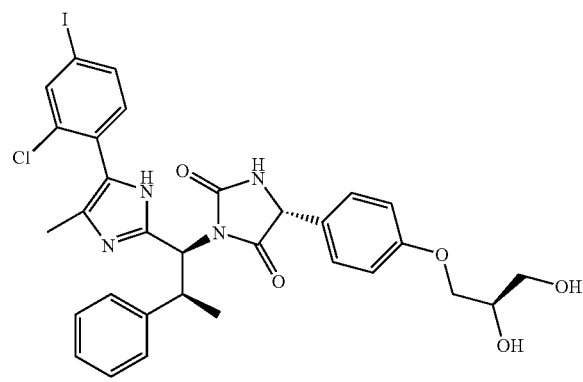

Prepared by the same method as described in example 1 except that (i) in step 95-A 2-chloro-1,4-diiodo-benzene was used in place of 2-fluoro-1,4-diiodo-benzene; (ii) in step 95-B ethylmagnesium bromide was used in place of methylmagnesium chloride; (iii) chlorination of the 5-position of the imidazole ring with N-chlorosuccinimide in step 95-F was omitted, and (iv) (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid in step 95-G. HR-MS: calcd for $C_{31}H_{30}ClIN_4O_5$ [M+H$^+$] 701.1022. Found 701.1017.

Example 96

(R)-3-{(1S,2S)-1-[4-Chloro-5-(2-chloro-4-iodo-phenyl)-1H-imidazol-2-yl]-2-phenyl-propyl}-5-[4-(2-hydroxy-ethoxy)-phenyl]-imidazolidine-2,4-dione

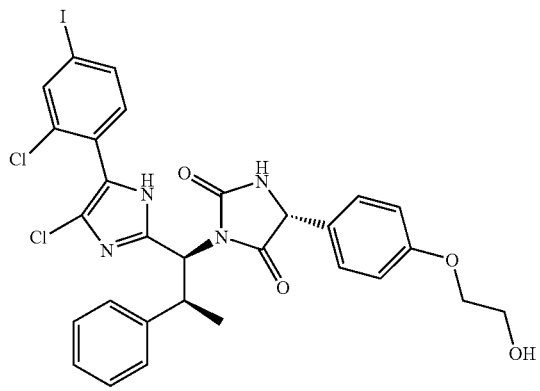

Prepared by the same method as described in example 1 except that in step 96-A 2-chloro-1,4-diiodo-benzene was used in place of 2-fluoro-1,4-diiodo-benzene. HR-MS: calcd for $C_{29}H_{25}Cl_2IN_4O_4$ [M+H$^+$] 691.0371. Found 691.0373.

Example 97

(R)-3-{(1S,2S)-1-[4-Chloro-5-(2-chloro-4-iodo-phenyl)-1H-imidazol-2-yl]-2-phenyl-propyl}-5-[4-((R)-2,3-dihydroxy-propoxy)-phenyl]-imidazolidine-2,4-dione

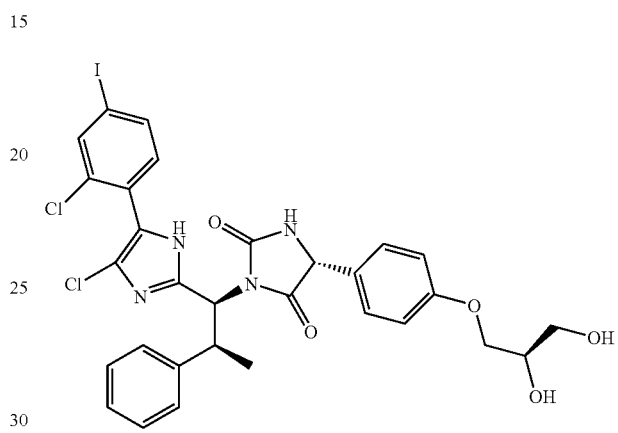

Prepared by the same method as described in example 96 except that in step 97-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{30}H_{27}Cl_2IN_4O_5$ [M+H$^+$] 721.0476. Found 721.0479.

Example 98

(R)-3-{(1S,2S)-1-[4-Chloro-5-(2-chloro-4-iodo-phenyl)-1H-imidazol-2-yl]-2-phenyl-propyl}-5-[4-((S)-2,3-dihydroxy-propoxy)-phenyl]-imidazolidine-2,4-dione

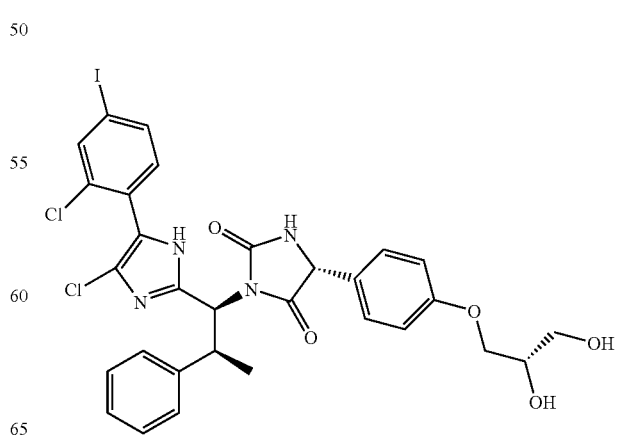

Prepared by the same method as described in example 97 except that in step 98-G (R)-tert-butoxycarbonylamino-[4-((R)-2,2-dimethyl-[1,3]dioxolan-4-ylmethoxy)-phenyl]-acetic acid was used in place of (R)-tert-butoxycarbonylamino-[4-((S)-2,2-dimethyl-[1,3]dioxolan-4-ylmethoxy)-phenyl]-acetic acid. (R)-tert-Butoxycarbonylamino-[4-((R)-2,2-dimethyl-[1,3]dioxolan-4-ylmethoxy)-phenyl]-acetic acid was prepared as described in steps 33-T and 33-U except that in step 98-T (R)-2,2-dimethyl-1,3-dioxolane-4-methanol was used in place of (S)-2,2-dimethyl-1,3-dioxolane-4-methanol. HR-MS: calcd for $C_{30}H_{27}Cl_2IN_4O_5$ [M+H$^+$] 721.0476. Found 721.0480.

Example 99

(R)-3-{(1S,2S)-1-[4-Chloro-5-(2-chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione

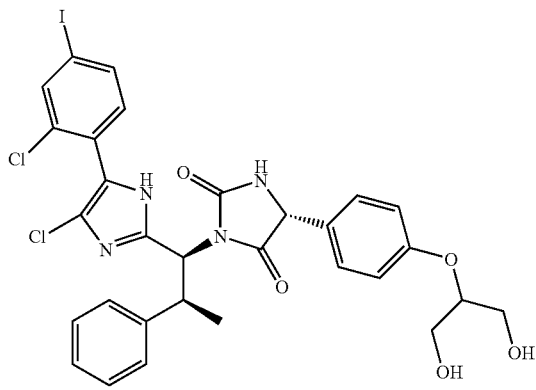

Prepared by the same method as described in example 96 except that in step 99-G (R)-tert-butoxycarbonylamino-[4-(2-hydroxy-1-hydroxymethyl-ethoxy)phenyl]-acetic acid (prepared as described in steps 57-V, 57-W and 57-X) was used in place of (R)-tert-butoxycarbonylamino-[4-(2-tert-butoxy-ethoxy)-phenyl]-acetic acid. HR-MS: calcd for $C_{30}H_{27}Cl_2IN_4O_5$ [M+H$^+$] 721.0476. Found 721.0477.

Example 100

(R)-3-{(1R,2R)-1-[5-(4-Bromo-phenyl)-1H-imidazol-2-yl]-2-methoxy-propyl}-5-[4-(2-hydroxy-ethoxy)-phenyl]-imidazolidine-2,4-dione

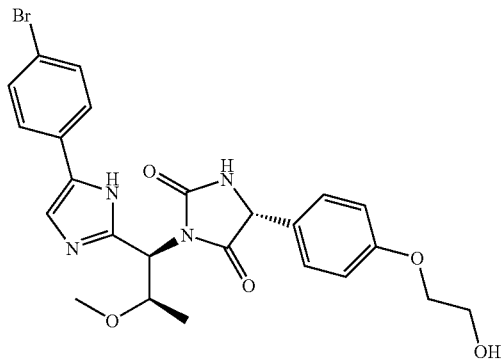

Prepared by the same method as described in example 5 except that commercially available 1-(4-bromo-phenyl)-ethanone was used in place of commercially available 1-(4-iodo-phenyl)-ethanone in step 100-D. HR-MS: calcd for $C_{24}H_{25}BrN_4O_5$ [M+H$^+$] 529.1081. Found 529.1082.

Example 101

(R)-3-{(S)-1-[5-(4-Bromo-phenyl)-1H-imidazol-2-yl]-2-phenyl-ethyl}-5-[4-(2-hydroxy-ethoxy)-phenyl]-imidazolidine-2,4-dione

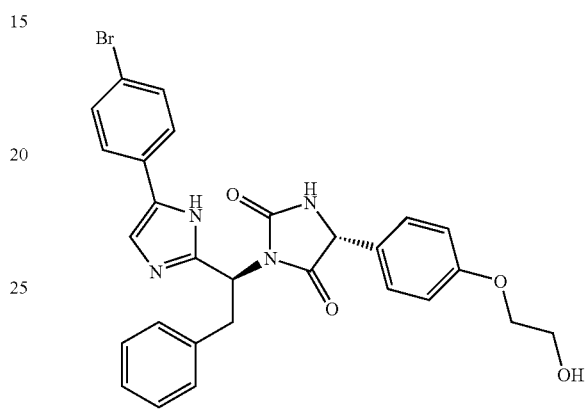

Prepared by the same method as described in example 2 except that commercially available 1-(4-bromo-phenyl)-ethanone was used in place of commercially available 1-(4-iodo-phenyl)-ethanone in step 101-D. HR-MS: calcd for $C_{28}H_{25}BrN_4O_4$ [M+H$^+$] 561.1132. Found 561.1132.

Example 102

(R)-3-{(1S,2S)-1-[5-(4-Bromo-phenyl)-1H-imidazol-2-yl]-2-phenyl-propyl}-5-[4-(2-hydroxy-ethoxy)-phenyl]-imidazolidine-2,4-dione

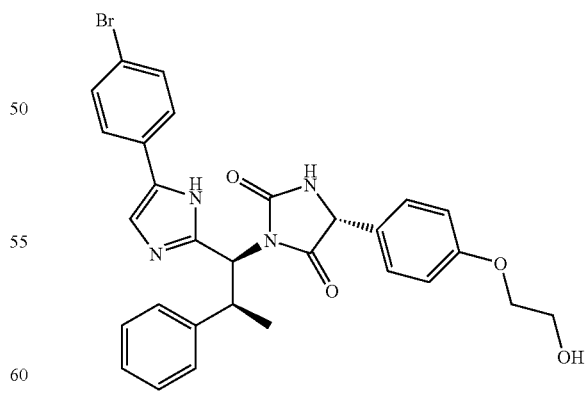

Prepared by the same method as described in example 3 except that commercially available 1-(4-bromo-phenyl)-ethanone was used in place of commercially available 1-(4-iodo-phenyl)-ethanone in step 102-D. HR-MS: calcd for $C_{29}H_{27}BrN_4O_4$ [M+H$^+$] 575.1289. Found 575.1284.

Example 103

(R)-3-{(S)-1-[5-(4-Bromo-phenyl)-4-methyl-1H-imidazol-2-yl]-2-methyl-propyl}-5-[4-(2-hydroxy-ethoxy)-phenyl]-imidazolidine-2,4-dione

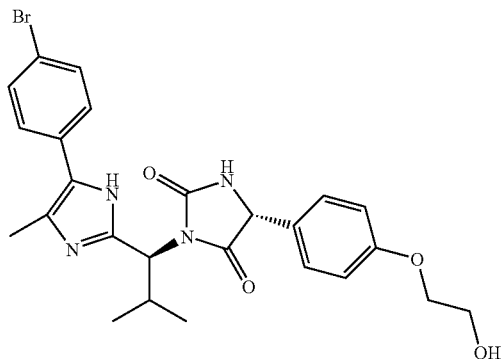

Prepared by the same method as described in example 59 except that commercially available 1-(4-bromo-phenyl)-propanone was used in place of 1-(2-fluoro-4-iodo-phenyl)-propan-1-one in step 103-D. HR-MS: calcd for $C_{25}H_{27}BrN_4O_4$ [M+H$^+$] 527.1289. Found 527.2184.

Example 104

(R)-3-{(S)-1-[5-(4-Bromo-phenyl)-4-methyl-1H-imidazol-2-yl]-3-methyl-butyl}-5-[4-(2-hydroxy-ethoxy)-phenyl]-imidazolidine-2,4-dione

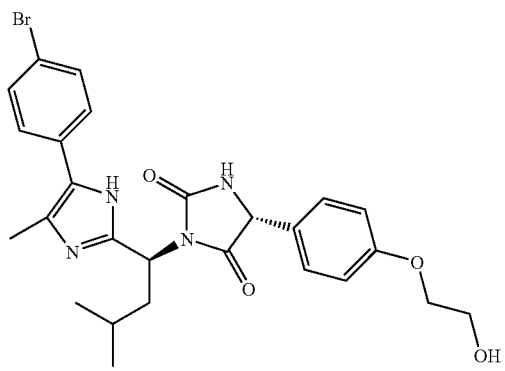

Prepared by the same method as described in example 103 except that (S)-2-tert-butoxycarbonylamino-4-methyl-pentanoic acid was used in place of (2S)-2-tert-butoxycarbonylamino-3-methyl-butyric acid in step 104-E. HR-MS: calcd for $C_{26}H_{29}BrN_4O_4$ [M+H$^+$] 541.1445. Found 541.1445.

Example 105

(R)-3-{(S)-1-[5-(4-Bromo-phenyl)-4-methyl-1H-imidazol-2-yl]-2-phenyl-ethyl}-5-[4-(2-hydroxy-ethoxy)-phenyl]-imidazolidine-2,4-dione

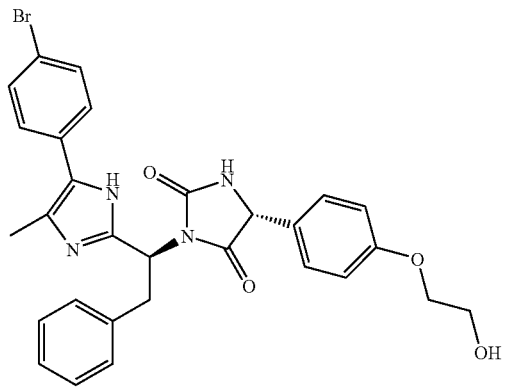

Prepared by the same method as described in example 1 except that (i) steps A, B and C were omitted; (ii) commercially available 1-(4-bromo-phenyl)-propan-1-one was used in place of 1-(2-fluoro-4-iodo-phenyl)-ethanone in step 105-D; (iii) (S)-2-tert-butoxycarbonylamino-3-phenyl-propionic acid was used in place of (2S,3S)-2-tert-butoxycarbonylamino-3-phenyl-butyric acid in step 105-E and (iv) chlorination of the 5-position of the imidazole ring with N-chlorosuccinimide in step 105-F was omitted. HR-MS: calcd for $C_{29}H_{27}BrN_4O_4$ [M+H$^+$] 575.1289. Found 575.1286.

Example 106

(R)-3-{(1S,2S)-1-[5-(4-Bromo-phenyl)-4-methyl-1H-imidazol-2-yl]-2-phenyl-propyl}-5-[4-(2-hydroxy-ethoxy)-phenyl]-imidazolidine-2,4-dione

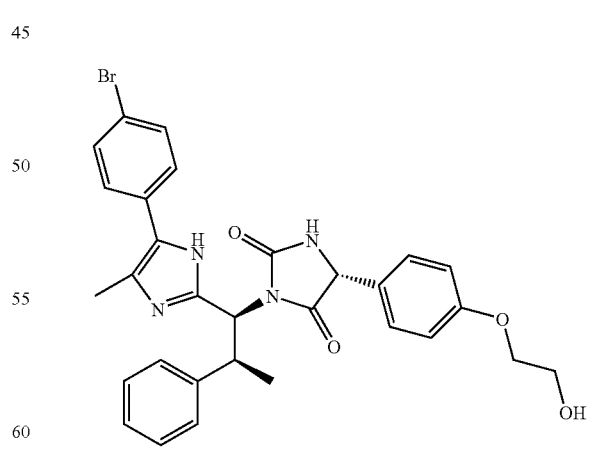

Prepared by the same method as described in example 1 except that (i) steps A, B and C were omitted; (ii) commercially available 1-(4-bromo-phenyl)-propan-1-one was used in place of 1-(2-fluoro-4-iodo-phenyl)-ethanone in step 106-D and (iii) chlorination of the 5-position of the imidazole

Example 107

(R)-3-{(S)-1-[5-(4-Bromo-phenyl)-4-methyl-1H-imidazol-2-yl]-2-thiazol-4-yl-ethyl}-5-[4-(2-hydroxy-ethoxy)-phenyl]-imidazolidine-2,4-dione

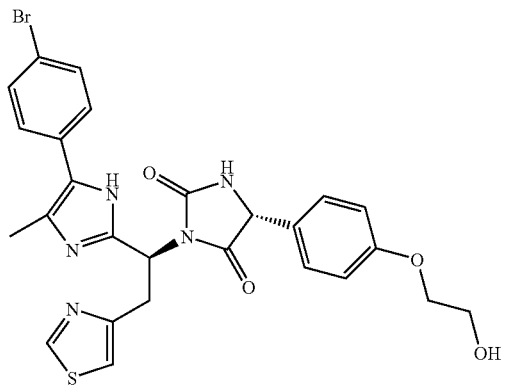

Prepared by the same method as described in example 103 except that (S)-2-tert-butoxycarbonylamino-3-thiazol-4-yl-propionic acid was used in place of (2S)-2-tert-butoxycarbonylamino-3-methyl-butyric acid in step 107-E. HR-MS: calcd for $C_{26}H_{24}BrN_5O_4S$ [M+H$^+$] 582.0805. Found 582.0803.

Example 108

(R)-3-{(S)-1-[5-(4-Bromo-2-fluoro-phenyl)-1H-imidazol-2-yl]-2-phenyl-ethyl}-5-[4-(2-hydroxy-ethoxy)-phenyl]-imidazolidine-2,4-dione

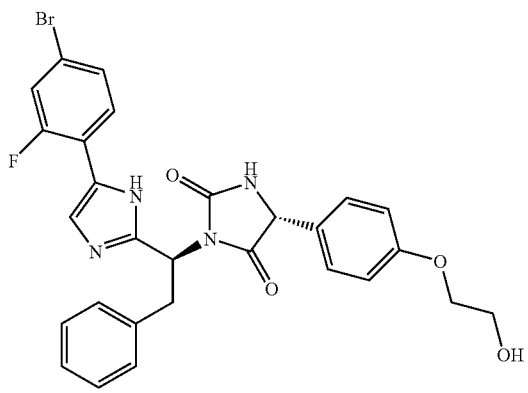

Prepared by the same method as described in example 2 except that commercially available 4-bromo-2-fluoroacetophenone was used in place of 1-(4-iodo-phenyl)-ethanone in step 108-D. HR-MS: calcd for $C_{28}H_{24}BrFN_4O_4$ [M+H$^+$] 579.1038. Found 579.1039.

Example 109

2-[4-((R)-1-{(S)-1-[5-(4-Bromo-2-fluoro-phenyl)-1H-imidazol-2-yl]-2-phenyl-ethyl}-2,5-dioxo-imidazolidin-4-yl)-phenoxy]-N,N-dimethyl-acetamide

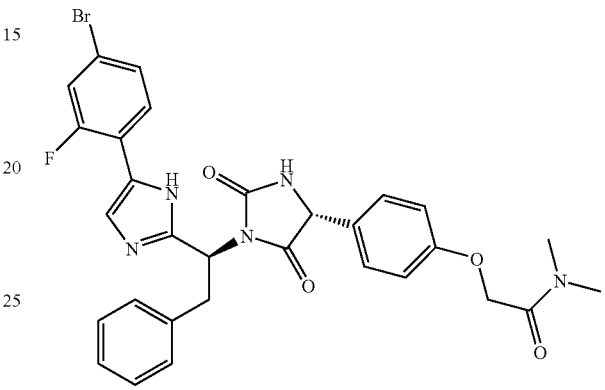

Prepared by the same method as described in example 7 except that (i) commercially available 1-(4-bromo-2-fluoro-phenyl)-ethanone was used in place of 1-(4-chloro-2-fluoro-phenyl)-ethanone in step 109-D and (ii) (S)-2-tert-butoxycarbonylamino-3-phenyl-propionic acid was used in place of (2S,3S)-2-tert-butoxycarbonylamino-3-phenyl-butyric acid in step 109-E. HR-MS: calcd for $C_{30}H_{27}BrFN_5O_4$ [M+H$^+$] 620.1303. Found 620.1302.

Example 110

(R)-3-{(1S,2S)-1-[5-(4-Bromo-2-fluoro-phenyl)-1H-imidazol-2-yl]-2-phenyl-propyl}-5-[4-(2-hydroxy-ethoxy)-phenyl]-imidazolidine-2,4-dione

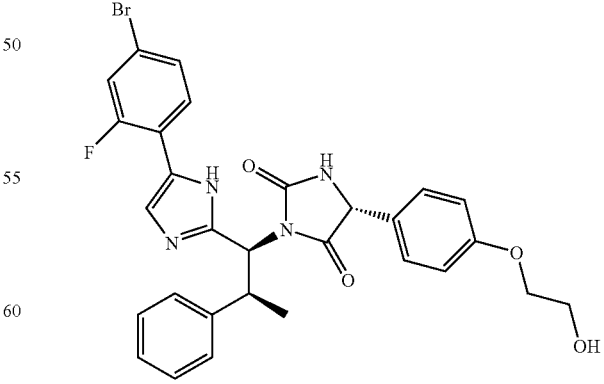

Prepared by the same method as described in example 108 except (2S,3S)-2-tert-butoxycarbonylamino-3-phenyl-butyric acid was used in place of (2S)-2-tert-butoxycarbonylamino-3-phenyl-propionic acid in step 110-E. HR-MS: calcd for $C_{29}H_{26}BrFN_4O_4$ [M+H$^+$] 593.1194. Found 593.1196.

Example 111

2-[4-((R)-1-{(1S,2S)-1-[5-(4-Bromo-2-fluoro-phenyl)-1H-imidazol-2-yl]-2-phenyl-propyl}-2,5-dioxo-imidazolidin-4-yl)-phenoxy]-N,N-dimethyl-acetamide

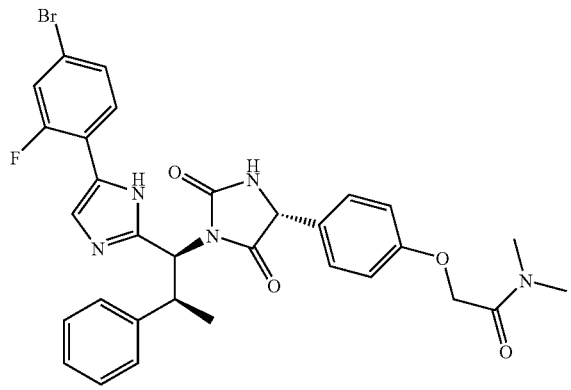

Prepared by the same method as described in example 109 except (2S,3S)-2-tert-butoxycarbonylamino-3-phenyl-butyric acid was used in place of (2S)-2-tert-butoxycarbonylamino-3-phenyl-propionic acid in step 111-E. HR-MS: calcd for $C_{31}H_{29}BrFN_5O_4$ [M+H$^+$] 634.1460. Found 634.1456.

Example 112

(R)-3-{(S)-1-[5-(4-Bromo-2-fluoro-phenyl)-4-methyl-1H-imidazol-2-yl]-2-methyl-propyl}-5-[4-(2-hydroxy-ethoxy)-phenyl]-imidazolidine-2,4-dione

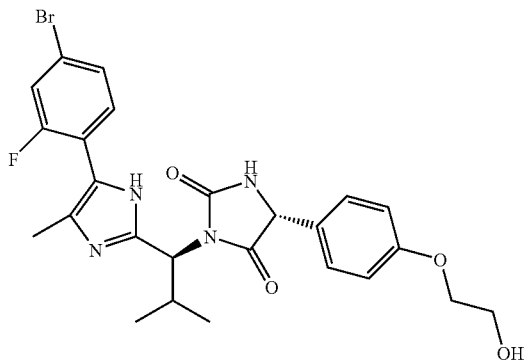

Prepared by the same method as described in example 59 except that 1-(4-bromo-2-fluoro-phenyl)-propan-1-one was used in place of 1-(2-fluoro-4-iodo-phenyl)-ethanone in step 112-D. 1-(4-Bromo-2-fluoro-phenyl)-propan-1-one was prepared as described in steps 6-I and 6-J except that 4-bromo-2-fluoro-benzoic acid was used in place of 4-bromo-2-chlorobenzoic acid in step 112-I. HR-MS: calcd for $C_{25}H_{26}BrFN_4O_4$ [M+H$^+$] 545.1194. Found 545.1191.

Example 113

(R)-3-{(S)-1-[5-(4-Bromo-2-fluoro-phenyl)-4-methyl-1H-imidazol-2-yl]-2-methyl-propyl}-5-[4-((R)-2,3-dihydroxy-propoxy)-phenyl]-imidazolidine-2,4-dione

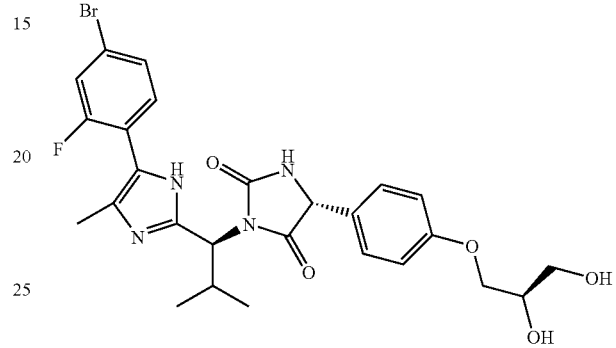

Prepared by the same method as described in example 112 except that in step 113-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{26}H_{28}BrFN_4O_5$ [M+H$^+$] 575.1300. Found 575.1296.

Example 114

(R)-3-{(1R,2R)-1-[5-(4-Bromo-2-fluoro-phenyl)-4-methyl-1H-imidazol-2-yl]-2-methoxy-propyl}-5-[4-(2-hydroxy-ethoxy)-phenyl]-imidazolidine-2,4-dione

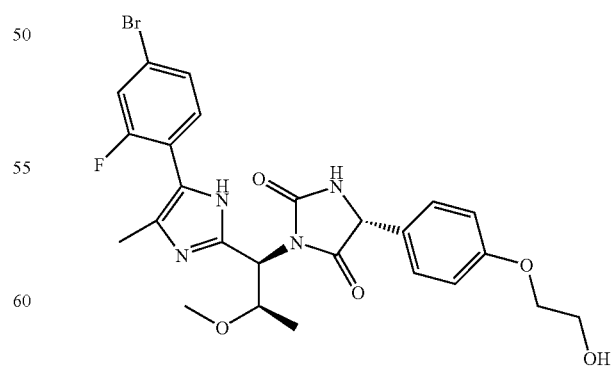

Prepared by the same method as described in example 112 except that in step 114-E (2S,3R)-2-tert-butoxycarbonylamino-3-methoxy-butyric acid was used in place of (S)-2- tert-butoxycarbonylamino-3-methylbutyric acid. HR-MS: calcd for $C_{25}H_{26}BrFN_4O_5$ [M+H$^+$] 561.1144. Found 561.1143.

Example 115

(R)-3-{(1S,2S)-1-[5-(4-Bromo-2-fluoro-phenyl)-4-methyl-1H-imidazol-2-yl]-2-phenyl-propyl}-5-[4-(2-hydroxy-ethoxy)-phenyl]-imidazolidine-2,4-dione

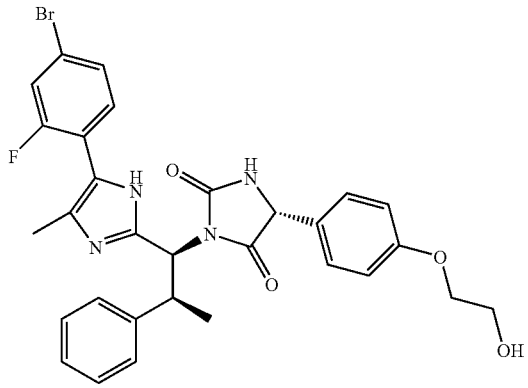

Prepared by the same method as described in example 112 except that in step 115-E (2S,3S)-2-tert-butoxycarbonylamino-3-phenyl-butyric acid was used in place of (S)-2-tert-butoxycarbonylamino-3-methylbutyric acid. HR-MS: calcd for $C_{30}H_{28}BrFN_4O_4$ [M+H$^+$] 607.1351. Found 607.1354.

Example 116

(R)-3-{(1S,2S)-1-[5-(4-Bromo-2-fluoro-phenyl)-4-methyl-1H-imidazol-2-yl]-2-phenyl-propyl}-5-[4-((R)-2,3-dihydroxy-propoxy)-phenyl]-imidazolidine-2,4-dione

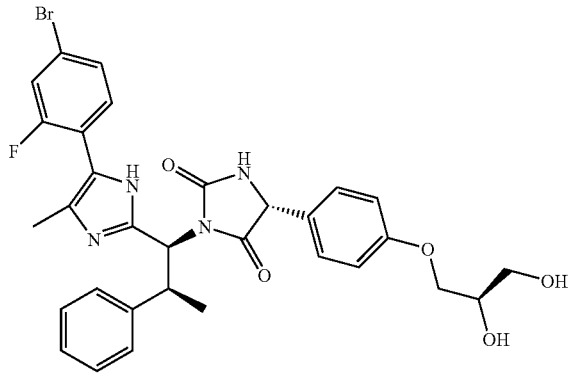

Prepared by the same method as described in example 115 except that in step 116-G (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid. HR-MS: calcd for $C_{31}H_{30}BrFN_4O_5$ [M+H$^+$] 637.1457. Found 637.1455.

Example 117

(R)-3-{(1S,2S)-1-[5-(4-Bromo-2-fluoro-phenyl)-4-methyl-1H-imidazol-2-yl]-2-phenyl-propyl}-5-[4-(2-hydroxy-1-hydroxymethyl-ethoxy)-phenyl]-imidazolidine-2,4-dione

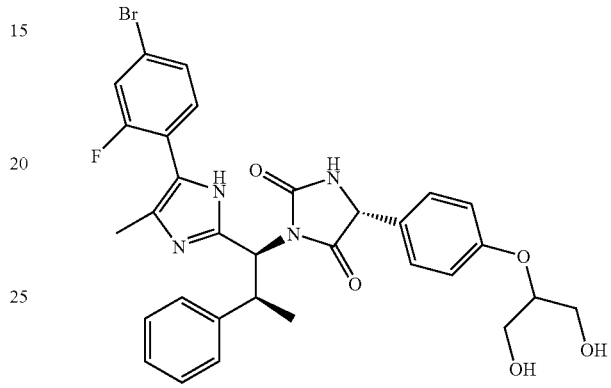

Prepared by the same method as described in example 115 except that in step 117-G (R)-tert-butoxycarbonylamino-[4-(2-hydroxy-1-hydroxymethyl-ethoxy)-phenyl]-acetic acid (prepared as described in steps 57-V, 57-W and 57-X) was used in place of (R)-tert-butoxycarbonylamino-[4-(2-tert-butoxy-ethoxy)-phenyl]-acetic acid. HR-MS: calcd for $C_{31}H_{30}BrFN_4O_5$ [M+H$^+$] 637.1457. Found 637.1455.

Example 118

2-[4-((R)-1-{(S)-1-[5-(4-Bromo-2-fluoro-phenyl)-4-ethyl-1H-imidazol-2-yl]-2-phenyl-ethyl}-2,5-dioxo-imidazolidin-4-yl)-phenoxy]-N,N-dimethyl-acetamide

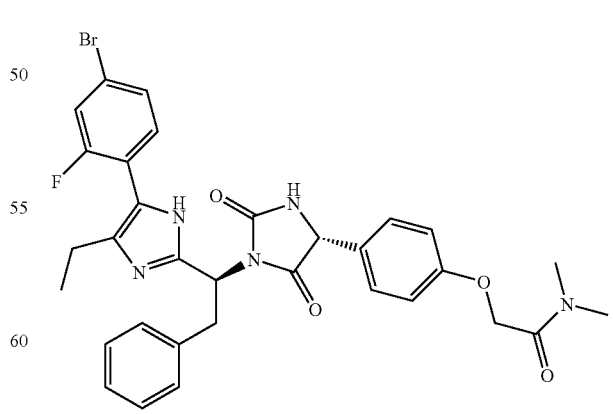

Prepared by the same method as described in example 15 except that in step 118-E (S)-2-tert-butoxycarbonylamino-3-phenyl-propionic acid was used in place of (2S,3S)-2-tertbutoxycarbonylamino-3-phenyl-butyric acid. HR-MS: calcd for $C_{32}H_{31}BrFN_5O_4$ [M+H$^+$] 648.1616. Found 648.1621.

Example 119

(R)-3-{(1S,2S)-1-[5-(4-Bromo-2-fluoro-phenyl)-4-ethyl-1H-imidazol-2-yl]-2-phenyl-propyl}-5-[4-(2-hydroxy-ethoxy)-phenyl]-imidazolidine-2,4-dione

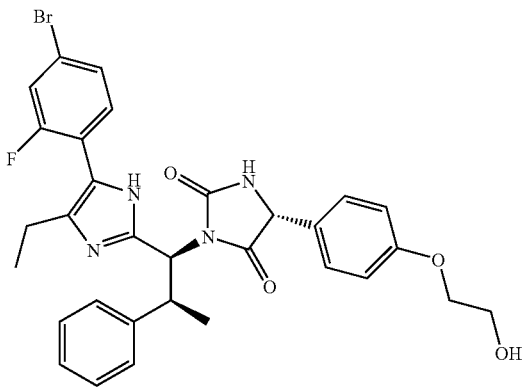

Prepared by the same method as described in example 15 except that in step 119-G (R)-tert-butoxycarbonylamino-[4-(2-tert-butoxy-ethoxy)-phenyl]-acetic acid was used in place of (R)-tert-butoxycarbonylamino-(4-dimethylcarbamoyl-methoxy-phenyl)-acetic acid. HR-MS: calcd for $C_{31}H_{30}BrFN_4O_4$ [M+H$^+$] 621.1507. Found 621.1509.

Example 120

2-[4-((R)-1-{(S)-1-[5-(4-Bromo-2-chloro-phenyl)-1H-imidazol-2-yl]-2-phenyl-ethyl}-2,5-dioxo-imidazolidin-4-yl)-phenoxy]-N,N-dimethyl-acetamide

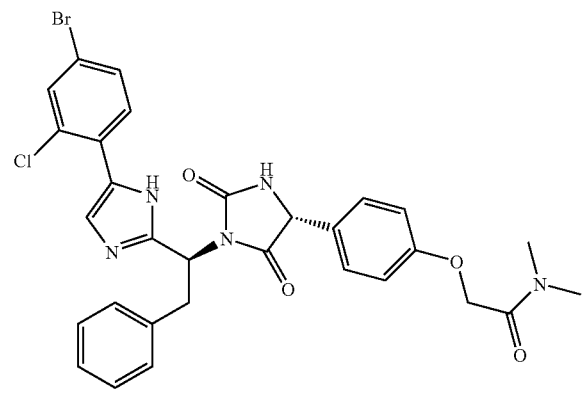

Prepared by the same method as described in example 6 except that in step 120-E (S)-2-tert-butoxycarbonylamino-3-phenyl-propionic acid was used in place of (2S,3S)-2-tert-butoxycarbonylamino-3-phenyl-butyric acid. HR-MS: calcd for $C_{30}H_{27}BrClN_5O_4$ [M+H$^+$] 636.1008. Found 636.1013.

Example 121

(R)-3-{(S)-1-[5-(4-Bromo-2-chloro-phenyl)-1H-imidazol-2-yl]-2-phenyl-ethyl}-5-[4-(2-oxo-2-pyrrolidin-1-yl-ethoxy)-phenyl]-imidazolidine-2,4-dione

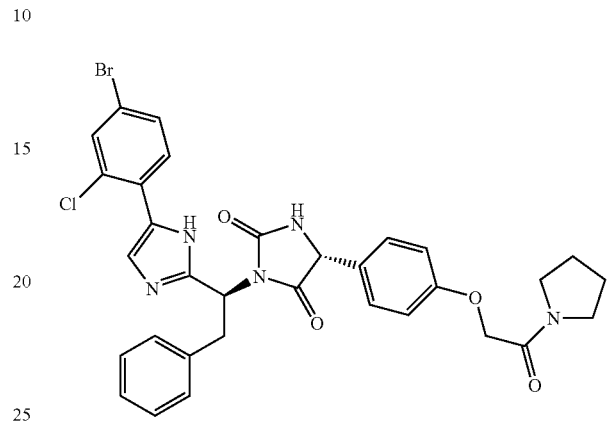

Prepared by the same method as described in example 120 except that in step 121-G (R)-tert-butoxycarbonylamino-[4-(2-oxo-2-pyrrolidin-1-yl-ethoxy)-phenyl]-acetic acid was used in place of (R)-tert-butoxycarbonylamino-(4-dimethylcarbamoylmethoxy-phenyl)-acetic acid. (R)-tert-Butoxycarbonylamino-[4-(2-oxo-2-pyrrolidin-1-yl-ethoxy)-phenyl]-acetic acid was prepared as described in example 6 for the preparation of (R)-tert-butoxycarbonylamino-(4-dimethylcarbamoylmethoxy-phenyl)-acetic acid except that 2-chloro-1-pyrrolidin-1-yl-ethanone was used in place of 2-chloro-N,N-dimethyl-acetamide. HR-MS: calcd for $C_{32}H_{29}BrClN_5O_4$ [M+H$^+$] 662.1164. Found 662.1163.

Example 122

(R)-3-{(1S,2S)-1-[5-(4-Bromo-2-chloro-phenyl)-1H-imidazol-2-yl]-2-phenyl-propyl}-5-[4-(2-hydroxy-ethoxy)-phenyl]-imidazolidine-2,4-dione

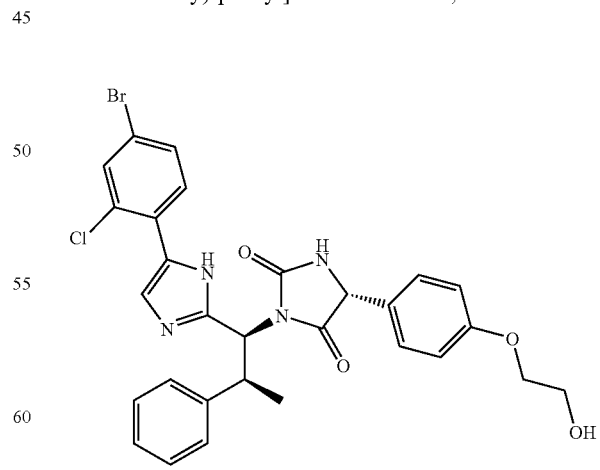

Prepared by the same method as described in example 6 except that in step 122-G (R)-tert-butoxycarbonylamino-[4-(2-tert-butoxy-ethoxy)-phenyl]-acetic acid was used in place of (R)-tert-butoxycarbonylamino-(4-dimethylcarbamoylmethoxy-phenyl)-acetic acid. HR-MS: calcd for $C_{29}H_{26}BrClN_4O_4$ [M+H$^+$] 609.0899. Found 609.0900.

Example 123

(R)-3-{(S)-1-[5-(4-Bromo-2-chloro-phenyl)-1H-imidazol-2-yl]-2-thiazol-4-yl-ethyl}-5-[4-(2-hydroxy-ethoxy)-phenyl]-imidazolidine-2,4-dione

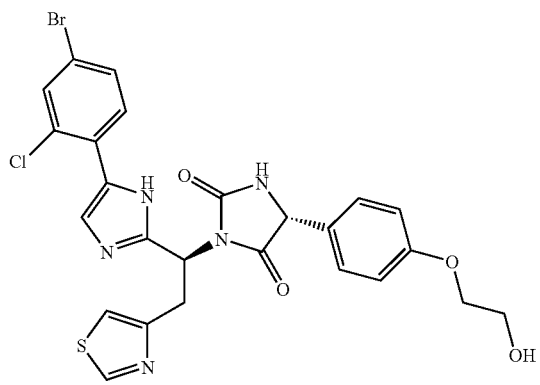

Prepared by the same method as described in example 122 except that (2S)-2-tert-butoxycarbonylamino-3-thiazol-4-yl-propionic acid was used in place of (2S,3S)-2-tert-butoxycarbonylamino-3-phenyl-butyric acid in step 123-E. HR-MS: calcd for $C_{25}H_{21}BrClN_5O_4S$ [M+H$^+$] 602.0259. Found 602.0259.

Example 124

(R)-3-{(1S,2S)-1-[5-(4-Bromo-2-chloro-phenyl)-4-methyl-1H-imidazol-2-yl]-2-phenyl-propyl}-5-[4-(2-hydroxy-ethoxy)-phenyl]-imidazolidine-2,4-dione

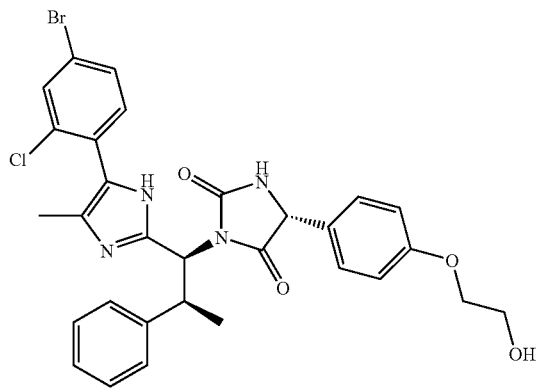

Prepared by the same method as described in example 122 except that in step 124-D 1-(4-bromo-2-chloro-phenyl)-propanone was used in place of 1-(4-bromo-2-chloro-phenyl)-ethanone. 1-(4-Bromo-2-chloro-phenyl)-propanone was prepared as described in steps 6-I and 6-J except that ethyl magnesium bromide was used in place of methyl magnesium bromide in step 124-J. HR-MS: calcd for $C_{30}H_{28}BrClN_4O_4$ [M+H$^+$] 623.1055. Found 623.1057.

Example 125

(R)-3-{(1S,2S)-1-[5-(4-Bromo-2,6-difluoro-phenyl)-1H-imidazol-2-yl]-2-phenyl-propyl}-5-[4-(2-hydroxy-ethoxy)-phenyl]-imidazolidine-2,4-dione

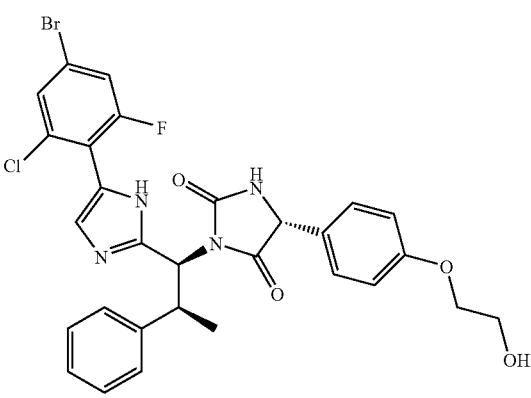

Prepared by the same method as described in example 1 except that (i) steps A, B and C were omitted; (ii) 1-(4-bromo-2,6-difluoro-phenyl)-ethanone (prepared in a similar manner as 1-(2,6-difluoro-4-iodo-phenyl)-ethanone in steps 76-Y and 76-Z except that 1-bromo-3,5-difluoro-benzene was used in place of 1,3-difluoro-5-iodo-benzene in step 76-Y) was used in place of 1-(2-fluoro-4-iodo-phenyl)-ethanone in step 125-D; (iii) chlorination of the 5-position of the imidazole ring with N-chlorosuccinimide in step 125-F was omitted and (iv) following removal of the t-butyl carbamate and t-butyl ether protecting groups cyclization of (R)-2-amino-N-{(1S,2S)-1-[5-(4-bromo-2,6-difluoro-phenyl)-1H-imidazol-2-yl]-2-phenyl-propyl}-2-[4-(2-hydroxy-ethoxy)-phenyl]-acetamide in step 125-H was performed as described in step 34-H. HR-MS: calcd for $C_{29}H_{25}BrF_2N_4O_4$ [M+H$^+$] 611.1100. Found 611.1102.

Example 126

(R)-3-{(1S,2S)-1-[5-(4-Bromo-2,6-difluoro-phenyl)-1H-imidazol-2-yl]-2-phenyl-propyl}-5-[4-((R)-2,3-dihydroxy-propoxy)-phenyl]-imidazolidine-2,4-dione

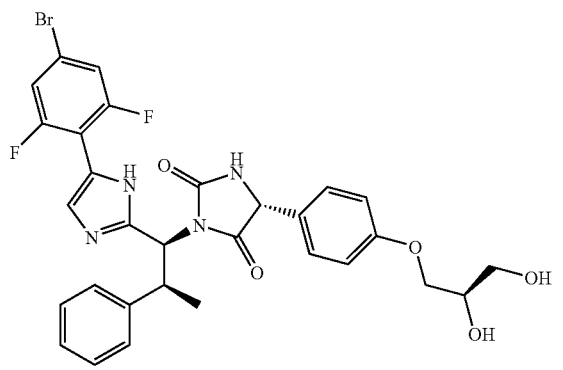

Prepared by the same method as described in example 1 except that (i) steps A, B and C were omitted; (ii) 1-(4-bromo-2,6-difluoro-phenyl)-ethanone (prepared in a similar manner as 1-(2,6-difluoro-4-iodo-phenyl)-ethanone in steps 76-Y and 76-Z except that 1-bromo-3,5-difluoro-benzene was used in place of 1,3-difluoro-5-iodo-benzene in step 76-Y) was used in place of 1-(2-fluoro-4-iodo-phenyl)-ethanone in step 126-D; (iii) chlorination of the 5-position of the imidazole ring with N-chlorosuccinimide in step 126-F was omitted; (iv) (R)-tert-butoxycarbonylamino-[4-((S)-2,2-dimethyl-[1,3]dioxolan-4-ylmethoxy)-phenyl]-acetic acid (prepared as described in steps 33-T and 33-U) was used in place of (R)-tert-butoxycarbonylamino-[4-(2-tert-butoxy-ethoxy)-phenyl]-acetic acid in step 126-G and (v) cyclization of (R)-2-amino-N-{(1S,2S)-1-[5-(4-bromo-2,6-difluoro-phenyl)-1H-imidazol-2-yl]-2-phenyl-propyl}-2-[4-((R)-2,3-dihydroxy-propoxy)-phenyl]-acetamide in step 126-H was performed as described in step 34-H. HR-MS: calcd for $C_{30}H_{27}BrF_2N_4O_5$ [M+H$^+$] 641.1206. Found 641.1204.

Example 127

(R)-3-{(S)-1-[5-(4-Chloro-phenyl)-1H-imidazol-2-yl]-2-phenyl-ethyl}-5-[4-(2-hydroxy-ethoxy)-phenyl]-imidazolidine-2,4-dione

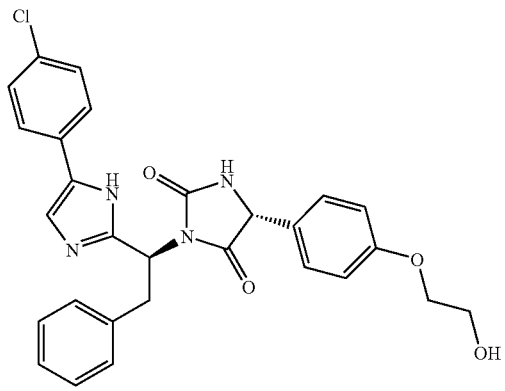

Prepared by the same method as described in example 2 except that in step 127-D 1-(4-chloro-phenyl)-ethanone was used in place of 1-(4-iodo-phenyl)-ethanone. HR-MS: calcd for $C_{28}H_{25}ClN_4O_4$ [M+H$^+$] 517.1637. Found 517.1637.

Example 128

(R)-3-{(1S,2S)-1-[5-(4-Chloro-phenyl)-1H-imidazol-2-yl]-2-phenyl-propyl}-5-[4-(2-hydroxy-ethoxy)-phenyl]-imidazolidine-2,4-dione

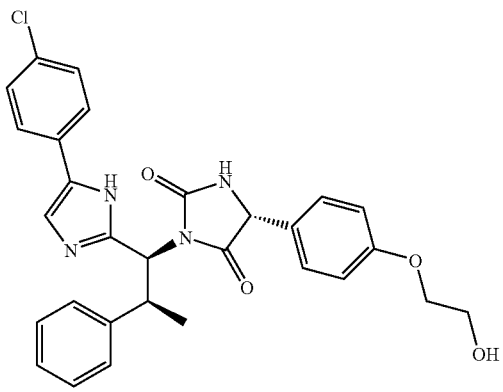

Prepared by the same method as described in example 127 except that in step 128-E (2S,3S)-2-tert-butoxycarbonylamino-3-phenyl-butyric acid was used in place of (S)-2-tert-butoxycarbonylamino-3-phenyl-propionic acid. HR-MS: calcd for $C_{29}H_{27}ClN_4O_4$ [M+H$^+$] 531.1794. Found 531.1791.

Example 129

(R)-3-{(S)-1-[5-(4-Chloro-phenyl)-4-methyl-1H-imidazol-2-yl]-2-phenyl-ethyl}-5-[4-(2-hydroxy-ethoxy)-phenyl]-imidazolidine-2,4-dione

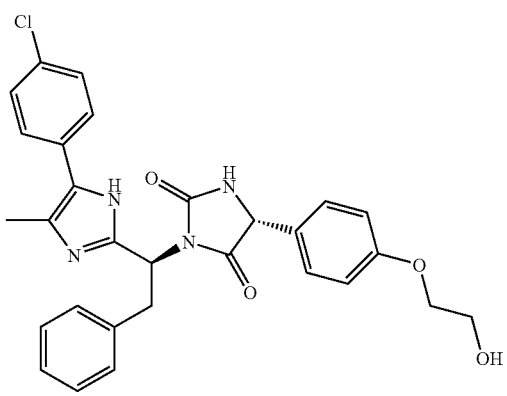

Prepared by the same method as described in example 127 except that in step 129-D commercially available 1-(4-chloro-phenyl)-propanone was used in place of 1-(2-chlorophenyl)-ethanone. HR-MS: calcd for $C_{29}H_{27}ClN_4O_4$ [M+H$^+$] 531.1794. Found 531.1792.

Example 130

(R)-3-{(1S,2S)-1-[5-(4-Chloro-phenyl)-4-methyl-1H-imidazol-2-yl]-2-phenyl-propyl}-5-[4-(2-hydroxy-ethoxy)-phenyl]-imidazolidine-2,4-dione

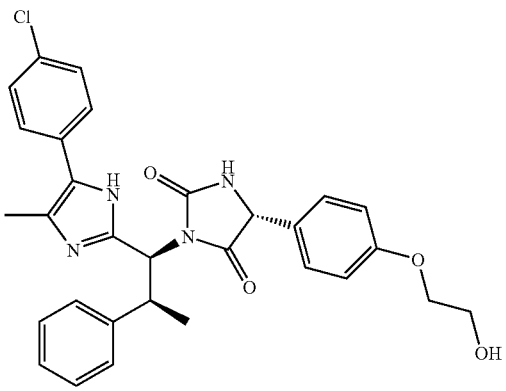

Prepared by the same method as described in example 129 except that in step 130-E (2S,3S)-2-tert-butoxycarbonylamino-3-phenyl-butyric acid was used in place of (S)-2-tert-butoxycarbonylamino-3-phenyl-propionic acid. HR-MS: calcd for $C_{30}H_{29}ClN_4O_4$ [M+H$^+$] 545.1950. Found 545.1952.

Example 131

(R)-3-{(S)-1-[5-(4-Chloro-2-fluoro-phenyl)-1H-imidazol-2-yl]-ethyl}-5-[4-(2-hydroxy-ethoxy)-phenyl]-imidazolidine-2,4-dione

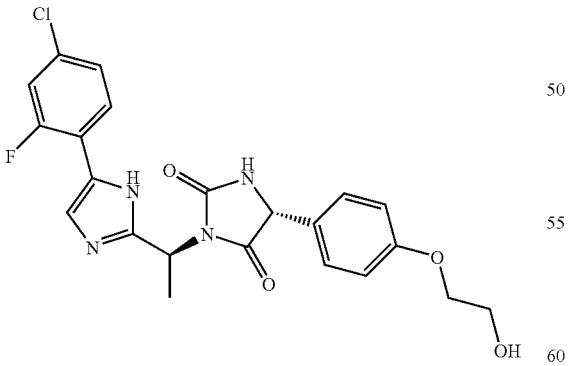

Prepared by the same method as described in example 79 except that (i) steps A, B and C were omitted and (ii) commercially available 1-(4-chloro-2-fluoro-phenyl)-ethanone was used in place of 1-(2-fluoro-4-iodo-phenyl)-ethanone in step 131-D. HR-MS: calcd for $C_{22}H_{20}ClFN_4O_4$ [M+H$^+$] 459.1230. Found 459.1229.

Example 132

(R)-3-{(1S,2S)-1-[5-(4-Chloro-2-fluoro-phenyl)-1H-imidazol-2-yl]-2-phenyl-propyl}-5-[4-(2-hydroxy-ethoxy)-phenyl]-imidazolidine-2,4-dione

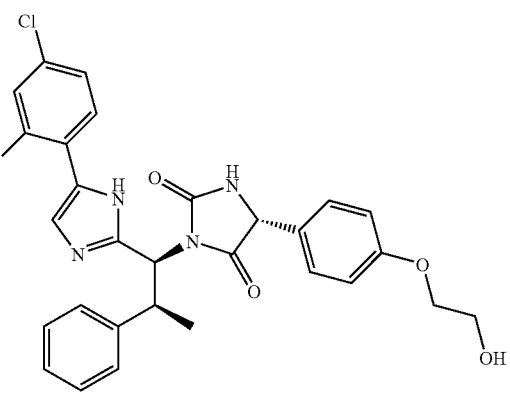

Prepared by the same method as described in example 131 except that (2S,3S)-2-tert-butoxycarbonylamino-3-phenyl-butyric acid was used in place of (2S)-2-tert-butoxycarbonylamino-propionic acid in step 132-E. HR-MS: calcd for $C_{29}H_{26}ClFN_4O_4$ [M+H$^+$] 549.1700. Found 549.1700.

Example 133

(R)-3-{(1S,2S)-1-[5-(2,4-Dichloro-phenyl)-1H-imidazol-2-yl]-2-phenyl-propyl}-5-[4-(2-hydroxy-ethoxy)-phenyl]-imidazolidine-2,4-dione

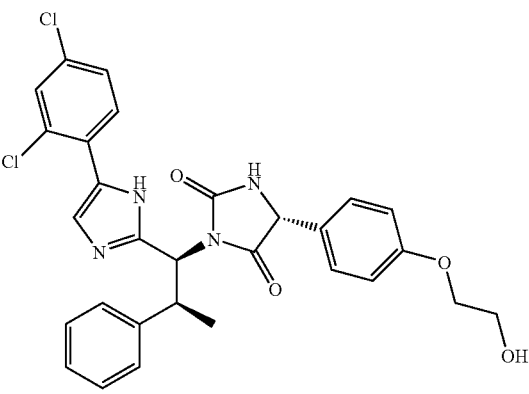

Prepared by the same method as described in example 128 except that in step 133-D 1-(2,4-dichloro-phenyl)-ethanone was used in place of 1-(4-chloro-phenyl)-ethanone. HR-MS: calcd for $C_{29}H_{26}Cl_2N_4O_4$ [M+H$^+$] 565.1404. Found 565.1403.

What is claimed is:

1. Compounds of formula I:

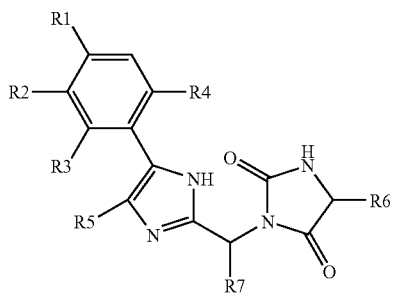

I wherein:

R1 is selected from the group consisting of halogen and lower alkynyl;

R2 is selected from the group consisting of hydrogen and fluorine;

R3 and R4 are independently selected from the group consisting of hydrogen, halogen, and lower alkyl;

R5 is selected from the group consisting of hydrogen, chlorine, and lower alkyl;

R6 is selected from the group consisting of optionally substituted aryl, C3 to C7 cycloalkyl, —(CH$_2$)$_n$—C3 to C7 cycloalkyl, —(CH$_2$)$_n$-lower alkynyl, and —(CH$_2$)$_m$CO—X, wherein X is a member selected from the group consisting of lower alkoxy, hydroxy, and NH—O—(CH$_2$)$_2$—OH, each n is independently 0, 1, or 2 and m is 1 or 2;

R7 is selected from the group consisting of hydrogen and

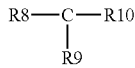

wherein R8 is selected from the group consisting of hydrogen, lower alkyl, C3 to C6 cycloalkyl, lower alkoxy, optionally substituted benzyl, optionally substituted aryl, and optionally substituted heteroaryl;

R9 and R10 are independently selected from the group consisting of hydrogen and lower alkyl; or R9 and R10, together with the carbon to which they are attached, can form a C3 to C7 cycloalkyl group and R8 is hydrogen;

and pharmaceutically acceptable salts or esters thereof.

2. A compound of claim 1 wherein:

R1 is selected from the group consisting of chloro, bromo, iodo, and ethynyl;

R2 is selected from the group consisting of hydrogen and fluorine;

R3 and R4 are independently selected from the group consisting of hydrogen, chlorine, fluorine, and lower alkyl;

R5 is selected from the group consisting of hydrogen, chlorine, and lower alkyl;

R6 is selected from the group consisting of optionally substituted phenyl, cyclopropyl, —(CH2)$_n$-lower cycloalkyl, —(CH2)$_n$-ethynyl, and —(CH2)$_m$CO—X, wherein X is a member selected from the group consisting of methoxy, hydroxy, and NH—O—(CH2)$_2$—OH and each n is independently 0, 1, or 2 and m is 1 or 2;

R7 is

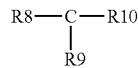

where R8 is selected from the group consisting of hydrogen, lower alkyl, lower alkoxy, benzyl, optionally substituted aryl, and optionally substituted heteroaryl; R9 and R10 are independently selected from the group consisting of hydrogen and lower alkyl; or R9 and R10, together with the carbon to which they are attached, can form a lower cycloalkyl group and R8 is hydrogen;

and pharmaceutically acceptable salts or esters thereof.

3. A compound of claim 2 wherein R5 is selected from the group consisting of hydrogen and chlorine.

4. A compound of claim 3 wherein R8 is optionally substituted aryl.

5. A compound of claim 3 wherein R8 is optionally substituted heteroaryl.

6. A compound of claim 3 wherein R8 is selected from the group consisting of lower alkyl and lower alkoxy.

7. A compound of claim 2 wherein R2 is hydrogen, R3 and R4 are independently selected from the group consisting of hydrogen, fluorine, chlorine, and methyl, R5 is selected from the group consisting of hydrogen and chlorine, R6 is optionally substituted phenyl, R7 is

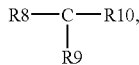

R8 is selected from the group consisting of lower alkyl, lower alkoxy and optionally substituted aryl, R9 is hydrogen, and R10 is selected from the group consisting of hydrogen and methyl.

8. A compound of claim 7 wherein R1 is selected from the group consisting of chloro, bromo and iodo and R8 is optionally substituted phenyl.

9. A compound of claim 7 wherein R1 is selected from the group consisting of chloro, bromo and iodo, R6 is phenyl substituted by an alkoxy group, and R8 is selected from the group consisting of unsubstituted phenyl and phenyl substituted by a member selected from the group consisting of cyano, trifluoromethyl, methoxy, fluoro, chloro, bromo, and iodo.

10. A compound of claim 7 wherein R1 is selected from chloro, bromo and iodo, R6 is phenyl substituted by an alkoxy group, and R8 is selected from lower alkyl and lower alkoxy.

11. A compound of claim 10 wherein R6 is phenyl substituted by a member selected from the group consisting of 2-hydroxyethoxy and 2,3-dihydroxypropoxy.

12. A compound of claim 7 wherein R5 is chlorine.

13. A compound of claim 8 wherein R5 is chlorine.

14. A compound of claim 9 wherein R5 is chlorine.

15. A compound of claim 10 wherein R5 is chlorine.

16. A compound of claim 11 wherein R5 is chlorine.

17. A compound of claim 1 selected from the group consisting of:

(R)-5-[4-(2-Hydroxy-ethoxy)-phenyl]-3-{(S)-1-[5-(4-iodo-phenyl)-1H-imidazol-2-yl]-2-phenyl-ethyl}-imidazolidine-2,4-dione;

(R)-5-[4-(2-Hydroxy-ethoxy)-phenyl]-3-{(1S,2S)-1-[5-(4-iodo-phenyl)-1H-imidazol-2-yl]-2-phenyl-propyl}-imidazolidine-2,4-dione;

(R)-5-[4-(2-Hydroxy-ethoxy)-phenyl]-3-{(S)-1-[5-(4-iodo-phenyl)-1H-imidazol-2-yl]-2-methyl-propyl}-imidazolidine-2,4-dione;

(R)-5-[4-(2-Hydroxy-ethoxy)-phenyl]-3-{(1R,2R)-1-[5-(4-iodo-phenyl)-1H-imidazol-2-yl]-2-methoxy-propyl}-imidazolidine-2,4-dione;

2-[4-((R)-1-{(1S,2S)-1-[5-(4-Bromo-2-chloro-phenyl)-1H-imidazol-2-yl]-2-phenyl-propyl}-2,5-dioxo-imidazolidin-4-yl)-phenoxy]-N,N-dimethyl-acetamide;

2-[4-((R)-1-{(1S,2S)-1-[5-(4-Chloro-2-fluoro-phenyl)-1H-imidazol-2-yl]-2-phenyl-propyl}-2,5-dioxo-imidazolidin-4-yl)-phenoxy]-N,N-dimethyl-acetamide;

((R)-1-{(1S,2S)-1-[5-(4-Iodo-phenyl)-1H-imidazol-2-yl]-2-phenyl-propyl}-2,5-dioxo-imidazolidin-4-yl)-acetic acid; hydrogen chloride salt;

N-(2-Hydroxy-ethoxy)-2-((R)-1-{(1S,2S)-1-[5-(4-iodo-phenyl)-1H-imidazol-2-yl]-2-phenyl-propyl}-2,5-dioxo-imidazolidin-4-yl)-acetamide;

3-((R)-1-{(S)-1-[5-(4-Iodo-phenyl)-1H-imidazol-2-yl]-2-methyl-propyl}-2,5-dioxo-imidazolidin-4-yl)-propionic acid; hydrogen chloride salt;

N-(2-Hydroxy-ethoxy)-3-((R)-1-{(S)-1-[5-(4-iodo-phenyl)-1H-imidazol-2-yl]-2-methyl-propyl}-2,5-dioxo-imidazolidin-4-yl)-propionamide;

3-((R)-1-{(S)-1-[5-(4-Iodo-phenyl)-1H-imidazol-2-yl]-2-methyl-propyl}-2,5-dioxo-imidazolidin-4-yl)-propionic acid methyl ester;

(R)-3-{(1S,2S)-1-[5-(4-Bromo-2-methyl-phenyl)-1H-imidazol-2-yl]-2-phenyl-propyl}-5-[4-(2-hydroxy-ethoxy)-phenyl]-imidazolidine-2,4-dione;

(R)-5-[4-(2-Hydroxy-ethoxy)-phenyl]-3-[(S)-1-[5-(4-iodo-phenyl)-1H-imidazol-2-yl]-2-(2-trifluoromethyl-phenyl)-ethyl]-imidazolidine-2,4-dione;

(R)-3-{(1S,2S)-1-[5-(2-Fluoro-phenyl)-1H-imidazol-2-yl]-2-phenyl-propyl}-5-[4-(2-hydroxy-ethoxy)-phenyl]-imidazolidine-2,4-dione;

(R)-3-{(S)-1-[5-(4-Iodo-phenyl)-1H-imidazol-2-yl]-2-phenyl-ethyl}-5-prop-2-ynyl-imidazolidine-2,4-dione;

(R)-3-{(1S,2S)-1-[5-(4-Bromo-2-chloro-phenyl)-1H-imidazol-2-yl]-2-phenyl-propyl}-5-cyclopropyl-imidazolidine-2,4-dione;

(R)-3-{(S)-1-[5-(4-Bromo-3-fluoro-phenyl)-1H-imidazol-2-yl]-2-phenyl-ethyl}-5-[4-(2-hydroxy-ethoxy)-phenyl]-imidazolidine-2,4-dione;

(R)-3-{(1S,2S)-1-[5-(2-Fluoro-4-iodo-phenyl)-1H-imidazol-2-yl]-2-methyl-butyl}-5-[4-(2-hydroxy-ethoxy)-phenyl]-imidazolidine-2,4-dione;

(R)-3-{(S)-1-[5-(2-Fluoro-4-iodo-phenyl)-1H-imidazol-2-yl]-2-thiazol-4-yl-ethyl}-5-[4-(2-hydroxy-ethoxy)-phenyl]-imidazolidine-2,4-dione;

(R)-3-{(S)-Cyclopropyl-[5-(2-fluoro-4-iodo-phenyl)-1H-imidazol-2-yl]-methyl}-5-[4-(2-hydroxy-ethoxy)-phenyl]-imidazolidine-2,4-dione;

(R)-3-[(S)-1-[5-(2-Fluoro-4-iodo-phenyl)-1H-imidazol-2-yl]-2-(2-fluoro-phenyl)-ethyl]-5-[4-(2-hydroxy-ethoxy)-phenyl]-imidazolidine-2,4-dione;

(R)-3-{(S)-1-[5-(2-Fluoro-4-iodo-phenyl)-1H-imidazol-2-yl]-3-phenyl-propyl}-5-[4-(2-hydroxy-ethoxy)-phenyl]-imidazolidine-2,4-dione;

(R)-3-{(S)-2-(2-Chloro-phenyl)-1-[5-(2-fluoro-4-iodo-phenyl)-1H-imidazol-2-yl]-ethyl}-5-[4-(2-hydroxy-ethoxy)-phenyl]-imidazolidine-2,4-dione;

(R)-5-[4-(2-Hydroxy-ethoxy)-phenyl]-3-[(S)-1-[5-(4-iodo-phenyl)-1H-imidazol-2-yl]-2-(4-methoxy-phenyl)-ethyl]-imidazolidine-2,4-dione;

(R)-3-{(1R,2R)-1-[5-(2-Fluoro-4-iodo-phenyl)-1H-imidazol-2-yl]-2-methoxy-propyl}-5-[4-(2-hydroxy-ethoxy)-phenyl]-imidazolidine-2,4-dione;

(R)-3-{(1S,2S)-1-[5-(4-Ethynyl-2-fluoro-phenyl)-1H-imidazol-2-yl]-2-phenyl-propyl}-5-[4-(2-hydroxy-ethoxy)-phenyl]-imidazolidine-2,4-dione;

(R)-3-[(S)-1-[5-(2-Fluoro-4-iodo-phenyl)-1H-imidazol-2-yl]-2-(4-fluoro-phenyl)-ethyl]-5-[4-(2-hydroxy-ethoxy)-phenyl]-imidazolidine-2,4-dione;

4-((S)-2-[5-(2-Fluoro-4-iodo-phenyl)-1H-imidazol-2-yl]-2-{(R)-4-[4-(2-hydroxy-ethoxy)-phenyl]-2,5-dioxo-imidazolidin-1-yl}-ethyl)-benzonitrile;

(R)-5-[4-((R)-2,3-Dihydroxy-propoxy)-phenyl]-3-{(S)-1-[5-(2-fluoro-4-iodo-phenyl)-1H-imidazol-2-yl]-2-methyl-propyl}-imidazolidine-2,4-dione;

(R)-3-{(1S,2S)-1-[5-(2-Chloro-4-iodo-phenyl)-1H-imidazol-2-yl]-2-phenyl-propyl}-5-[4-(2-hydroxy-ethoxy)-phenyl]-imidazolidine-2,4-dione;

(R)-5-[4-((R)-2,3-Dihydroxy-propoxy)-phenyl]-3-{(1S,2S)-1-[5-(2-fluoro-4-iodo-phenyl)-1H-imidazol-2-yl]-2-phenyl-propyl}-imidazolidine-2,4-dione;

(R)-3-{(1S,2S)-1-[5-(2-Chloro-4-iodo-phenyl)-1H-imidazol-2-yl]-2-phenyl-propyl}-5-[4-((R)-2,3-dihydroxy-propoxy)-phenyl]-imidazolidine-2,4-dione;
3-((R)-1-{(S)-1-[5-(4-Iodo-phenyl)-1H-imidazol-2-yl]-2-methyl-propyl}-2,5-dioxo-imidazolidin-4-yl)-propionic acid tert-butyl ester;
3-((R)-1-{(S)-1-[5-(4-Iodo-phenyl)-1H-imidazol-2-yl]-2-methyl-propyl}-2,5-dioxo-imidazolidin-4-yl)-N-(2-vinyloxy-ethoxy)-propionamide;
(R)-5-[4-(2-Hydroxy-ethoxy)-phenyl]-3-{(S)-1-[5-(4-iodo-phenyl)-1H-imidazol-2-yl]-1-methyl-2-phenyl-ethyl}-imidazolidine-2,4-dione;
(R)-3-{(S)-2-(4-Fluoro-phenyl)-1-[5-(4-iodo-phenyl)-1H-imidazol-2-yl]-ethyl}-5-[4-(2-hydroxy-ethoxy)-phenyl]-imidazolidine-2,4-dione;
2-((R)-1-{(1S,2S)-1-[5-(4-Iodo-phenyl)-1H-imidazol-2-yl]-2-phenyl-propyl}-2,5-dioxo-imidazolidin-4-yl)-N-(2-vinyloxy-ethoxy)-acetamide;
(R)-3-[5-(2-Fluoro-4-iodo-phenyl)-1H-imidazol-2-ylmethyl]-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-ethyl}-5-[4-(2-hydroxy-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-ethyl}-imidazolidine-2,4-dione;
(R)-3-{(S)-1-[5-(2-Fluoro-4-iodo-phenyl)-1H-imidazol-2-yl]-2-methyl-propyl}-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-3-methyl-butyl}-5-[4-(2-hydroxy-ethoxy)-phenyl]-imidazolidine-2,4-dione;
(R)-3-{(S)-2-Cyclohexyl-1-[5-(2-fluoro-4-iodo-phenyl)-1H-imidazol-2-yl]-ethyl}-5-[4-(2-hydroxy-ethoxy)-phenyl]-imidazolidine-2,4-dione;
(R)-3-{1-[5-(2-Fluoro-4-iodo-phenyl)-1H-imidazol-2-yl]-cyclopropyl}-5-[4-(2-hydroxy-ethoxy)-phenyl]-imidazolidine-2,4-dione;
5-[4-((R)-2,3-Dihydroxy-propoxy)-phenyl]-3-{(1R,2R)-1-[5-(2-fluoro-4-iodo-phenyl)-1H-imidazol-2-yl]-2-methoxy-propyl}-imidazolidine-2,4-dione;
(R)-3-{(S)-1-[5-(2-Fluoro-4-iodo-phenyl)-1H-imidazol-2-yl]-2-phenyl-ethyl}-5-[4-(2-hydroxy-ethoxy)-phenyl]-imidazolidine-2,4-dione;
(R)-3-{(S)-1-[5-(2-Fluoro-4-iodo-phenyl)-1H-imidazol-2-yl]-2-phenyl-ethyl}-5-[4-(2-methoxy-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-2-phenyl-ethyl}-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-methoxy-ethoxy)-phenyl]-imidazolidine-2,4-dione;
(R)-3-{(1S,2S)-1-[5-(2-Fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
(R)-5-[4-((R)-2,3-Dihydroxy-propoxy)-phenyl]-3-{(S)-1-[5-(2-fluoro-4-iodo-phenyl)-1H-imidazol-2-yl]-2-thiazol-4-yl-ethyl}-imidazolidine-2,4-dione;
(R)-3-{(1S,2S)-1-[5-(2,6-Difluoro-4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2,6-Difluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
(R)-3-[5-(2-Chloro-4-iodo-phenyl)-1H-imidazol-2-ylmethyl]-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-ethyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-butyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-pentyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-3-methyl-butyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-2-phenyl-ethyl}-5-[4-(2-hydroxy-ethoxy)-phenyl]-imidazolidine-2,4-dione;
(R)-3-{(S)-1-[5-(2-Chloro-4-iodo-phenyl)-1H-imidazol-2-yl]-2-phenyl-ethyl}-5-[4-((R)-2,3-dihydroxy-propoxy)-phenyl]-imidazolidine-2,4-dione;
2-[4-((R)-1-{(S)-1-[5-(2-Chloro-4-iodo-phenyl)-1H-imidazol-2-yl]-2-phenyl-ethyl}-2,5-dioxo-imidazolidin-4-yl)-phenoxy]-N,N-dimethyl-acetamide;
(R)-3-{(1S,2S)-1-[5-(2-Chloro-4-iodo-phenyl)-1H-imidazol-2-yl]-2-phenyl-propyl}-5-cyclopropyl-imidazolidine-2,4-dione;
3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione;
(R)-3-{(1S,2S)-1-[5-(2-Chloro-4-iodo-phenyl)-1H-imidazol-2-yl]-2-phenyl-propyl}-5-[4-((S)-2,3-dihydroxy-propoxy)-phenyl]-imidazolidine-2,4-dione;
(R)-3-{(1S,2S)-1-[5-(2-Chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;
2-[4-((R)-1-{(1S,2S)-1-[5-(2-Chloro-4-iodo-phenyl)-1H-imidazol-2-yl]-2-phenyl-propyl}-2,5-dioxo-imidazolidin-4-yl)-phenoxy]-N,N-dimethyl-acetamide;
(R)-3-{(1R,2R)-1-[5-(4-Bromo-phenyl)-1H-imidazol-2-yl]-2-methoxy-propyl}-5-[4-(2-hydroxy-ethoxy)-phenyl]-imidazolidine-2,4-dione;
(R)-3-{(S)-1-[5-(4-Bromo-phenyl)-1H-imidazol-2-yl]-2-phenyl-ethyl}-5-[4-(2-hydroxy-ethoxy)-phenyl]-imidazolidine-2,4-dione;
(R)-3-{(1S,2S)-1-[5-(4-Bromo-phenyl)-1H-imidazol-2-yl]-2-phenyl-propyl}-5-[4-(2-hydroxy-ethoxy)-phenyl]-imidazolidine-2,4-dione;
(R)-3-{(S)-1-[5-(4-Bromo-2-fluoro-phenyl)-1H-imidazol-2-yl]-2-phenyl-ethyl}-5-[4-(2-hydroxy-ethoxy)-phenyl]-imidazolidine-2,4-dione;
2-[4-((R)-1-{(S)-1-[5-(4-Bromo-2-fluoro-phenyl)-1H-imidazol-2-yl]-2-phenyl-ethyl}-2,5-dioxo-imidazolidin-4-yl)-phenoxy]-N,N-dimethyl-acetamide;
(R)-3-{(1S,2S)-1-[5-(4-Bromo-2-fluoro-phenyl)-1H-imidazol-2-yl]-2-phenyl-propyl}-5-[4-(2-hydroxy-ethoxy)-phenyl]-imidazolidine-2,4-dione;
2-[4-((R)-1-{(1S,2S)-1-[5-(4-Bromo-2-fluoro-phenyl)-1H-imidazol-2-yl]-2-phenyl-propyl}-2,5-dioxo-imidazolidin-4-yl)-phenoxy]-N,N-dimethyl-acetamide;

2-[4-((R)-1-{(S)-1-[5-(4-Bromo-2-chloro-phenyl)-1H-imidazol-2-yl]-2-phenyl-ethyl}-2,5-dioxo-imidazolidin-4-yl)-phenoxy]-N,N-dimethyl-acetamide;

(R)-3-{(S)-1-[5-(4-Bromo-2-chloro-phenyl)-1H-imidazol-2-yl]-2-phenyl-ethyl}-5-[4-(2-oxo-2-pyrrolidin-1-yl-ethoxy)-phenyl]-imidazolidine-2,4-dione;

(R)-3-{(1S,2S)-1-[5-(4-Bromo-2-chloro-phenyl)-1H-imidazol-2-yl]-2-phenyl-propyl}-5-[4-(2-hydroxy-ethoxy)-phenyl]-imidazolidine-2,4-dione;

(R)-3-{(S)-1-[5-(4-Bromo-2-chloro-phenyl)-1H-imidazol-2-yl]-2-thiazol-4-yl-ethyl}-5-[4-(2-hydroxy-ethoxy)-phenyl]-imidazolidine-2,4-dione;

(R)-3-{(1S,2S)-1-[5-(4-Bromo-2,6-difluoro-phenyl)-1H-imidazol-2-yl]-2-phenyl-propyl}-5-[4-(2-hydroxy-ethoxy)-phenyl]-imidazolidine-2,4-dione;

(R)-3-{(1S,2S)-1-[5-(4-Bromo-2,6-difluoro-phenyl)-1H-imidazol-2-yl]-2-phenyl-propyl}-5-[4-((R)-2,3-dihydroxy-propoxy)-phenyl]-imidazolidine-2,4-dione;

(R)-3-{(S)-1-[5-(4-Chloro-phenyl)-1H-imidazol-2-yl]-2-phenyl-ethyl}-5-[4-(2-hydroxy-ethoxy)-phenyl]-imidazolidine-2,4-dione;

(R)-3-{(1S,2S)-1-[5-(4-Chloro-phenyl)-1H-imidazol-2-yl]-2-phenyl-propyl}-5-[4-(2-hydroxy-ethoxy)-phenyl]-imidazolidine-2,4-dione;

(R)-3-{(S)-1-[5-(4-Chloro-2-fluoro-phenyl)-1H-imidazol-2-yl]-ethyl}-5-[4-(2-hydroxy-ethoxy)-phenyl]-imidazolidine-2,4-dione;

(R)-3-{(1S,2S)-1-[5-(4-Chloro-2-fluoro-phenyl)-1H-imidazol-2-yl]-2-phenyl-propyl}-5-[4-(2-hydroxy-ethoxy)-phenyl]-imidazolidine-2,4-dione; and (R)-3-{(1S,2S)-1-[5-(2,4-Dichloro-phenyl)-1H-imidazol-2-yl]-2-phenyl-propyl}-5-[4-(2-hydroxy-ethoxy)-phenyl]-imidazolidine-2,4-dione.

18. A compound of claim 1 selected from the group consisting of:

(R)-3-{(1S,2S)-1-[4-Chloro-5-(2-fluoro-4-iodo-phenyl)-1H-imidazol-2-yl]-2-phenyl-propyl}-5-[4-(2-hydroxy-ethoxy)-phenyl]-imidazolidine-2,4-dione;

(R)-3-{(1S,2S)-1-[4-Chloro-5-(4-chloro-2-fluoro-phenyl)-1H-imidazol-2-yl]-2-phenyl-propyl}-5-[4-(2-hydroxy-ethoxy)-phenyl]-imidazolidine-2,4-dione;

(R)-3-{(1S,2S)-1-[4-Chloro-5-(4-iodo-phenyl)-1H-imidazol-2-yl]-2-phenyl-propyl}-5-[4-(2-hydroxy-ethoxy)-phenyl]-imidazolidine-2,4-dione;

(R)-3-{(S)-1-[4-Chloro-5-(4-iodo-phenyl)-1H-imidazol-2-yl]-2-phenyl-ethyl}-5-[4-(2-hydroxy-ethoxy)-phenyl]-imidazolidine-2,4-dione;

(R)-3-{(1S,2S)-1-[4-Chloro-5-(2-fluoro-4-iodo-phenyl)-1H-imidazol-2-yl]-2-phenyl-propyl}-5-[4-((R)-2,3-dihydroxy-propoxy)-phenyl]-imidazolidine-2,4-dione;

(R)-3-{(1S,2S)-1-[4-Chloro-5-(2-fluoro-4-iodo-phenyl)-1H-imidazol-2-yl]-2-phenyl-propyl}-5-[4-((S)-2,3-dihydroxy-propoxy)-phenyl]-imidazolidine-2,4-dione;

(R)-3-{(1S,2S)-1-[4-Chloro-5-(2-fluoro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione;

(R)-3-{(1S,2S)-1-[4-Chloro-5-(2-chloro-4-iodo-phenyl)-1H-imidazol-2-yl]-2-phenyl-propyl}-5-[4-(2-hydroxy-ethoxy)-phenyl]-imidazolidine-2,4-dione;

(R)-3-{(1S,2S)-1-[4-Chloro-5-(2-chloro-4-iodo-phenyl)-1H-imidazol-2-yl]-2-phenyl-propyl}-5-[4-((R)-2,3-dihydroxy-propoxy)-phenyl]-imidazolidine-2,4-dione;

(R)-3-{(1S,2S)-1-[4-Chloro-5-(2-chloro-4-iodo-phenyl)-1H-imidazol-2-yl]-2-phenyl-propyl}-5-[4-((S)-2,3-dihydroxy-propoxy)-phenyl]-imidazolidine-2,4-dione; and (R)-3-{(1S,2S)-1-[4-Chloro-5-(2-chloro-4-iodo-phenyl)-1H-imidazol-2-yl]-2-phenyl-propyl}-5-[4-(2-hydroxy-1-hydroxymethyl-ethoxy)-phenyl]-imidazolidine-2,4-dione.

19. A compound of claim 2 wherein R5 is lower alkyl.

20. A pharmaceutical composition comprising a compound of claim 1 and a pharmaceutically acceptable diluent, excipient, or adjuvant.

21. A pharmaceutical composition comprising a compound of claim 2 and a pharmaceutically acceptable diluent, excipient, or adjuvant.

22. A pharmaceutical composition comprising a compound of claim 7 and a pharmaceutically acceptable diluent, excipient, or adjuvant.

23. A pharmaceutical composition comprising a compound of claim 12 and a pharmaceutically acceptable diluent, excipient, or adjuvant.

* * * * *